(12) United States Patent     (10) Patent No.:   US 12,558,563 B2

Moffat et al.     (45) Date of Patent:   *Feb. 24, 2026

(54) DYNAMIC DOSING SYSTEMS FOR PHOTOTHERAPY AND ASSOCIATED DEVICES, SYSTEMS, AND METHODS

(71) Applicant: SOLIUS LABS, INC., Bainbridge Island, WA (US)

(72) Inventors: William Alexander Moffat, Bainbridge Island, WA (US); Sen Wen, Bainbridge Island, WA (US); Linda Cox Arnsdorf, Bainbridge Island, WA (US); Eben Lynn Falconer Calhoun, Bainbridge Island, WA (US); Chieh-en Wu, Bellevue, WA (US)

(73) Assignee: SOLIUS LABS, INC., Bainbridge Island, WA (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/728,797

(22) Filed: Apr. 25, 2022

(65) Prior Publication Data

US 2022/0249863 A1    Aug. 11, 2022

Related U.S. Application Data

(62) Division of application No. 16/954,075, filed as application No. PCT/US2018/065537 on Dec. 13, 2018, now Pat. No. 11,311,744.

(Continued)

(51) Int. Cl.
   *A61N 5/06*       (2006.01)
   *A61B 5/00*       (2006.01)
         (Continued)

(52) U.S. Cl.
   CPC ............ *A61N 5/0616* (2013.01); *A61B 5/445* (2013.01); *G06F 3/048* (2013.01); *G06N 20/00* (2019.01);
         (Continued)

(58) Field of Classification Search
   CPC ................ A61N 5/0616; A61N 5/0614; A61N 2005/0627; A61N 2005/0615
   See application file for complete search history.

(56) References Cited

U.S. PATENT DOCUMENTS

| | | | |
|---|---|---|---|
| 5,265,598 A | 11/1993 | Searfoss et al. | |
| 5,531,664 A | 7/1996 | Adachi et al. | |

(Continued)

FOREIGN PATENT DOCUMENTS

| | | |
|---|---|---|
| CN | 101045177 | 10/2007 |
| CN | 101548895 | 10/2009 |

(Continued)

OTHER PUBLICATIONS

International Search Report and Written Opinion mailed Feb. 3, 2022 in International Patent Application No. PCT/US21/46578, 17 pages.

(Continued)

*Primary Examiner* — Lynsey C Eiseman

(74) *Attorney, Agent, or Firm* — Perkins Coie LLP

(57)          ABSTRACT

Dynamic dosing systems for phototherapy and associated devices, systems, and methods are disclosed herein. In some embodiments, a dynamic dosing phototherapy system can include a self-service phototherapy kiosk ("SPK") configured to emit UV radiation, a user interface communicatively coupled to the SPK, and a dynamic dosing system communicatively coupled to the user interface and the SPK. The dynamic dosing system can determine initial, user-specific parameters specific to define a first individual phototherapy (Continued)

protocol, and then determine adjustments to the initial parameters and the first individual phototherapy protocol based on user inputs related to erythema response to a previous phototherapy treatment session. The SPK can deliver UV radiation to a user in accordance with the first individual phototherapy protocol and/or an adjusted, second phototherapy protocol that takes into account the user's erythema response.

19 Claims, 21 Drawing Sheets

Related U.S. Application Data

(60) Provisional application No. 62/613,745, filed on Jan. 4, 2018, provisional application No. 62/599,242, filed on Dec. 15, 2017, provisional application No. 62/599,252, filed on Dec. 15, 2017.

(51) Int. Cl.

| | |
|---|---|
| *G06F 3/048* | (2013.01) |
| *G06N 20/00* | (2019.01) |
| *G16H 20/13* | (2018.01) |
| *G16H 20/40* | (2018.01) |

(52) U.S. Cl.
CPC ............. *G16H 20/13* (2018.01); *G16H 20/40* (2018.01); *A61N 2005/0627* (2013.01); *A61N 2005/0628* (2013.01); *A61N 2005/0632* (2013.01); *A61N 2005/064* (2013.01); *A61N 2005/0661* (2013.01)

(56) References Cited

U.S. PATENT DOCUMENTS

| | | | |
|---|---|---|---|
| 5,576,591 | A | 11/1996 | Werner |
| 6,402,774 | B1 | 6/2002 | Caldironi |
| 6,413,268 | B1 | 7/2002 | Hartman |
| 6,436,127 | B1 | 8/2002 | Anderson et al. |
| 6,567,999 | B1 | 5/2003 | Thurner |
| 7,638,780 | B2 | 12/2009 | Kilburn et al. |
| 8,647,373 | B1 | 2/2014 | Shepherd et al. |
| 10,226,641 | B2 | 3/2019 | Moffat |
| 2001/0003800 | A1 | 6/2001 | Crowley |
| 2003/0045916 | A1 | 3/2003 | Anderson et al. |
| 2003/0100935 | A1 | 5/2003 | Kratz |
| 2004/0138726 | A1 | 7/2004 | Savage |
| 2004/0186082 | A1 | 9/2004 | Hartman |
| 2004/0225339 | A1 | 11/2004 | Yaroslavsky et al. |
| 2005/0015124 | A1 | 1/2005 | Irwin |
| 2005/0143793 | A1 | 6/2005 | Korman et al. |
| 2005/0148270 | A1 | 7/2005 | Eden |
| 2005/0261750 | A1 | 11/2005 | McDaniel |
| 2006/0106435 | A1 | 5/2006 | Fraval |
| 2006/0151709 | A1 | 7/2006 | Hahl |
| 2006/0206173 | A1 | 9/2006 | Gertner et al. |
| 2006/0217789 | A1 | 9/2006 | Perez |
| 2007/0208395 | A1 | 9/2007 | Leclerc |
| 2007/0233210 | A1 | 10/2007 | Morita et al. |
| 2008/0103560 | A1 | 5/2008 | Powell et al. |
| 2008/0125834 | A1 | 5/2008 | Hendrix et al. |
| 2008/0172113 | A1 | 7/2008 | Gourgouliatos et al. |
| 2008/0211378 | A1 | 9/2008 | Dutta et al. |
| 2008/0224592 | A1 | 9/2008 | Reich et al. |
| 2008/0312721 | A1 | 12/2008 | Lemieux |
| 2009/0005839 | A1 | 1/2009 | Griffith et al. |
| 2009/0020711 | A1 | 1/2009 | Hansmann et al. |
| 2009/0093799 | A1 | 4/2009 | Davenport et al. |
| 2009/0118799 | A1 | 5/2009 | Nanninga |
| 2009/0134345 | A1 | 5/2009 | Gentry et al. |
| 2010/0185064 | A1 | 7/2010 | Bandic et al. |
| 2010/0241196 | A1 | 9/2010 | Meyer |
| 2010/0331929 | A1 | 12/2010 | Burrows et al. |
| 2011/0004280 | A1 | 1/2011 | Irwin |
| 2011/0212410 | A1 | 9/2011 | Fiset |
| 2011/0218595 | A1 | 9/2011 | McMillan |
| 2011/0299056 | A1 | 12/2011 | Williamson et al. |
| 2012/0039827 | A1 | 2/2012 | Chaudhuri |
| 2012/0071954 | A1 | 3/2012 | Kao et al. |
| 2012/0148976 | A1 | 6/2012 | Brawn |
| 2012/0282135 | A1 | 11/2012 | Trapani |
| 2013/0018442 | A1 | 1/2013 | Irwin et al. |
| 2013/0030264 | A1 | 1/2013 | Gopalakrishnan et al. |
| 2013/0131762 | A1 | 5/2013 | Oversluizen |
| 2013/0172963 | A1* | 7/2013 | Moffat ................. A61N 5/0616 607/94 |
| 2013/0231720 | A1 | 9/2013 | Luellau |
| 2013/0245724 | A1 | 9/2013 | Kaufman |
| 2013/0253621 | A1 | 9/2013 | DeLuca et al. |
| 2013/0310730 | A1 | 11/2013 | Goren et al. |
| 2014/0074193 | A1 | 3/2014 | Luzon |
| 2014/0121732 | A1 | 5/2014 | Goren et al. |
| 2014/0276248 | A1 | 9/2014 | Hall |
| 2014/0277299 | A1 | 9/2014 | Intintoli |
| 2015/0087685 | A1 | 3/2015 | Khan |
| 2015/0088231 | A1 | 3/2015 | Rubinfeld |
| 2015/0102208 | A1 | 4/2015 | Appelboom et al. |
| 2015/0165229 | A1 | 6/2015 | Rodrigues |
| 2015/0217130 | A1 | 8/2015 | Gross et al. |
| 2015/0217132 | A1 | 8/2015 | Makkapati et al. |
| 2015/0238774 | A1 | 8/2015 | Anderson et al. |
| 2016/0048826 | A1 | 2/2016 | Fefferman |
| 2016/0129279 | A1 | 5/2016 | Ferolito |
| 2016/0303395 | A1 | 10/2016 | Moffat |
| 2016/0317686 | A1 | 11/2016 | Dayton |
| 2017/0056238 | A1 | 3/2017 | Yi et al. |
| 2017/0118854 | A1 | 4/2017 | Dumon |
| 2017/0225006 | A1* | 8/2017 | Anderson ................ A61K 9/06 |
| 2018/0014777 | A1 | 1/2018 | Amir et al. |
| 2018/0056088 | A1 | 3/2018 | Moffat |
| 2018/0133503 | A1 | 5/2018 | Moffat |
| 2018/0206779 | A1* | 7/2018 | Kono ................... A61B 5/0064 |
| 2018/0353770 | A1* | 12/2018 | Moffat ................. A61N 5/0616 |
| 2018/0360709 | A1 | 12/2018 | Rabe et al. |
| 2018/0369604 | A1 | 12/2018 | Gamelin |
| 2019/0099613 | A1 | 4/2019 | Estes et al. |
| 2019/0133515 | A1 | 5/2019 | Park |
| 2019/0160303 | A1 | 5/2019 | Moffat, IV |
| 2020/0030628 | A1 | 1/2020 | Moffat et al. |
| 2020/0212265 | A1 | 7/2020 | Ho et al. |
| 2020/0376292 | A1 | 12/2020 | Moffat et al. |
| 2020/0391049 | A1 | 12/2020 | Moffat et al. |
| 2020/0396292 | A1 | 12/2020 | Moffat et al. |
| 2021/0128939 | A1 | 5/2021 | Verghese |
| 2021/0260402 | A1 | 8/2021 | Moffat et al. |
| 2022/0383496 | A1 | 12/2022 | D'Amelio |
| 2023/0347164 | A1 | 11/2023 | Lauder et al. |
| 2025/0050129 | A1 | 2/2025 | Good |

FOREIGN PATENT DOCUMENTS

| | | |
|---|---|---|
| CN | 201871131 | 6/2011 |
| CN | 104168953 | 7/2013 |
| CN | 107427688 | 8/2016 |
| CN | 106573155 | 4/2017 |
| DE | 7623367 | 2/1977 |
| DE | 3126236 | 1/1983 |
| DE | 9000705 | 3/1990 |
| DE | 19622074 | 12/1997 |
| DE | 20114790 | 12/2001 |
| DE | 10240716 | 3/2004 |
| DE | 202008004045 | 6/2008 |
| DE | 202008016045 | 4/2009 |
| EP | 0545887 | 6/1993 |
| EP | 1504792 | 2/2005 |
| EP | 1529552 | 5/2005 |
| EP | 1839703 | 10/2007 |
| EP | 1849497 | 10/2007 |
| EP | 1916017 | 4/2008 |
| EP | 2228098 | 9/2010 |
| GB | 2020970 | 11/1979 |

(56)                References Cited

FOREIGN PATENT DOCUMENTS

| | | |
|---|---|---|
| JP | H05-220231 | 8/1993 |
| JP | 10-295837 | 10/1998 |
| JP | 3075306 | 11/2000 |
| JP | 2008-500846 | 10/2005 |
| JP | 2007267936 | 10/2007 |
| JP | 2008-73148 | 4/2008 |
| WO | WO9917668 | 4/1999 |
| WO | WO200002491 | 1/2000 |
| WO | WO2003047682 | 6/2003 |
| WO | WO2007001364 | 1/2007 |
| WO | WO2007106856 | 9/2007 |
| WO | WO2007143862 | 12/2007 |
| WO | WO2008027438 | 3/2008 |
| WO | WO2010016009 | 2/2010 |
| WO | WO2011097383 | 8/2011 |
| WO | WO2012142427 | 10/2012 |
| WO | WO2013103743 | 7/2013 |
| WO | WO2015061773 | 4/2015 |
| WO | WO2015130891 | 9/2015 |
| WO | WO2016007798 | 1/2016 |
| WO | WO2016127120 | 8/2016 |
| WO | WO2016154343 | 9/2016 |
| WO | WO2016176360 | 11/2016 |
| WO | WO2016203461 | 12/2016 |
| WO | 2017019455 A2 | 2/2017 |
| WO | WO2017136891 | 8/2017 |
| WO | WO2018067411 | 4/2018 |
| WO | 2019118773 | 6/2019 |
| WO | WO2019118777 | 6/2019 |

OTHER PUBLICATIONS

International Search Report and Written Opinion mailed Jan. 19, 2018 in International Patent Application No. PCT/US17/54578, 15 pages.

Examination Report mailed Jan. 10, 2024 for European Patent Application No. 18888140.3, 4 pages.

Examiner's Report for mailed Mar. 8, 2024 for Canadian Patent Application No. 2,861,620, 4 pages.

Examiner's Report mailed Feb. 29, 2024 for Canadian Patent Application No. 3,036,581, 4 pages.

"Asahi Spectra Optical Filters," https://web.archive.org/web2010051608304/http://www.asahispectra.com/opticalfilters/uv_bandpass_filter.html; archive of website from 2010, 2 pages.

"Center Wavelength (CW) and Full Width at Half Maximum (GWHM) filter numbers," webpage at http://mdc.custhelp.com/app/answers/detail/a_id/19235/-/center-wavelength-%28cw%29-and-full-width-at-half-maximum-%28fwhm%29-filter-numbers, published Mar. 16, 2011, 1 page.

"Ergoline Vitamin D3 Solarium mit Dr. Holick UV-Systems," Sep. 2005, Ergoline GMBH Germany, Internet: www.ergoline. DE, 112 pages.

"Solaria Köln 2005," International Trade Fair for Sunlight Systems, Oct. 2005, English Google machine translation included, 9 pages.

Ala-Houhala, MJ., et al., "Comparison of narrow-band ultraviolet B exposures and oral vitamin D substitution on serum 25-hydroxyvitamin D concentration," Br J Dermatol. Apr. 2012. (5 pgs).

Australian Exam Report for co-pending Australian Application No. 2013206887, Applicant: BeneSol, Inc.; Date of Mailing: Feb. 24, 2017, 4 pages.

Bouillon, R., et al., "Action spectrum for production of previtamin D3 in human skin," CIE Technical Report 174, Commission International de l'Eclairage (CIE). 2006. (16 pgs).

Brozyna, et al., "Mechanism of UV-related carcinogenesis and its contribution to nevi/melanoma," Oct. 8, 2008, National Institute of Health Public Access, pp. 2 and 4.

Bruls, WA., et al., "Transmission of UV-radiation through human epidermal layers as a factor influencing the minimal erythema dose," Photochemistry and Photobiology. Jan. 1984. (5 pgs).

Bunker, JWM., et al., "Precise evaluation of ultraviolet therapy in experimental rickets," New England Journal of Medicine. 1937. (6 pgs).

Changaris, DG., et al., "Pulsed UVB Irradiation Converts 7-dehydrocholesterol to previtamin D3 and Photoproducts," 2001. (10 pgs).

Chen, TC., et al., "Factors that influence the cutaneous synthesis and dietary sources of vitamin D," Archives of Biochemistry and Biophysics. Apr. 15, 2007. (4 pgs).

Clemens, TL., et al., "Increased skin pigment reduces the capacity of skin to synthesise vitamin D3," Lancet. Jan. 1982. (3 pgs).

De Fabo, EC., et al., "Mechanism of immune suppression by ultraviolet irradiation in vivo. I. Evidence for the existence of a unique photoreceptor in skin and its role in photoimmunology," The Journal of Experimental Medicine. Jul. 1983. (15 pgs).

Devgun, MS., et al., "Tanning, protection against sunburn and vitamin D formation with a UV-A 'sun-bed'". The British Journal of Dermatology. Sep. 1982. (11 pgs).

Diffey, BL. "Observed and predicted minimal erythema doses: a comparative study," Photochemistry and Photobiology. Oct. 1994. (3 pgs).

Diffey, BL., et al., "A preliminary study on photoaddition and erythema due to UVB radiation," Physics in Medicine and Biology. Apr. 1984. (8 pgs).

English Translation of Chinese Office Action for Application No. 201480066635.X, Applicant: BeneSol, Inc., Date of Mailing: Nov. 7, 2017, 11 pages.

English translation of Chinese Office Action received for CN Application No. 201610833794.9, Applicant: BeneSol, Inc., Date of Mailing: Aug. 1, 2018, 13 pages.

English translation of Chinese Office Action received for CN Application No. 201680021252.X, Applicant: BeneSol, Inc., Date of Mailing: Jan. 18, 2019, 17 pages.

English translation of Chinese Office Action received for CN Application No. 201680037887.9, Applicant: BeneSol, Inc., Date of Mailing: Mar. 19, 2019, 19 pages.

English Translation of Japanese Office Action for Application No. 2014-550552, Applicant: BeneSol, Inc.; Date of Mailing: Oct. 4, 2016, 10 pages.

English Translation of Japanese Office Action for Application No. 2016-550685, Applicant: BeneSol, Inc.; Date of Mailing Aug. 23, 2018, 4 pages.

English Translation of Penultimate Japanese Office Action for Application No. 2017-074482, Applicant: BeneSol, Inc.; Date of Mailing: Oct. 29, 2018, 9 pages.

English Translation of Russian Office Action for Application No. 2014131906, Applicant: BeneSol, Inc.; Date of Mailing: Nov. 21, 2016, 10 pages.

English Translation of Second Japanese Office Action for Application No. 2014-550552, Applicant: BeneSol, Inc.; Date of Mailing: Jul. 28, 2017, 8 pages.

Examiner's Report for co-pending Canadian Patent Application No. 2,861,620, Applicant: BeneSol, Inc., Date of Mailing: Jul. 24, 2018, 4 pages.

Examiner's Requisition for Canadian Patent Application No. 2,861,620, Date of Mailing Nov. 5, 2021, 3 pages.

Extended European Search Report for co-pending European Patent Application No. 17195774.9, Applicant: BeneSol, Inc., Date of Mailing: May 17, 2018, 9 pages.

Extended European Search Report for European Patent Application No. 16747382.6, Applicant: BeneSol, Inc., Date of Mailing: Oct. 1, 2018, 8 pages.

Extended European Search Report for European Patent Application No. 16787092.2, Applicant: BeneSol, Inc., Date of Mailing: Jan. 18, 2019, 9 pages.

Extended European Search Report for European Patent Application No. 18887658.5, mailing date Sep. 27, 2021, 8 pages.

Extended European Search Report for European Patent Application No. 18888140.3, Date of Mailing Aug. 25, 2021, 8 pages.

Extended European Search Report in Application No. 13733883.6, Applicant: BeneSol, Inc., Date of Mailing: May 12, 2015, 7 pages.

(56)　　　　　References Cited

OTHER PUBLICATIONS

Extended European Search Report received for European Patent Application No. 17858943.8, Applicant: BeneSol, Inc., Date of Mailing: May 12, 2020, 9 pages.
Extended European Search Report received for European Patent Application No. 20183232.6, Applicant: BeneSol, Inc., Date of Mailing: Nov. 24, 2020, 8 pages.
Extended European Search Report received for European Patent Application No. 21192571.4, Applicant: BeneSol, Inc., Date of Mailing: Feb. 3, 2022, 10 pages.
Farr, PM., et al., "The erythemal response of human skin to ultraviolet radiation," The British Journal of Dermatology. Jul. 1985. (13 pgs).
First European Examination Report in Application No. 13733883.6, Applicant: BeneSol, Inc., Date of Mailing: Sep. 1, 2016, 4 pages.
First Examination Report for co-pending Australian Patent Application No. 2018200369, Applicant: BeneSol, Inc., Date of Mailing: Jun. 22, 2018, 2 pages.
Fitzpatrick, "The validity and practicality of sun-reactive skin types I through VI," Arch Dermatol. Jun. 1988, 124(6):869-71, 3 pages.
Galkin, ON., et al., "'Vitamin D' viodosimeter: basic characteristics and potential applications," Journal of Photochemistry and Photobiology. Nov. 1999. (8 pgs).
Guilhou, JJ., et al., "Vtiman D metabolism in psoriasis before and after phototherapy," Acta Derm Venereol. 1990. (5 pgs).
Haddad, JG., et al., "Human plasma transport of vitamin D after its endogenous synthesis," J Clin Invest. Jun. 1993. (4 pgs).
Holick, MF. "Environmental factors that influence the cutaneous production of vitamin D," Am J Clin Nutr. Mar. 1995. (8 pgs).
Holick, MF. "Sunlight, UV-radiation, vitamin D and skin cancer: how much sunlight do we need?" Advances in Experimental Medicine and Biology. 2008. (15 pgs).
Holick, MF., et al., "Skin as the site of vitamin D synthesis and target tissue for 1,25-dihydroxyvitamin D3. Use of calcitriol (1,25-dihydroxyvitamin D3) for treatment of psoriasis," Archives of Dermatology. Dec. 1987. (14 pgs).
Holick, MF., et al., "Photosynthesis of previtamin D3 in human skin and the physiologic consequences," Science. Oct. 1980. (3 pgs).
Holick, MF., et al., "Regulation of cutaneous previtamin D3 photosynthesis in man: skin pigment is not an essential regulator," Science. Feb. 1981. (4 pgs).
Holick, MF., et al., "The photoproduction of 1 alpha, 25-dihydroxyvitamin D3 in skin: an approach to the therapy of vitamin-D-resistant syndromes," The New England Journal of Medicine. Aug. 1980. (6 pgs).
Holick, MF., et al., "Vitamin D and skin physiology: a D-lightful story," Journal of Bone and Mineral Research. Dec. 22, 2007.1_6 pgs).
Hume, EM., et al., "On the Absorption of Vitamin D from the Skin," The Biochemical Journal. 1927. (6 pgs).
International Search Report and Written Opinion for International Application No. PCT/US2013/020179 filed Jan. 3, 2013, Applicant: BeneSol, Date of Mailing: Apr. 25, 2013, 13 pages.
International Search Report and Written Opinion for International Application No. PCT/US2014/062352 filed Oct. 27, 2014, Applicant: BeneSol, Inc., Date of Mailing: Feb. 5, 2015, 12 pages.
International Search Report and Written Opinion for International Application No. PCT/US2016/016873 filed Feb. 5, 2016, Applicant: BeneSol, Inc., Date of Mailing: May 5, 2016, 12 pages.
International Search Report and Written Opinion for International Application No. PCT/US2016/029615 filed Apr. 27, 2016, Applicant: BeneSol, Inc., Date of Mailing: Oct. 7, 2016, 14 pages.
International Search Report and Written Opinion for International Application No. PCT/US2018/065537 filed Dec. 13, 2018, Applicant: BeneSol, Inc., Date of Mailing: Mar. 1, 2019, 10 pages.
International Search Report and Written Opinion for International Application No. PCT/US2018/065542 filed Dec. 13, 2018, Applicant: BeneSol, Inc., Date of Mailing: Mar. 26, 2019, 8 pages.
Jablonski, NG., et al., "The evolution of human skin coloration," Journal of Human Evolution. Jul. 2000. (50 pgs).

Knudson, A., et al., "Quantitative studies of the effectiveness of ultraviolet radiation of various wave-lengths in rickets," Journal Biological Chemistry. 1938. (13 pgs).
Krause, R., et al., "UV radiation and cancer prevention: what is the evidence?" Anticancer Research. Jul. 2006. (5 pgs).
Lehmann, B., "The vitamin D3 pathway in human skin and its role for regulation of biological processes," Photochemistry and Photobiology. 2005. (6 pgs).
Lehmann, B., et al., "A novel pathway for hormonally active calcitriol," Hormone Research. 2000. (4 pgs).
Lehmann, B., et al., "Demonstration of UVB-induced synthesis of 1 alpha, 25-dihydroxyvitamin D3 (calcitriol) in human skin by microdialysis," Archives of Dermatological Research. Apr. 2003. (5 pgs).
Lehmann, B., et al., "Rold for tumor necrosis factor-alpha in UVB-induced conversion of 7-dehydrocholesterol to 1alpha,25-dihydroxyvitamin D3 in cultured keratinocytes," The Journal of Steroid Biochemistry and Molecular Biology. May 2004. (5 pgs).
Lehmann, B., et al., "The UVB-induced synthesis of vitamin D3 and 1alpha, 25-dihydroxyvitamin D3 (calcitriol) in organotypic cultures of keratinocytes: effectiveness of the narrowband Philips TL-01 lamp (311 nm)." J Steroid Biochem Mol Biol. Mar. 2007. (4 pgs).
Lehmann, B., et al., "UVB-induced conversion of 7-dehydrocholesterol to 1 alpha, 25-dihydroxyvitamin D3 (calcitriol) in the human keratinocyte line HaCaT," Photochemistry and Photobiology. Dec. 2000. (10 pgs).
Lehmann, B., et al., "UVB-induced conversion of 7-dehydrocholesterol to 1alpha, 25-dihydroxyvitamin D3 in an in vitro human skin equivalent model," The Journal of Investigative Dermatology. Nov. 2001. (7 pgs).
Lesiak, A., et al., "Vitamin D serum level changes in psoriatic patients treated with narrowband ultra violet B phototherapy are related to the season of the irradiation," Photodermatol Photoimmunol Photomed. Dec. 2011. (7 pgs).
Liu, W., et al., "Skin phototyping in a Chinese female population: analysis of four hundred and four cases from four major cities of China," Photodermatology, Photoimmuniology and Photomedicine. Aug. 2006. (5 pgs).
Maclaughlin, JA., et al., "Spectral character of sunlight modulates photosynthesis of previtamin D3 and its photoisomers in human skin," Science. May 1982. (3 pgs).
Marcus, M., "Make Your Day Better With D," USA Weekend. Nov. 2011. (3 pgs).
Maughan, G.H. "Ultra-violet wavelengths valuable in the cure of rickets in chickens," American Journal of Physiology. 1928. (18 pgs).
Mcloone, P., et al., "An action spectrum for the production of cis-urocanic acid in human skin in vivo," The Journal of Investigative Dermatology. May 2005. (4 pgs).
Mead, MN. "Benefits of sunlight: a bright spot for human health," Environmental Health Perspectives. Apr. 2008. (13 pgs).
Moan, J., et al., "Sunbeds as vitamin D Sources." Photochemistry and Photobiology. Nov. 2009. (8 pgs).
Nemanic, MK., et al., "In vitro synthesis of vitamin D-3 by cultured human keratinocytes and fibroblasts: action spectrum and effect of AY-9944," Biochimica et Biophysica Acta. Sep. 1985. (11 pgs).
Norval, M. et al., "Is the action spectrum for the UV-induced production of previtamin D3 in human skin correct?" Photochemical & Photobiological Sciences. Jan. 2010. (7 pgs).
Notice of Opposition filed for co-pending European Patent Application No. 13733883.6, issued as 2800605, Applicant: BeneSol, Inc., Date of Mailing: Jul. 31, 2018, 33 pages.
Obi-Tabot, ET., et al., "A human skin equivalent model that mimics the photoproduction of vitamin D3 in human skin," In Vitro Cellular & Developmental Biology. Mar. 2000. (6 pgs).
Olds, WJ., et al., "In vitro model of vitamin D3 (cholecalciferol) synthesis by UV radiation: dose-response relationships," Journal of Photochemistry and Photobiology. Nov. 2008. (6 pgs).
Osmancevic, A., et al., "UVB therapy increases 25(OH) vitamin D syntheses in postmenopausal women with psoriasis," Photodermatol Photoimmunol Photomed. Oct. 2007. (7 pgs).

(56) References Cited

OTHER PUBLICATIONS

Osmancevic, A., et al., "Vitamin D production in psoriasis patients increases less with narrowband thatn with broadband ultraviolet B phototherapy." *Photodermatol Photoimmunol Photomed.* Jun. 2009. (5 pgs).

Osmancevic, A., et al., "Vitamin D status in psoriasis patients during different treatments with phototherapy," *J Photochem Photobiol B.* Nov. 2010. (7 pgs).

Parrish, JA., et al., "Action spectrum for phototherapy of psoriasis," *The Journal of investigative Dermatology.* May 1981. (5 pgs).

Partial Supplementary European Search Report for co-pending European Patent Application No. 14856603.7, Applicant: BeneSol, Inc., Mailed Apr. 13, 2017, 7 pages.

Porojnicu, AC., et al., "Sun beds and cod liver oil as vitamin D sources," *Journal of Photochemistry and Photobiology.* May 2008. (7 pgs).

Ryan, C., et al., "The effect of narrowband UV-B treatment for psoriasis on vitamin D status during wintertime in Ireland," *Arch Dermatol.* Aug. 2010. (8 pgs).

Sage, RJ., et al., "UV-based therapy and vitamin D," *Dermatologic Therapy.* Jan. 2010. (10 pgs).

Scientific Committee On Consumer Products, "Opinion on Biological effects of ultraviolet radiation relevant to health with particular reference to sunbeds for cosmetic purposes," *European Commission Health & Consumer Protection Directorate-General.* 8th plenary of the SCCP on Jun. 20, 2006. (43 pgs).

Stamp, TC., et al., "Comparison of oral 25-hydroxycholecalciferol, vitamin D, and ultraviolet light as determinants of circulating 25-hydroxyvitamin D," *Lancet.* Jun. 25, 1977. (3 pgs).

Suh, KS., et al., "Long-term evaluation of erythema and pigmentation induced by ultraviolet radiations of different wavelengths," *Skin Research and Technology.* May 2007. (8 pgs).

Tangpricha, V., et al., "Tanning is associated with optimal vitamin D status (serum 25-hydroxyvitamn D concentration) and higher bone mineral density." *The American Journal of Clinical Nutrition.* Dec. 2004. (5 pgs).

Terenetskaya, I. "Two methods for direct assessment of the Vitamin D synthetic capacity of sunlight and artificial UV sources," *The Journal of Steroid Biochemistry and Molecular Biology.* May 2004. (4 pgs).

Vahavihu, K., et al. "Heliotherapy improves vitamin D balance and atopic dermatitis," *The British Journal of Dermatology.* Jun. 2008. (6 pgs).

Vantieghem, K., et al., "UVB-induced production of 1,25-dihydroxyvitamin D3 and vitamin D activity in human keratinocytes pretreated with a sterol delta7-reductase inhibitor," *J Cell Biochem.* May 2006. (12 pgs).

Walterscheid, JP., et al., "Cis-urocanic acid, a sunlight-induced immunosuppressive factor, activates immune suppression via the 5-HT2A receptor," *Proc. Natl. Acad. Sci. U.S.A.* Nov. 2006. (6 pgs).

Webb, A.R., et al., "The role of sunlight in the Cutaneous production of vitamin D3," *Annual Review of Nutrition.* 1988. (6 pgs).

Webb, AR., et al., "Sunlight regulates the cutaneous production of vitamin D3 by causing its photodegradation," *The Journal of Clinical Endocrinology and Metabolism.* May 1989. (6 pgs).

Weinstock, MA. "Assessment of sun sensitivity by questionnaire: validity of items and formulation of a prediction rule," *Journal of Clinical Epidemiology.* Aug. 2006. (6 pgs).

Whitmore, SE., et al., "Tanning salon exposure and molecular alterations," *Journal of the American Academy of Dermatology.* May 2001. (6 pgs).

Wolff Tanning Systems Website, Retrieved Mar. 21, 2012. (3 pgs).

Youn, JI., et al., "Assessment of the usefulness of skin phototype and skin color as the parameter of cutaneous narrow band UVB sensitivity in psoriasis patients," *Photodermatology, Photoimmunology and Photomedicine.* Oct. 2003. (4 pgs).

Yuen, AW., et al., "Vitamin D: in the evolution of human skin colour," *Medical Hypothesis.* Jan. 2010. (6 pgs).

Examiner's Report for Canadian Patent Application No. 2,861,620, Applicant: BeneSol, Inc., Date of Mailing: Jun. 14, 2023, 3 pages.

Invitation to Pay Additional Fees and Partial International Search dated Oct. 25, 2024 in International Patent Application No. PCT/US24/41352, 12 pages.

Extended European Search Report mailed Jul. 23, 2024 for European Patent Application No. 21859096.6, 8 pages.

Examiner's Report mailed Feb. 14, 2025 for Canadian Patent Application No. 3,085,326, 5 pages.

Examiner's Report mailed Jan. 21, 2025 for Canadian Patent Application No. 3,085,327, 4 pages.

Extended European Search Report mailed Feb. 27, 2025 for European Patent Application No. 24199219.7, 9 pages.

International Search Report and Written Opinion mailed Dec. 16, 2024 for International Patent Application No. PCT/US24/41352, 21 pages.

* cited by examiner

503

| TREATMENT FREQUENCY | ADAPTATION FACTOR 115% | | | | | ADAPTATION FACTOR 120% | | | | |
|---|---|---|---|---|---|---|---|---|---|---|
| ADAPTATION THRESHOLD | 10 | 9 | 8 | 7 | 6 | 10 | 9 | 8 | 7 | 6 |
| MAX INCREASE | 115% | 115% | 115% | 115% | 115% | 120% | 120% | 120% | 120% | 120% |
| PER DAY ADJUSTMENT | -1.88% | -2.14% | -2.50% | -3.00% | -3.75% | -2.50% | -2.86% | -3.33% | -4.00% | -5.00% |
| 2 | 115% | 115% | 115% | 115% | 115% | 120% | 120% | 120% | 120% | 120% |
| 3 | 113% | 113% | 113% | 112% | 111% | 118% | 117% | 117% | 116% | 115% |
| 4 | 111% | 111% | 110% | 109% | 108% | 115% | 114% | 113% | 112% | 110% |
| 5 | 109% | 109% | 108% | 106% | 104% | 113% | 111% | 110% | 108% | 105% |
| 6 | 108% | 106% | 105% | 103% | 100% | 110% | 109% | 107% | 104% | 100% |
| 7 | 106% | 104% | 103% | 100% | 96% | 108% | 106% | 103% | 100% | 95% |
| 8 | 104% | 102% | 100% | 97% | 93% | 105% | 103% | 100% | 96% | 90% |
| 9 | 102% | 100% | 98% | 94% | 89% | 103% | 100% | 97% | 92% | 85% |
| 10 | 100% | 98% | 95% | 91% | 85% | 100% | 97% | 93% | 88% | 80% |
| 11 | 98% | 96% | 93% | 88% | 81% | 98% | 94% | 90% | 84% | 75% |
| 12 | 96% | 94% | 90% | 85% | 78% | 95% | 91% | 87% | 80% | 70% |
| 13 | 94% | 91% | 88% | 82% | 74% | 93% | 89% | 83% | 76% | 65% |
| 14 | 92% | 89% | 85% | 79% | 70% | 90% | 86% | 80% | 72% | 60% |
| 15 | 91% | 87% | 83% | 76% | 66% | 88% | 83% | 77% | 68% | 55% |
| 16 | 89% | 85% | 80% | 73% | 63% | 85% | 80% | 73% | 64% | 50% |
| 17 | 87% | 83% | 78% | 70% | 59% | 83% | 77% | 70% | 60% | 45% |
| 18 | 85% | 81% | 75% | 67% | 55% | 80% | 74% | 67% | 56% | 40% |
| 19 | 83% | 79% | 73% | 64% | 51% | 78% | 71% | 63% | 52% | 35% |
| 20 | 81% | 76% | 70% | 61% | 48% | 75% | 69% | 60% | 48% | 30% |
| 21 | 79% | 74% | 68% | 58% | 44% | 73% | 66% | 57% | 44% | 25% |
| 22 | 77% | 72% | 65% | 55% | 40% | 70% | 63% | 53% | 40% | RESET |
| 23 | 76% | 70% | 63% | 52% | 36% | 68% | 60% | 50% | 36% | RESET |
| 24 | 74% | 68% | 60% | 49% | 33% | 65% | 57% | 47% | 32% | RESET |
| 25 | 72% | 66% | 58% | 46% | 29% | 63% | 54% | 43% | 28% | RESET |
| 26 | 70% | 64% | 55% | 43% | 25% | 60% | 51% | 40% | 24% | RESET |
| 27 | 68% | 61% | 53% | 40% | 21% | 58% | 49% | 37% | RESET | RESET |
| 28 | 66% | 59% | 50% | 37% | RESET | 55% | 46% | 33% | RESET | RESET |
| 29 | 64% | 57% | 48% | 34% | RESET | 53% | 43% | 30% | RESET | RESET |
| 30 | 62% | 55% | 45% | 31% | RESET | 50% | 40% | 27% | RESET | RESET |

| ADAPTATION FACTOR 125% | | | | | ADAPTATION FACTOR 130% | | | | |
|---|---|---|---|---|---|---|---|---|---|
| 10 | 9 | 8 | 7 | 6 | 10 | 9 | 8 | 7 | 6 |
| 125% | 125% | 125% | 125% | 125% | 130% | 130% | 130% | 130% | 130% |
| -3.13% | -3.57% | -4.17% | -5.00% | -6.25% | -3.75% | -4.29% | -5.00% | -6.00% | -7.50% |
| 125% | 125% | 125% | 125% | 125% | 130% | 130% | 130% | 130% | 130% |
| 122% | 121% | 121% | 120% | 119% | 126% | 126% | 125% | 124% | 123% |
| 119% | 118% | 117% | 115% | 113% | 123% | 121% | 120% | 118% | 115% |
| 116% | 114% | 113% | 110% | 106% | 119% | 117% | 115% | 112% | 108% |
| 113% | 111% | 108% | 105% | 100% | 115% | 113% | 110% | 106% | 100% |
| 109% | 107% | 104% | 100% | 94% | 111% | 109% | 105% | 100% | 93% |
| 106% | 104% | 100% | 95% | 88% | 108% | 104% | 100% | 94% | 85% |
| 103% | 100% | 96% | 90% | 81% | 104% | 100% | 95% | 88% | 78% |
| 100% | 96% | 92% | 85% | 75% | 100% | 96% | 90% | 82% | 70% |
| 97% | 93% | 88% | 80% | 69% | 96% | 91% | 85% | 76% | 63% |
| 94% | 89% | 83% | 75% | 63% | 92% | 87% | 80% | 70% | 55% |
| 91% | 86% | 79% | 70% | 56% | 89% | 83% | 75% | 64% | 48% |
| 88% | 82% | 75% | 65% | 50% | 85% | 79% | 70% | 58% | 40% |
| 84% | 79% | 71% | 60% | 44% | 81% | 74% | 65% | 52% | 33% |
| 81% | 75% | 67% | 55% | 38% | 78% | 70% | 60% | 46% | 25% |
| 78% | 71% | 63% | 50% | 31% | 74% | 66% | 55% | 40% | RESET |
| 75% | 68% | 58% | 45% | 25% | 70% | 61% | 50% | 34% | RESET |
| 72% | 64% | 54% | 40% | RESET | 66% | 57% | 45% | 28% | RESET |
| 69% | 61% | 50% | 35% | RESET | 63% | 53% | 40% | 22% | RESET |
| 66% | 57% | 46% | 30% | RESET | 59% | 49% | 35% | RESET | RESET |
| 63% | 54% | 42% | 25% | RESET | 55% | 44% | 30% | RESET | RESET |
| 59% | 50% | 38% | RESET | RESET | 51% | 40% | 25% | RESET | RESET |
| 56% | 46% | 33% | RESET | RESET | 48% | 36% | RESET | RESET | RESET |
| 53% | 43% | 29% | RESET | RESET | 44% | 31% | RESET | RESET | RESET |
| 50% | 39% | 25% | RESET | RESET | 40% | 27% | RESET | RESET | RESET |
| 47% | 36% | 21% | RESET | RESET | 36% | 23% | RESET | RESET | RESET |
| 44% | 32% | RESET | RESET | RESET | 33% | RESET | RESET | RESET | RESET |
| 41% | 29% | RESET | RESET | RESET | 29% | RESET | RESET | RESET | RESET |
| 38% | 25% | RESET | RESET | RESET | 25% | RESET | RESET | RESET | RESET |

*Fig. 5B*

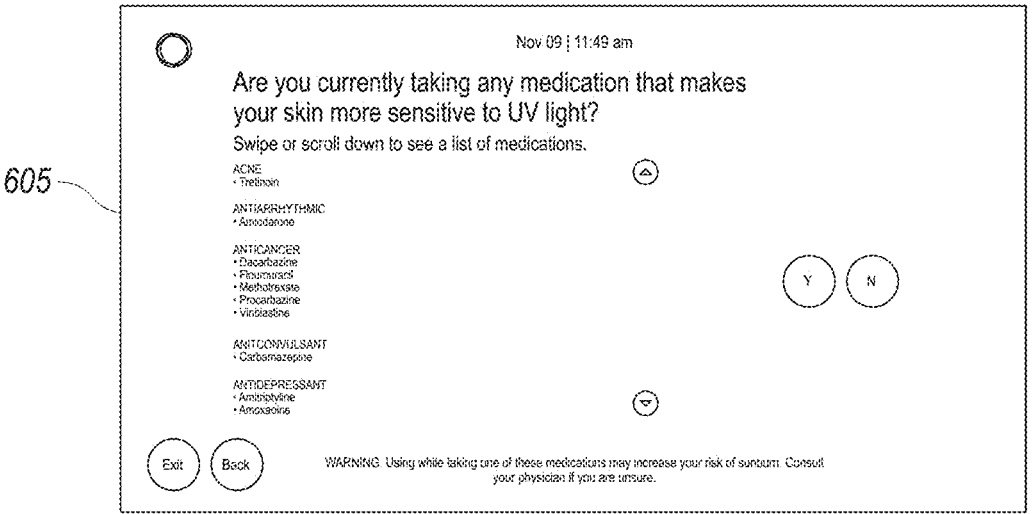

605

Nov 09 | 11:49 am

Are you currently taking any medication that makes
your skin more sensitive to UV light?

Swipe or scroll down to see a list of medications.

ACNE
• Tretinoin

ANTIARRHYTHMIC
• Amiodarone

ANTICANCER
• Dacarbazine
• Flourouracil
• Methotrexate
• Procarbazine
• Vinblastine ANITCONVULSANT
• Carbamazepine ANTIDEPRESSANT
• Amitriptyline
• Amoxapine

Y    N

Exit    Back        WARNING: Using while taking one of these medications may increase your risk of sunburn. Consult
your physician if you are unsure.

Nov 09 | 11:49 am

Are you currently taking any medication that makes
your skin more sensitive to UV light?

Swipe or scroll down to see a list of medications.

ACNE
• Tretinoin

ANTIARRHYTHMIC
• Amiodarone

ANTICANCER
• Dacarbazine
• Flourouracil
• Methotrexate
• Procarbazine
• Vinblastine ANITCONVULSANT
• Carbamazepine ANTIDEPRESSANT
• Amitriptyline
• Amoxapine

Y    N

Exit    Back        WARNING: Using while taking one of these medications may increase your risk of sunburn. Consult
your physician if you are unsure.

| MEASURE | POST EXPOSURE | QUESTION | ANSWERS |
|---|---|---|---|
| ERYTHEMA/SUNBURN | 18 - 48 H | DO YOU HAVE SUNBURN OR PINKNESS AS A RESULT OF YOUR LAST TREATMENT? | YES, NO |
| ERYTHEMA/SUNBURN | 18 - 48 H | WHAT DEGREE OF SUNBURN (IF ANY) DO YOU HAVE AFTER YOUR LAST TREATMENT? | NONE, VERY SLIGHT IN SPOTS, VERY SLIGHT, SLIGHT, MODERATE, SEVERE |
| ERYTHEMA/SUNBURN | 18 - 48 H | WHAT DEGREE OF SUNBURN (IF ANY) DO YOU HAVE AFTER YOUR LAST TREATMENT? | PICTURES SHOWING: NONE, E1, E2, E3, E4 EVENTS |
| ERYTHEMA/SUNBURN | 3 - 10 DAYS | DID YOU HAVE ANY SUNBURN OR PINKNESS AS A RESULT OF YOUR LAST TREATMENT? | YES, NO |
| ERYTHEMA/SUNBURN | 3 - 10 DAYS | WHAT DEGREE OF SUNBURN (IF ANY) DID YOU HAVE AFTER YOUR LAST TREATMENT? | NONE, VERY SLIGHT, SLIGHT, MODERATE, SEVERE |
| SKIN COLOR CHANGE | 18 - 48 H | DID YOU SEE ANY COLOR IN YOUR SKIN CHANGE AFTER YOUR LAST TREATMENT? | YES, NO |
| SKIN COLOR CHANGE | 3 - 10 DAYS | DID YOU SEE ANY COLOR CHANGE IN YOUR SKIN AFTER YOUR LAST TREATMENT? | YES, NO |
| SKIN COLOR CHANGE | 18 - 48 H | PLEASE DESCRIBE ANY SKIN COLOR CHANGE AFTER YOUR LAST TREATMENT. | NONE, NO PINK, SLIGHT PINK IN SPOTS, SLIGHT PINK, PINK, RED, DARK RED |
| SKIN COLOR CHANGE | 18 - 48 H | PLEASE DESCRIBE ANY SKIN COLOR CHANGE AFTER YOUR LAST TREATMENT. | NO CHANGE, TAN ONLY PINK WITH TAN, PINK ONLY, DARK PINK |
| LASTING COLOR CHANGE | 3 - 10 DAYS | DID YOUR SKIN COLOR CHANGE LAST MORE THAN 3 DAYS? | YES, NO |
| LASTING COLOR CHANGE | 7 - 14 DAYS | DID YOUR SKIN COLOR CHANGE LAST MORE THAN 7 DAYS? | YES, NO |
| LASTING COLOR CHANGE | 7 - 14 DAYS | HOW LONG DID YOUR SKIN COLOR CHANGE LAST? | LESS THAN 3 DAYS, 3-5 DAYS, 6-10 DAY, 10+ DAYS |
| TANNING | 18 - 48 H | DID YOUR SKIN TAN AS A RESULT OF YOUR LAST TREATMENT? | YES, NO |
| TANNING | 18 - 48 H | PLEASE DESCRIBE ANY TANNING AFTER YOUR LAST TREATMENT. | NONE, VERY SLIGHT, SLIGHT, MODERATE, DARK |
| TANNING | 3 - 10 DAYS | IS YOUR SKIN CURRENTLY TAN AS A RESULT OF YOUR LAST TREATMENT? | YES, NO |
| TANNING | 3 - 10 DAYS | PLEASE DESCRIBE CURRENT LEVEL OF TAN YOU HAVE FROM YOUR LAST TREATMENT. | NONE, VERY SLIGHT, SLIGHT, MODERATE, DARK |
| TANNING | 7 - 14 DAYS | DOES YOUR SKIN STILL HAVE A TAN RESULTING FROM YOUR LAST TREATMENT? | YES, NO |
| TANNING | 7 - 14 DAYS | PLEASE DESCRIBE CURRENT LEVEL OF TAN YOU HAVE FROM YOUR LAST TREATMENT. | NONE, T VERY SLIGHT, SLIGHT, MODERATE, DARK |
| DISCOMFORT/PAIN | 1 - 3 DAYS | DO YOU HAVE ANY SKIN DISCOMFORT OR PAIN FROM YOUR LAST TREATMENT? | YES, NO |
| DISCOMFORT/PAIN | 3 - 10 DAYS | DID YOU EXPERIENCE ANY SKIN DISCOMFORT OR PAIN FROM YOUR LAST TREATMENT? | YES, NO |
| DISCOMFORT/PAIN | 1 - 3 DAYS | DO YOU HAVE ANY SKIN DISCOMFORT OR PAIN FROM YOUR LAST TREATMENT? | NO, SLIGHT, MILD, MODERATE, SEVERE |
| DISCOMFORT/PAIN | 3 - 10 DAYS | DID YOU EXPERIENCE ANY SKIN DISCOMFORT OR PAIN FROM YOUR LAST TREATMENT? | NO, SLIGHT, MILD, MODERATE, SEVERE |
| DISCOMFORT/PAIN | 1 - 3 DAYS | HOW WOULD YOU DESCRIBE YOUR DISCOMFORT/PAIN? | SENSITIVE TO TOUCH, TENDER TO TOUCH, TENDER WITHOUT TOUCH, PAIN WITHOUT TOUCH |
| DISCOMFORT/PAIN | 1 - 3 DAYS | HOW WOULD YOU DESCRIBE YOUR DISCOMFORT/PAIN? | SENSITIVE TO HEAT OR TOUCH, DISCOMFORT WITHOUT TOUCH PAIN WITHOUT TOUCH |
| DISCOMFORT/PAIN | 1 - 3 DAYS | HOW WOULD YOU DESCRIBE YOUR DISCOMFORT/PAIN? | GRAPHIC FACES: HAPPY, MILD HAPPY, NOT HAPPY, SAD, VERY SAD, CRYING |
| DISCOMFORT/PAIN | 3 - 7 DAYS | HOW WOULD YOU DESCRIBE YOUR DISCOMFORT/PAIN? | MILD, MODERATE, SEVERE |
| DISCOMFORT/PAIN | 3 - 7 DAYS | DO YOU STILL HAVE DISCOMFORT OR PAIN RESULTING FROM YOUR LAST TREATMENT? | YES, NO |
| ITCHING | 3 - 14 DAYS | DID YOU EXPERIENCE ITCHY SKIN RESULTING FROM YOUR LAST TREATMENT? | YES, NO |
| PEELING | 7 - 14 DAYS | DID YOUR SKIN PEEL OR FLAKE AFTER YOUR LAST TREATMENT? | YES, NO |
| BLISTERS | 1+ DAYS | DID YOUR SKIN DEVELOP ANY BLISTERS AFTER YOUR LAST TREATMENT? | YES, NO |
| AREA OF IMPACT | 18 - 48 H | HOW MUCH OF YOUR SKIN IS AFFECTED? | SMALL PATCHES, SOME AREAS, MOST AREAS, ALL |
| AREA OF IMPACT | 18 - 48 H | ABOUT HOW MUCH OF YOUR SKIN IS AFFECTED? | 10%, 25%, 50%, 75%, 90% |
| AREA OF IMPACT | 2 - 5 DAYS | HOW MUCH OF YOUR SKIN IS AFFECTED? | SMALL PATCHES SOME AREAS, MOST AREAS, ALL |
| AREA OF IMPACT | 2 - 5 DAYS | ABOUT HOW MUCH OF YOUR SKIN IS AFFECTED? | 10%, 25%, 50%, 75%, 90% |
| AREA OF IMPACT | 3 - 10 DAYS | HOW MUCH OF YOUR SKIN WAS AFFECTED? | SMALL PATCHES, SOME AREAS, MOST AREAS, ALL |

*Fig. 11*

| MEASURE | ANSWER(S) | INDICATION |
|---|---|---|
| MPE DETERMINATION | | |
| ERYTHEMA/SUNBURN | VERY SLIGHT IN SPOTS, PICTURE: E1 IN SPOTS | MPE+ |
| SKIN COLOR CHANGE | SLIGHT PINK IN SPOTS | MPE+ |
| SKIN COLOR CHANGE | YES (UVB ONLY DEVICES) | MPE+ |
| LASTING COLOR CHANGE | NO, LESS THAN 3 DAYS | <MED |
| DISCOMFORT/PAIN | NO, GRAPHIC FACE: HAPPY | <E2 |
| ERYTHEMA/SUNBURN | YES, VERY SLIGHT IN SPOTS, VERY SLIGHT, PICTURE: E1 IN SPOTS | MPE+ |
| LASTING COLOR CHANGE | NO, LESS THAN 3 DAYS | <MED |
| DISCOMFORT/PAIN | NO, GRAPHIC FACE: HAPPY | <E2 |
| SKIN COLOR CHANGE | SLIGHT PINK IN SPOTS, SLIGHT PINK, PINK WITH TAN | MPE+ |
| LASTING COLOR CHANGE | NO, LESS THAN 3 DAYS | <MED |
| DISCOMFORT/PAIN | NO, GRAPHIC FACE: HAPPY | <E2 |
| SKIN COLOR CHANGE | YES (UVB ONLY DEVICES) | MPE+ |
| AREA OF IMPACT | SMALL PATCHES, 10% | <MED |
| DISCOMFORT/PAIN | NO, GRAPHIC FACE: HAPPY | <E2 |
| ERYTHEMA/SUNBURN | YES, VERY SLIGHT IN SPOTS, VERY SLIGHT, PICTURE: E1 IN SPOTS | MPE+ |
| AREA OF IMPACT | SMALL PATCHES, 10% | <MED |
| DISCOMFORT/PAIN | NO, GRAPHIC FACE: HAPPY | <E2 |
| SKIN COLOR CHANGE | SLIGHT PINK IN SPOTS, SLIGHT PINK, PINK WITH TAN | MPE+ |
| AREA OF IMPACT | SMALL PATCHES, 10% | <MED |
| DISCOMFORT/PAIN | NO, GRAPHIC FACE: HAPPY | <E2 |

| MEASURE | ANSWER(S) | INDICATION |
|---|---|---|
| | MED DETERMINATION | |
| ERYTHEMA/SUNBURN | VERY SLIGHT, PICTURE: E1 | MED |
| SKIN COLOR CHANGE | SLIGHT PINK | MED |
| SKIN COLOR CHANGE | YES (UVB ONLY DEVICES) | MPE+ |
| LASTING COLOR CHANGE | YES, >3 DAYS | MED+ |
| DISCOMFORT/PAIN | NO, GRAPHIC FACE: HAPPY | <E2 |
| ERYTHEMA/SUNBURN | YES, VERY SLIGHT, SLIGHT, PICTURE: E1 | MPE+ |
| LASTING COLOR CHANGE | YES, >3 DAYS | MED+ |
| DISCOMFORT/PAIN | NO, GRAPHIC FACE: HAPPY | <E2 |
| SKIN COLOR CHANGE | PINK, PINK WITH TAN | MED+ |
| LASTING COLOR CHANGE | YES, >3 DAYS | MED+ |
| DISCOMFORT/PAIN | NO, GRAPHIC FACE: HAPPY | <E2 |
| SKIN COLOR CHANGE | YES (UVB ONLY DEVICES) | MPE+ |
| AREA OF IMPACT | SOME AREAS, 25%, 50% | MED+ |
| DISCOMFORT/PAIN | NO, GRAPHIC FACE: HAPPY | <E2 |
| ERYTHEMA/SUNBURN | YES, VERY SLIGHT, SLIGHT, PICTURE: E1 | MPE+ |
| AREA OF IMPACT | SOME AREAS, 25%, 50% | MED+ |
| DISCOMFORT/PAIN | NO, GRAPHIC FACE: HAPPY | <E2 |
| SKIN COLOR CHANGE | PINK, PINK WITH TAN | MED+ |
| AREA OF IMPACT | SOME AREAS, 25%, 50% | MED+ |
| DISCOMFORT/PAIN | NO, GRAPHIC FACE: HAPPY | <E2 |

| E2 DETERMINATION | | |
|---|---|---|
| MEASURE | ANSWER(S) | INDICATION |
| | | |
| ERYTHEMA/SUNBURN | SLIGHT, PICTURE: E2 | E2 |
| | | |
| SKIN COLOR CHANGE | PINK | E2 |
| | | |
| SKIN COLOR CHANGE | YES (UVB ONLY DEVICES) | MPE+ |
| LASTING COLOR CHANGE | YES, >3 DAYS, 3-5 DAYS | MED+, E2+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |
| | | |
| ERYTHEMA/SUNBURN | YES, SLIGHT, MODERATE, PICTURE: E2 | MPE+, MED+, E2+ |
| LASTING COLOR CHANGE | YES, >3 DAYS, 3-5 DAYS | MED+, E2+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |
| | | |
| SKIN COLOR CHANGE | PINK, PINK WITH TAN, PINK ONLY | MED+, E2+ |
| LASTING COLOR CHANGE | YES, >3 DAYS, 3-5 DAYS | MED+, E2+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |
| SKIN COLOR CHANGE | YES, (UVB ONLY DEVICES) | MPE+ |
| AREA OF IMPACT | SOME AREAS, MOST AREAS, 50%, 75% | MED+, E3+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |
| | | |
| ERYTHEMA/SUNBURN | YES, SLIGHT, MODERATE, PICTURE: E2 | MPE+, MED+, E2+ |
| AREA OF IMPACT | SOME AREAS, MOST AREAS, 50%, 75% | MED+, E2+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |
| | | |
| SKIN COLOR CHANGE | PINK, PINK WITH TAN, PINK ONLY | MED+, E2+ |
| AREA OF IMPACT | SOME AREAS, MOST AREAS, 50%, 75% | MED+, E2+ |
| DISCOMFORT/PAIN | SLIGHT, MILD, SENSITIVE TO HEAT OR TOUCH, GRAPHIC FACE: MILD HAPPY, NOT HAPPY | E2+ |
| PEELING | NO | <E3 |

| E3 DETERMINATION | | |
|---|---|---|
| MEASURE | ANSWER(S) | INDICATION |
| | | |
| ERYTHEMA/SUNBURN | MODERATE, PICTURE: E3 | E3 |
| | | |
| SKIN COLOR CHANGE | RED | E3 |
| | | |
| SKIN COLOR CHANGE | YES (UVB ONLY DEVICES) | MPE+ |
| LASTING COLOR CHANGE | YES, >3 DAYS, 6+ DAYS | MED+, E2+ |
| DISCOMFORT/PAIN | MODERATE, TENDER WITH/WITHOUT TOUCH, DISCOMFORT WITHOUT TOUCH, GRAPHIC FACE: NOT HAPPY, SAD | E3+ |
| PEELING/ITCHING | YES | E3+ |
| BLISTER | NO | <E4 |
| | | |
| ERYTHEMA/SUNBURN | YES, MODERATE, SEVERE, PICTURE: E3 | MPE+, E2+, E3+ |
| LASTING COLOR CHANGE | YES, >3 DAYS, 6+ DAYS | MED+, E2+ |
| DISCOMFORT/PAIN | MODERATE, TENDER WITH/WITHOUT TOUCH, DISCOMFORT WITHOUT TOUCH, GRAPHIC FACE:NOT HAPPY, SAD | E3+ |
| PEELING/ITCHING | YES | E3+ |
| BLISTER | NO | <E4 |
| | | |
| SKIN COLOR CHANGE | RED, DARK PINK | E3+ |
| LASTING COLOR CHANGE | YES, >3 DAYS, 6+ DAYS | MED+, E2+ |
| DISCOMFORT/PAIN | MODERATE, TENDER WITH/WITHOUT TOUCH, DISCOMFORT WITHOUT TOUCH, GRAPHIC FACE: NOT HAPPY, SAD | E3+ |
| PEELING/ITCHING | YES | E3+ |
| BLISTER | NO | <E4 |
| SKIN COLOR CHANGE | YES, (UVB ONLY DEVICES) | MPE+ |
| AREA OF IMPACT | MOST AREAS, ALL, 75%, 90% | E2+, E3+ |
| DISCOMFORT/PAIN | MODERATE, TENDER WITH/WITHOUT TOUCH, DISCOMFORT WITHOUT TOUCH, GRAPHIC FACE: NOT HAPPY, SAD | E3+ |
| PEELING/ITCHING | YES | E3+ |
| BLISTER | NO | <E4 |
| | | |
| ERYTHEMA/SUNBURN | YES MODERATE, SEVERE, PICTURE: E3 | MPE+, E2+, E3+ |
| AREA OF IMPACT | MOST AREAS, ALL, 75%, 90% | E2+, E3+ |
| DISCOMFORT/PAIN | MODERATE, TENDER WITH/WITHOUT TOUCH, DISCOMFORT WITHOUT TOUCH, GRAPHIC FACE: NOT HAPPY, SAD | E3+ |
| PEELING/ITCHING | YES | E3+ |
| BLISTER | NO | <E4 |
| | | |
| SKIN COLOR CHANGE | RED, DARK PINK | E3+ |
| AREA OF IMPACT | MOST AREAS, ALL, 75%, 90% | E2+, E3+ |
| DISCOMFORT/PAIN | MODERATE, TENDER WITH/WITHOUT TOUCH, DISCOMFORT WITHOUT TOUCH, GRAPHIC FACE: NOT HAPPY, SAD | E3+ |
| PEELING/ITCHING | YES | E3+ |
| BLISTER | NO | <E4 |

| E4 DETERMINATION | | |
|---|---|---|
| MEASURE | ANSWER(S) | INDICATION |
| | | |
| ERYTHEMA/SUNBURN | SEVERE, PICTURE: E4 | E4 |
| | | |
| SKIN COLOR CHANGE | DARK RED | E4 |
| | | |
| SKIN COLOR CHANGE | YES (UVB ONLY DEVICES) | MPE+ |
| LASTING COLOR CHANGE | YES, >3 DAYS, 6+DAYS | MED+, E2+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |
| | | |
| ERYTHEMA/SUNBURN | YES, MODERATE, SEVERE, PICTURE: E3 | MPE+, E2+, E3+ |
| LASTING COLOR CHANGE | YES, >3 DAYS, 6+DAYS | MED+, E2+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |
| | | |
| SKIN COLOR CHANGE | RED, DARK PINK | E3+ |
| LASTING COLOR CHANGE | YES, >3 DAYS, 6+DAYS | MED+, E2+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |
| SKIN COLOR CHANGE | YES, (UVB ONLY DEVICES) | MPE+ |
| AREA OF IMPACT | MOST AREAS, ALL, 75%, 90% | E2+, E3+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |
| | | |
| ERYTHEMA/SUNBURN | YES, MODERATE, SEVERE, PICTURE: E3 | MPE+, E2+, E3+ |
| AREA OF IMPACT | MOST AREAS, ALL, 75%, 90% | E2+, E3+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |
| | | |
| SKIN COLOR CHANGE | RED, DARK PINK | E3+ |
| AREA OF IMPACT | MOST AREAS, ALL, 75%, 90% | E2+, E3+ |
| DISCOMFORT/PAIN | MODERATE, SEVERE, DISCOMFORT/TENDER/PAIN WITHOUT TOUCH, GRAPHIC FACE: SAD, VERY SAD, CRYING | E3+, E4 |
| PEELING/ITCHING | YES | E3+ |
| BLISTER | YES | E4 |

2100
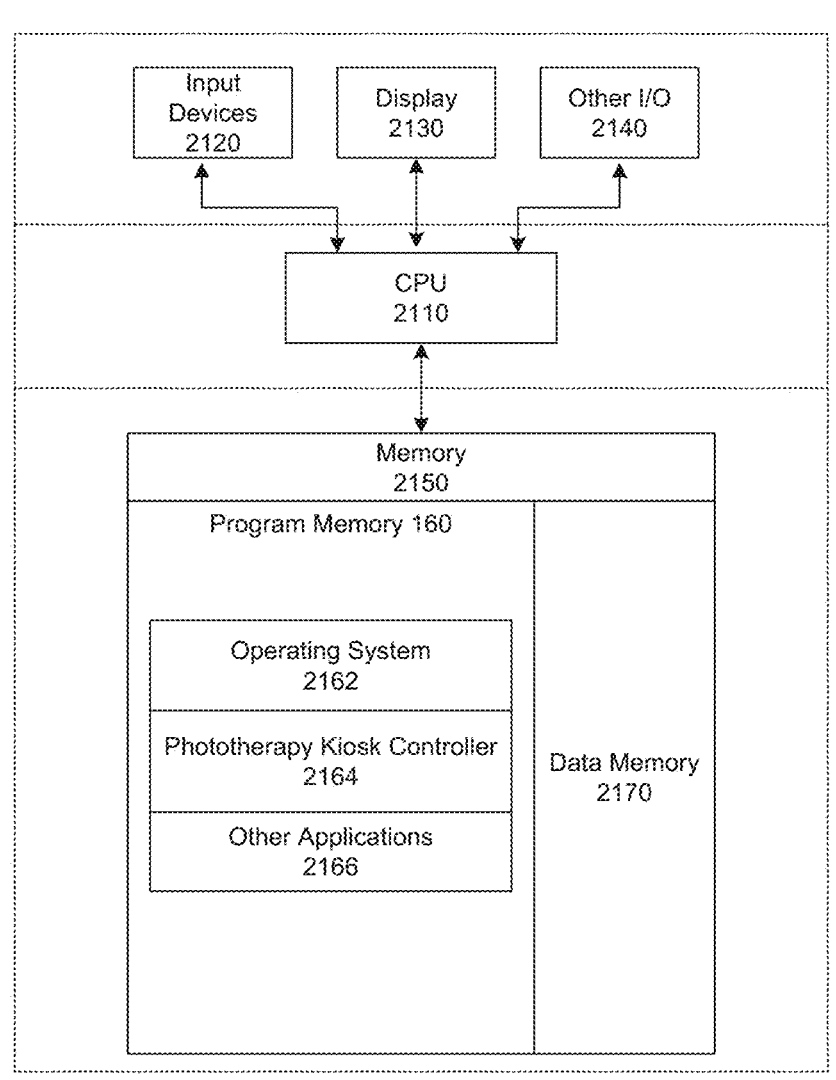
Input Devices
2120
Display
2130
Other I/O
2140
CPU
2110
Memory
2150
Program Memory 160
Operating System
2162
Phototherapy Kiosk Controller
2164
Other Applications
2166
Data Memory
2170
*FIG. 21*

DYNAMIC DOSING SYSTEMS FOR PHOTOTHERAPY AND ASSOCIATED DEVICES, SYSTEMS, AND METHODS

CROSS-REFERENCE TO RELATED APPLICATIONS

This application is a divisional of U.S. patent application Ser. No. 16/954,075, titled "DYNAMIC DOSING SYSTEMS FOR PHOTOTHERAPY AND ASSOCIATED DEVICES, SYSTEMS, AND METHODS", filed Jun. 15, 2020, which is a 35 U.S.C. § 371 U.S. National Phase application of International Patent Application No. PCT/US2018/065537, titled "DYNAMIC DOSING SYSTEMS FOR PHOTOTHERAPY AND ASSOCIATED DEVICES, SYSTEMS, AND METHODS," filed Dec. 13, 2018 which claims priority to U.S. Patent Application No. 62/599,242, titled "SYSTEMS AND METHODS FOR OPERATING PHOTOTHERAPY KIOSKS," filed Dec. 15, 2017, U.S. Provisional Patent Application No. 62/599,252, titled "DYNAMIC DOSING SYSTEM FOR PHOTOTHERAPY AND ASSOCIATED DEVICES AND METHODS," filed Dec. 15, 2017, and U.S. Patent Application No. 62/613,745, titled "SYSTEMS AND METHODS FOR OPERATING PHOTOTHERAPY KIOSKS," filed Jan. 4, 2018, the contents of each are hereby incorporated by reference in their entireties.

TECHNICAL FIELD

The present technology relates generally to phototherapeutic devices, systems, and methods. In particular, various embodiments of the present technology are related to dynamic dosing systems for phototherapy and associated devices and methods.

BACKGROUND

Vitamin D refers to a group of fat-soluble secosteroids that the human body can synthesize through adequate exposure to sunlight. More specifically, vitamin D3 is made in the skin when 7-dehydrocholesterol reacts with ultraviolet B ("UVB") light. Vitamin D can also be absorbed from the various dietary sources, such as fatty fish (e.g., salmon and tuna), vitamin D fortified foods (e.g., dairy and juice products), and vitamin D supplements. Once absorbed, the vitamin D travels through the bloodstream to the liver where it is converted into the prohormone calcidiol. The calcidiol is, in turn, converted into calcitriol (the hormonally active form of vitamin D) by the kidneys or monocyte-macrophages in the immune system. When synthesized by the monocyte-macrophages, calcitriol acts locally as a cytokine to defend the body against microbial invaders. Kidney-synthesized calcitriol circulates through the body to regulate the concentration of calcium and phosphate in the bloodstream, and thereby promotes adequate mineralization, growth, and reconstruction of the bones. Therefore, an inadequate level of vitamin D, (typically characterized by a calcidiol concentration in the blood of less than 20-40 ng/m2) can cause various bone softening diseases, such as rickets in children and osteomalacia in adults. Vitamin D deficiency has also been linked to numerous other diseases and disorders, such as depression, heart disease, gout, auto-immune disorders, and a variety of different cancers.

Recently, vitamin D deficiency has become a prominent condition due, at least in part, to increasingly metropolitan populations and the resultant indoor lifestyles that inhibit adequate daily exposure to sunlight for vitamin D production. The growing emphasis on skin cancer awareness and sunscreen protection, which blocks UVB rays, may have also increased the spread of vitamin D deficiency. Additionally, various environmental factors, such as geographic latitude, seasons, and smog, further impede sufficient vitamin D production.

Physicians have recommended vitamin D supplements as a preventative measure to increase vitamin D levels. The American Institute of Medicine, for example, recommends a daily dietary vitamin D intake of 600 international units (IU) for those 1-70 years of age, and 800 IU for those 71 years of age and older. Other institutions have recommended both higher and lower daily vitamin D doses. The limitations on daily dosages also reflect an effort to prevent ingesting too much vitamin D, which can eventually become toxic. In contrast, the human physiology has adapted to significantly higher daily doses of vitamin D from sunlight (e.g., 4,000-20,000 IU/day or more). UVB radiation has been identified as a more desirable source of vitamin D because of the ease at which vitamin D is produced from exposure to sunlight and the body's natural ability to inhibit excessive vitamin D intake through the skin.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 5A-5B illustrate a photoadaptation modification matrix for use with phototherapy systems configured in accordance with embodiments of the present technology.

FIG. 6 illustrates a medication identification GUI configured in accordance with embodiments of the present technology.

FIG. 7 illustrates a UV exposure GUI configured in accordance with embodiments of the present technology.

FIG. 11 is an erythema response matrix for use with phototherapy systems configured in accordance with embodiments of the present technology.

FIG. 12 is a matrix for assessing minimal perceived for phototherapy systems configured in accordance with embodiments of the present technology.

FIG. 13 is a matrix for assessing minimal erythemal dose determination for phototherapy systems configured in accordance with embodiments of the present technology.

FIG. 14 is a second-degree erythema assessment matrix for defining treatment protocols of phototherapy systems configured in accordance with embodiments of the present technology.

FIG. 15 is a third-degree erythema assessment matrix for defining treatment protocols of phototherapy systems configured in accordance with embodiments of the present technology.

FIG. 16 is a fourth-degree erythema assessment matrix for defining treatment protocols of phototherapy systems configured in accordance with embodiments of the present technology.

FIG. 21 is a block diagram illustrating an overview of devices on which some implementations can operate.

DETAILED DESCRIPTION

Figure 1:
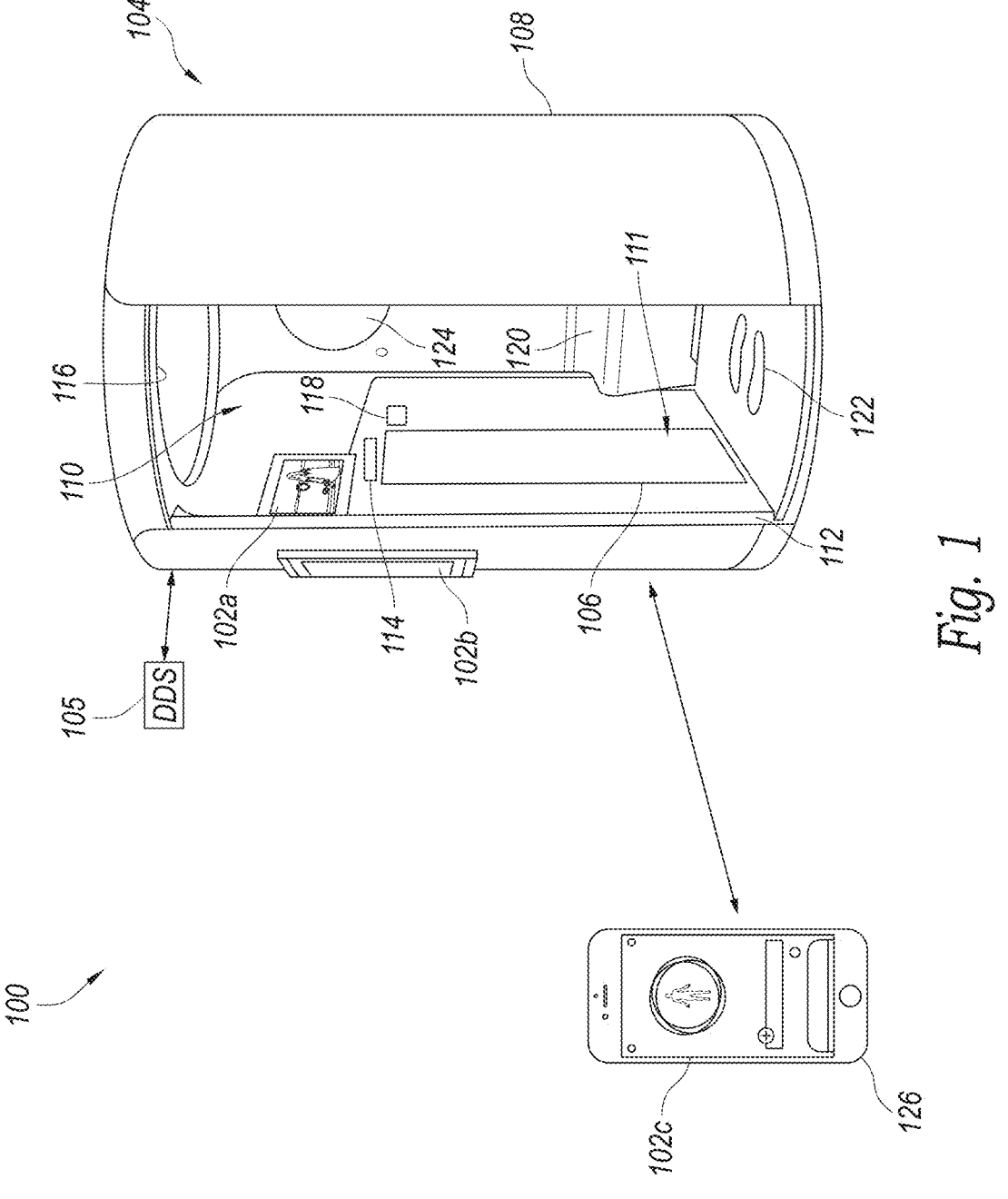
FIG. 1 is an isometric view of a dynamic dosing phototherapy system configured in accordance with embodiments of the present technology.

The present technology is generally directed to dynamic dosing systems for phototherapy and associated devices and methods. For example, this description includes disclosure of the following: phototyping; individual minimal perceived erythema (MPE), minimal erythemal dose (MED) and starting dose; photosensitivity screening dose (PSD); Individual Treatment Dose ($TD_i$); age adjustment to dose; delivery dose; photoadaptation modification ($Mod_p$); medication modification ($Mod_m$); recent UV modification ($Mod_u$); user reported erythema response; treatment frequency recommendation ($TF_R$) and limit ($TF_L$); photosensitivity discovery dose (PDD); and feedback adjustment.

Specific details of several embodiments of the present technology are described herein with reference to drawings. Although many of the embodiments are described with respect to devices, systems, and methods for phototherapy systems for stimulating vitamin D production via the skin, other embodiments in addition to those described herein are within the scope of the present technology. For example, at least some embodiments of the present technology may be useful for the treatment of various indications, such as skin diseases (e.g., psoriasis) and autoimmune diseases. Furthermore, at least some embodiments of the present technology may be used to provide preventative therapies. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

Relevant Physiology and Technology

""Phototherapy devices are typically designed to use ultraviolet radiation ("UVR"), with wavelengths of 250 nm-400 nm, for treatment of dermatologic disorders or cosmetic tanning. Phototherapy can also be used in the prevention or treatment of a variety of conditions that impact many systems of the human body. Sunlight exposure produces vitamin D as well as several other hormones and peptides that positively impact human health. Vitamin D insufficiency due to lack of sun exposure has been linked to several chronic health problems including autoimmune, neurological, musculoskeletal, cardiovascular disease, hypertension, metabolic syndromes and common cancers. Vitamin D and UVR can boost innate immune function, with antimicrobial actions helping to fight infections and anti-inflammatory properties having a role in the prevention and treatment of inflammatory diseases like fibromyalgia, rheumatoid arthritis and osteoarthritis. Modern human indoor lifestyles and potential concerns regarding the deleterious effects of excessive UVR on human health (e.g., skin cancer, sunburn, photoaging) prevent many people from receiving adequate sunlight exposure. The general population use of phototherapy can serve to improve the systemic health of the human body and mind while limiting negative effects.

A common feature of phototherapy is the delivery of non-ionizing radiation to the body to elicit a biological response, regardless of the exact mechanism of action within the body. The mechanism of action for endogenous vitamin D production is the photoisomerization of 7-dehydrocholesterol to previtamin D3 in the epidermis with exposure to UVB radiation (i.e., wavelengths of 280-320 nm). For autoimmune disorders of the skin, radiation is absorbed by endogenous chromophores, such as nuclear DNA, which stimulates a cascade of events that lead to alteration of cytokine profile, induction of apoptosis and promotion of immunosuppression. In cosmetic sun tanning devices, UVB radiation initiates cellular damage in keratinocytes, which stimulates hormonal signaling that promotes melanogenesis while UVA radiation (i.e., wavelengths of 321-400 nm) leads to rapid darkening of the melanin and melanin oxidation. The primary target for phototherapy is typically the skin, where different wavelengths of light penetrate different layers of the skin or even into the subdermal capillary bed.

UVR is a well-known human carcinogen that can cause direct DNA damage or oxidative stress that can lead to erythema (i.e., sunburn), non-melanoma skin cancer, malignant melanoma and premature skin aging of the skin as well as ocular damage, such as photokeratitis, photoretinitis or cataract. The damaging effects of UVR can be amplified when combined with light allergies, abnormal light sensitivity, photosensitizing medications or recent UVR exposure. Thus, the challenge for UVR-based phototherapy applications is delivering a safe and effective dose. This is especially true for self-care applications, as the long-term negative effects of UVR are not immediately apparent to the user.

Phototherapy devices have been developed for various indications for three major usage environments (medical clinic, at-home and tanning salons), but have undergone very little change to the user operation. For example, phototherapy devices may have differing spectral outputs depending on the desired result (e.g., treating a specific skin disorder, tanning skin), but the devices still operate like a standard light bulb with a timer. Prescriptive devices have been developed for dermatologic disorders to provide controlled delivery of UVR using various wavelength combinations, including: Broadband UVB (BBUVB 280-320 nm); Narrowband UVB (NBUVB 311-313 nm); excimer laser (308 nm); UVA (340-400 nm); and UVA with psoralen (PUVA). Most dermatologic devices are designed for a clinical setting, where a technician sets the device timer according to a prescribing treatment regime. Prescriptive at-home devices have been developed, allowing patients to set the device according to dermatologist instruction. Cosmetic tanning devices, including both commercial and at-home tanning devices, currently use a sunlight-similar UVA/UVB composition in a full body bed or booth configuration. Similar to the timer-based clinical phototherapy devices, these cosmetic tanning devices are primarily utilized by tanning salons where a technician sets exposure time based on regulatory guidance that is printed on the device. At-home versions of tanning devices are used according to the same regulatory guidance. Thus, current medical and cosmetic phototherapy devices are essentially ""dumb"" light-boxes that require manual user instruction (e.g., selection of timer duration), regardless of the operational environment, indication of use, safety considerations, prescriptive requirements or over-the-counter ("OTC") needs. Dose recommendations are static and require patient or clinician interpretation of individual skin response to make dose adjustments to prevent sunburn while still allowing effective treatment.

Erythema is the reddening of the skin induced by increased blood flow to the capillaries in the lower skin layers and is a potential consequence of UVR exposure commonly called sunburn. An action spectrum is the rate of a physiological activity plotted against wavelength of light, and therefore depicts which wavelength of light is most effective in a photochemical or physiologic reaction. The action spectrum for erythema provides a weighting factor for spectral irradiance and defines 10 mJ/cm$^2$ of erythemal effective radiant exposure as 1 Standard Erythema Dose (SED).

The ability for a UVR source to elicit the cutaneous production of vitamin $D_3$, immune response for dermatologic treatment and sunburn is highly wavelength dependent. However, the action spectra for vitamin D3 production, psoriasis treatment and erythema are very similar. This means that spectrum isolation cannot change the paradigm that increasing dose of radiation (i.e., the amount of energy applied per unit area at predefined wavelengths, measured, e.g., as mJ/cm$^2$), increases efficacy, but also increases direct DNA damage that leads to sunburn. Therefore, precise dosing can provide for effective vitamin $D_3$ synthesis or dermatologic treatment (or other UVR applications) without sunburn. However, although the propensity for a UVR source to produce a biological response (e.g., erythema) can be calculated using weighting factors, the actual dose needed to produce a clinical response (photosensitivity) in humans is not static and cannot be standardized.

Individual photosensitivity can be precisely determined using a phototesting protocol performed by dermatologists or other clinicians. The procedure includes exposing several patches of skin to graduated dosage points, and then visually scoring the skin patches in view of clinical criteria 24-hours after exposure. The lowest dose of radiation (mJ/cm$^2$) necessary to produce minimal perceptible erythema with well-defined borders is considered 1 Minimal Erythemal Dose (MED). The lowest possible gradation of erythema is Minimal Perceivable Erythema (MPE), at which there is a slight noticeable color change, but without the clearly defined borders of MED. Previous studies using instrumentation to measure vasodilation increase after UVB exposure have found that erythema response has a direct linear correlation with increasing dose up to 15 MED. Researcher have concluded that MED lies on the lower end of the linear dose-response curve and is therefore a visual detection threshold rather than a response threshold. Therefore, MED is a useful threshold that can serve as a predictor of mild sunburn. As described in Table 1, mild sunburn, which is clinically referred to as second-degree erythema("$E_2$"), usually subsides after three to four days and is expected to result from 2.5 times the MED dose. While MED and MPE determinations may be useful indicators of individualized photosensitivity, MED phototesting must be performed by clinicians with specific skin masking procedures and the results cannot be obtained until 24-hours post exposure. Therefore, MED phototesting does not provide automated or quick photosensitivity determinations that would facilitate/or the rapid creation of phototherapy protocols, which could be used for OTC applications or same-visit clinical applications.

TABLE 1

| Clinical Erythema Degree Assessment | |
| --- | --- |
| First Degree ($E_1$) | a just perceptible erythema, often referred to as a minimal erythema dose (MED), which lasts for about 24 h and leaves the skin apparently unchanged. |
| Second Degree ($E_2$) | a response resembling a mild sunburn which subsides after 3-4 d and may be followed by tanning |
| Third Degree ($E_3$) | a severe reaction in which the erythema is accompanied by edema and tenderness. The reaction lasts for several days, pigmentation is more apparent, and exfoliation is marked; the skin often peels of in sheets or flakes. |
| Fourth Degree ($E_4$) | the initial changes are the same as an $E_3$ reaction, but the edema and exudation are so severe that a blister is formed. |

Although the dose response characteristic of erythema is a marked function of wavelength, as a rough guide, the relative exposure times for irradiation with a medium-pressure mercury arc lamp needed to produce an $E_1$ through to an $E_4$ are in the ratio 1:2.5:5:10.

The lowest dose of radiation needed to produce pigmentation with well-defined borders seven days after exposure defines the Minimum Melanogenesis Dose (MMD), whereas trace pigment anywhere in the exposure field seven days after exposure defines the Minimally Perceptible Pigmentation (MPP). It has been shown that MMD is greater than MED for UVB light sources (MMD/MED ratio >1), and that NBUVB has a MMD/MED ratio of 1.4 to 2.0 depending on skin type. Consequently, pigmentary changes seen in the skin seen lasting more than 6 days with well-defined borders resulted from an exposure in excess of 1 MED. One study documented that 10 exposures over four weeks with UVB at 0.75MED was unable to induce pigmentation. Therefore, it is expected that the MPP/MPE ratio for UVB is also greater than 1, but not definitively characterized. Devices that emit about 5% UVB (similar to sunlight) have a MMD/MED ratio of 1.38 with a single exposure, but that ratio decreases to 1.16 with repeated sub-erythemal exposures. For devices that contain greater than 99% UVA, the MMD/MED ratio is less than 1 (e.g., 0.71), and therefore MPP is also likely to occur before MPE in these devices. Therefore, self-assessed lasting pigment change is expected to be a reliable indicator of UVR doses that exceed 1 MPE with UVB phototherapy devices. For devices that emit less than 5% UVB, pigmentary changes without other clear signs of erythema are not expected to serve as a reliable indicator of UVR doses that exceed 1 MPE or 1 MED.

Pain or discomfort is common symptom associated with third degree erythema ($E_3$) and fourth degree erythema ($E_4$), but hyperalgesia (heightened sensitivity to pain) can be induced by lower UVR doses needed to produce $E_1$ to $E_2$ reactions. This increased sensitivity can cause mechanical or thermal discomfort from common activities such as wearing clothing or bathing. Doses of UVR from one to three MED produce a dose-dependent increase in hyperalgesia that corelates to erythema intensity and duration without unprovoked pain. The time-course of hyperalgesia also correlates with erythema intensity, reaching a peak between 24 and 48 hours post-exposure. As with erythema, both thermal and mechanical hyperalgesia intensity and duration is primarily driven by UVB irradiance. When equal erythemally weighted doses (one to three MED) are delivered from devices that have a high or low UVA/UVB ratio, the thermal and mechanical hyperalgesia response is nearly identical and highly correlated with UVR dose, even when a plateau erythema response is seen for high UVA/UVB ratio devices between two and three MED. This means hyperalgesia is a reliable measure of UVR doses that exceed 1 MED, regardless of the spectral composition of the device emissions. Therefore, self-assessed discomfort after UVR exposure is expected to provide a reliable indication that a UVR dose exceeds 1 MED.

The Fitzpatrick Skin Type ("FST") classification is correlated to MED and skin color. Increased melanin provides photoprotection, decreasing sun sensitivity and directly correlating with higher UVR dosage requirements to produce erythema. The FST self-assessment test can be used to predict an individual's photosensitivity, placing the individual into one of six graduated categories. However, this phototype classification is based on responses to a series of questions (e.g., posed by a dermatologist or self-reported by the individual), which imposes some subjectivity that inherently causes a higher error index in comparison to objective MED data. In the home phototherapy and tanning market, for example, self-assessment of FST is done by selecting a skin type from Table 2 that best describes sunburn and tanning history. Data shows that there is a stepwise increase in the average MED from skin types I through VI, but although skin type and MED are correlated, there is a very wide range of MED values within each skin type and a substantial degree of overlap in the MED values among different skin types. Therefore, skin type alone may provide an indication of starting UVR dose range based on mean MED, but cannot serve as an absolute predictor of an individual patient's sensitivity to UV light. Other characteristics, such as hair color, skin color, eye color, number of freckles, sunburn propensity and suntan propensity have been tested and found similar or less predictive of MED than the original Fitzpatrick classification method. Historic tanning ability, sunburn susceptibility and untanned skin complexion have been shown to be more reliable predictors of MED. However, basing UV therapy dosage on questionnaires alone would result in sub-optimal treatment due to underdosing or overdosing many patients whose photosensitivity lies above or below the population mean. That is why, given the mean and standard distribution of MED for each skin type, adjustments are typically made by clinicians or by individual users based on erythema response to the starting dose for a given skin type.

TABLE 2

| Fitzpatrick Skin Type Self-Assessment | |
| --- | --- |
| Skin Type | Sunburn/Tanning History |
| I | Always burns, never tans; sensitive ("Celtic") |
| II | Burns easily, tans rarely |
| III | Burns moderately, tans gradually to light brown |
| IV | Burns minimally, always tans well to moderately brown (olive skin) |
| V | Rarely burns, tans profusely to dark brown (brown skin color) |
| VI | Never burns, deeply pigmented; not sensitive (black skin Fitzpatrick, TB., Arch. Dermatol., 124, 869, 1988. |

Clinically acceptable methods have been developed to determine the initial UVR dose for phototherapy devices. For example, dermatologic disorder phototherapy protocols include dose guidelines to help clinicians determine a suberythemal dose that may provide an efficacious outcome. Starting dose recommendations are based on a percentage of MED (50%-70%) or FST evaluation (clinician administered or self-assessment). The amount of exposure time needed to deliver a dose is calculated using measured irradiance of the phototherapy unit at the treatment position: Exposure Time (seconds)=Dose $(mJ/cm^2)$/Irradiance $(mW/cm^2)$. Because UVR sources have differing spectral compositions, different doses of total UV are needed to deliver the same erythemally-effective exposure. For MED-based dose guidance, the same UV spectrum used for phototherapy treatment is generally used for phototesting to establish relative comparison. As illustrated in Tables 3 and 4, for skin type-based recommendations, the spectral composition is defined as either broadband UVB (BBUVB) or narrowband UVB (NBUVB), and clinicians pick the appropriate starting dose based on the type of device and patient skin type. As shown in Table 5, starting doses for home phototherapy using NBUVB are reduced by over 50% from the clinical environment. For home phototherapy, the amount of time needed to deliver the dose is either calculated by the device when dose is entered into the interface or reference irradiance is provided for manual dose-time calculations. In some home devices, including cosmetic tanning beds, recommended exposure times are provided for each skin type, and the device timer is set without specified dose $(mJ/cm^2)$ information (e.g., as shown in Table 6).

TABLE 3

| Clinical BBUVB | |
| --- | --- |
| Skin Type | Initial UVB Dose $(mJ/cm^2)$ |
| I | 20 |
| II | 25 |
| III | 30 |
| IV | 40 |
| V | 50 |
| VI | 60 |

TABLE 4

| Clinical NBUVB | |
| --- | --- |
| Skin Type | Initial UVB Dose $(mJ/cm^2)$ |
| I | 300 |
| II | 300 |
| III | 500 |

TABLE 4-continued

| Clinical NBUVB | |
| --- | --- |
| Skin Type | Initial UVB Dose (mJ/cm$^2$) |
| IV | 500 |
| V | 800 |
| VI | 800 |

TABLE 5

| Home NBUVB Phototherapy | |
| --- | --- |
| Skin Type | Initial UVB Dose (mJ/cm$^2$) |
| I | 120 |
| II | 140 |
| III | 160 |
| IV | 180 |
| V | 200 |
| VI | 220 |

TABLE 6

| Home Cosmetic Tanning | | | | | |
| --- | --- | --- | --- | --- | --- |
| Skin Type | | Week 1 | Week 2 | Week 3 | More |
| I Sensitive | Burns easily & severely Does not tan | Tanning Not Advised | | | |
| II Light Skin | Burns easily & severely Tans minimally | 3 | 6 | 11 | 20 |
| III Normal Skin | Burns moderately Tans moderately | 5 | 9 | 15 | 20 |
| IV Dark Skin | Burns minimally Tans well/above | 7 | 12 | 18 | 20 |

Unlike dermatologic treatment, devices designed to stimulate cutaneous vitamin D do not have an established dosing method for initial dose. Although humans endogenously create previtamin D$_3$ when exposed to UVB, skin pigmentation is a major limiting factor governing that capacity. Because melanin absorbs UVB photons, it effectively reduces the amount of energy available for the photochemical transformation of 7-DHC to previtamin D$_3$. The doses required to produce erythema and vitamin D are correlated to each other and directly related to skin pigmentation. Lightly pigmented, photosensitive individuals require smaller UVR doses to produce both erythema and vitamin D. Conversely, photoresistant individuals have more pigment and require higher UVR doses to produce erythema and vitamin D. For example, full body exposure to a fixed dose of radiation capable of raising serum vitamin D$_3$ concentration by 10-fold in lightly pigmented individuals has been shown to produce a negligible increase in heavily pigmented subjects. These results are substantiated by human skin sample testing which has shown age-matched skin type II converts nearly 10 times more 7-DHC to previtamin D$_3$ than skin type V in a range of dosages. Researchers using increasing dosages of simulated sunlight on age-matched skin samples determined that the same maximum previtamin D$_3$ formation (15%) can be obtained in skin type VI as skin type III when using six times the dosage. Another study examined the effect of skin type adjusted dosage on vitamin D synthesis potential by measuring serum vitamin D3 concentration periodically for nine days after a single full body UVB exposure. Researchers established skin type classification and MED for a range of age-matched subjects (FST II to V) and then standardized dosage based on MED. While darker skin types required more radiation to achieve a similar erythemal response, there was no significant difference in serum vitamin D$_3$ concentration between subjects during the entire experiment.

Phototherapeutic devices and systems disclosed herein are configured to determine UVR doses within a therapeutic window that can significantly stimulate vitamin D production or treat dermatologic disorders, autoimmune disorders, and/or other indications, while reducing the likelihood of certain side effects (e.g., sun burn). It is expected that the therapeutic window for endogenous vitamin D exists from just below the minor sunburn threshold and extends down to the threshold for vitamin D synthesis. One study has shown that the in vivo threshold for vitamin D synthesis is approximately 50% of MED (0.5 MED) for full-body exposure. It has been demonstrated that doubling a therapeutic dose of UVB doubles the resultant peak serum vitamin D$_3$ concentration, even beyond MED. It has also been shown that the more skin surface is exposed to UVB radiation, the more D$_3$ is seen in the blood regardless of the body region of exposure. Therefore, the therapeutic window for cutaneous vitamin D synthesis with 75% skin exposure can be between 0.75 MED to 1 MED, well below the mild sunburn threshold (E$_2$). Thus, devices and systems disclosed herein can be configured to expose at least 75% of an individual's skin to UVR doses within a therapeutic window of 0.75 MED to 1 MED. In some embodiments, devices and systems in accordance with the present technology can expose greater or lesser percentages of the individual's skin, and the therapeutic window can be adjusted accordingly.

Various embodiments of the present technology can also regulate the frequency of phototherapy treatment to avoid overexposure and underexposure. Different intervals of time between treatments may be needed depending on the indication, regulatory restrictions set by governing agencies (e.g., FDA, Health Canada), and treatment protocol. For example, UVB phototherapy for psoriasis treatment usually consists of three exposures per week for at least three months, and then a frequency of once every one to two weeks is used for maintenance. For endogenous vitamin D, thermal isomerization of pre-vitamin D3 to vitamin D3 typically take three days to complete, and photodegradation of cutaneous vitamin D3 prior circulation transfer means repeated treatments within this three-day window would be counterproductive. Additionally, the cutaneous translocation of vitamin D3 to circulation can take seven or more days to complete. Therefore, treatment regimens designed to stimulate endogenous vitamin D to treat or prevent vitamin D deficiency can be more frequent (e.g., every three days) at the beginning to address an acute need (treatment) and less frequent (e.g., every seven days) after one or more months (e.g., 2 months, 3 months, etc.) to provide efficiency of conversion for maintenance dosing (prevention). However, dosing regimens for devices designed to stimulate cutaneous vitamin D have not been established.

The skin is known to acclimatize with frequent UV exposures and becomes significantly less sensitive to sunburn, requiring increased dose to induce erythema, immune response, melanogenesis or vitamin D synthesis. Photoadaptation is caused by facultative pigmentation (melanogenesis), which is driven primarily by UVA, and epidermal hyperplasia (epidermal thickening), which is caused mostly by UVB. The amount of erythema protection (photoadaptation) provided by UVB exposure is greater than UVA because the increase in keratins leads to stronger UVB absorption (the primary driver of erythema) than facultative pigmentation. For example, photoadaptation during BBUVB phototherapy has been shown to increase MED to a plateau of 800% over initial MED within eight weeks of treatment without hyperpigmentation and is independent of FST (constitutive pigmentation). In contrast, using tanning devices, which typically emit 5% UVB and 95% UVA, for 3 treatments per week for three weeks increased pigmentation significantly, but MED increased to only 300% over initial MED. The photoadaptation caused by NB-UVB phototherapy treatments are considerably less (e.g., final MED=2.7× initial MED) than that reported for BB-UVB and comparable to tanning devices. While there is no clear consensus on degradation of photoadaptation from different UVR sources (UVB/UVA composition), elevated MED from sunlight acclimatization has a duration of about one to two months before returning to initial MED levels. It is expected that photoadaptation degradation is linear with time and has different slopes based on the spectral output of the UVR source. As shown in Tables 7 and 8, recommendations for dose increases to compensate for photoadaptation have been developed for BBUVB and NBUVB when repeating treatment more often than once every four days. In addition, as further shown in Tables 7 and 8, dose reduction recommendations for BBUVB and NBUVB phototherapy have been developed to account for photoadaptation degradation, although no such recommendation is used for cosmetic tanning devices. As with initial dosing, devices designed to stimulate cutaneous vitamin D do not have an established dosing method to account for photoadaptation.

TABLE 7

Clinical BBUVB Phototherapy

| Skin Type | Amount of UVB Increase (mJ/cm$^2$) |
|-----------|------------------------------------|
| I | 5 |
| II | 10 |
| III | 15 |
| IV | 20 |
| V | 25 |
| VI | 30 |
| 4-7 days | Keep dose the same |
| 1-2 weeks | Decrease dose by 50% |
| 2-3 weeks | Decrease dose by 75% |
| >3 weeks | Start over |

TABLE 8

Clinical NBUVB Phototherapy

| Skin Type | Amount of UVB Increase (mJ/cm$^2$) |
|-----------|------------------------------------|
| I | 100 |
| II | 199 |
| III | 125 |
| IV | 125 |
| V | 150 |
| VI | 150 |
| 4-7 days | Keep dose the same |
| 1-2 weeks | Decrease dose by 25% |
| 2-4 weeks | Decrease dose by 50% |
| >4 weeks | Start over |

In addition to the aforementioned factors weighing into dosage, research has shown that age and gender have a statistically significant influence on MED. One study of over 300 people indicated that mean MED is 18% lower in males than females, and that MED decreases with age at a rate of roughly 0.4% per year starting from age 5. In addition, for some phototherapy treatments like endogenous vitamin D, physical characteristics such as Body Mass Index (BMI), gender and age can affect the efficacy of treatment. BMI is negatively correlated with both serum 25(OH)D3 and 1,25 (OH)2D3. It has also been shown that the serum D3 increase after UVB phototherapy is inversely correlated to BMI. It is thought that fat-soluble vitamin D is captured by adipose tissue making it less bioavailable for those with higher BMI. Males have higher serum 25(OH)D3 than females and this association still exists when controlling for BMI. From age 18 to 80, there is a 50% reduction in epidermal 7-DHC concentration available for conversion to previtamin D3. The linear decrease of cutaneous 7-DHC with age reduces the vitamin D synthesis potential of the elderly and is considered the primary driver of age related 25(OH)D decline. Accordingly, devices and systems disclosed herein can determine treatment protocols that adjust dose or frequency for endogenous vitamin D phototherapy treatment to compensate for BMI, gender and age-related reductions in vitamin D needs or response.

Selected Embodiments of Dynamic Dosing Devices, Systems, and Methods for Phototherapy The technology presented here is directed to the apparatuses, systems, and methods for an automated dynamic dosing system for delivering safe and effective self-care phototherapy treatment. Many of the embodiments are described below with respect to systems, devices, and methods for self-service phototherapy kiosk ("SPK") dynamic dosing system operations. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to Figures.

FIG. 1 is an isometric view of a dynamic dosing phototherapy system 100 (also referred to as the "phototherapy system 100") configured in accordance with embodiments of the present technology. As shown in FIG. 1, the phototherapy system 100 includes an SPK 104, one or more interfaces 102 (identified individually as first through third user interfaces 102a-c, respectively) for receiving using inputs and communicating information to users of the phototherapy system 100, and a dynamic dosing system 105 (shown schematically; also referred to as the "SPK dynamic dosing system 105" or the "SPK dosing system 105") for dynamically determining the user-specific dosage based on user inputs. The user interfaces 102 can be integrated into the SPK 104 or communicatively coupled thereto. The dynamic dosing system 105 can be a system stored locally at the SPK 104 and/or a remote system operatively coupled the SPK 104, other SPKs in the phototherapy system 100, and the user interfaces 104. The SPK 104 includes a UV radiation assembly 106 for delivering UV radiation-based phototherapy, such as a light panel including one or more UV radiation assemblies configured to emit UV radiation within a predetermined wavelength spectrum (e.g., within the UVB range). Suitable configurations UV radiation assemblies and configurations are disclosed in U.S. patent application Ser. No. 13/733,860, filed Jan. 3, 2013, titled "PHOTOTHERAPEUTIC APPARATUS FOR FOCUSED UVB RADIATION AND VITAMIN D SYNTHESIS AND ASSOCIATED SYSTEMS AND METHODS," and PCT Patent Application No. PCT/US2017/054578, filed Sep. 29, 2017, titled "PHOTOTHERAPEUTIC SYSTEMS INCLUDING SPREADING AND COLLIMATING FEATURES AND RELATED TECHNOLOGY," both of which are incorporated herein by reference in their entireties.

The SPK 104 can include a housing 108 that creates a booth-like structure for completely or partially encloses a chamber 110. The chamber 110 can be sized to comfortably contain a human user in a standing, sitting, and/or supine position (e.g., similar to a tanning bed). In some embodiments, the chamber 110 is sized to receive only a portion of a human body, such as the face, head, torso, legs, and/or other portions of the human body. In some embodiments, the SPK 104 includes a door 112 that completely encloses the chamber 110 and, optionally, locks so that users have a private and secure environment to disrobe for treatment. In some embodiments, the SPK 104 is configured in a manner that reduces or minimizes skin-to-device contact for improved sanitation. In operation, the UV radiation assembly 106 can emit phototherapeutic UV radiation toward a phototherapy zone 111 within the chamber 110.

As shown in FIG. 1, the SPK 104 can include an integrated eyewear dispenser 114 that is operated by one of the user interfaces 102 (e.g., the first user interface 102a within the chamber 110). The eyewear dispenser 114 can provide protective eyewear is to prevent eye damage from optical radiation emitted by the UV radiation assembly 106.

In some implementations, the SPK 104 can have a lighting component 116 (e.g., LED lighting) that can be adjusted based on stages of use, communication emphasis, entertainment, and/or user interaction. For example, the lighting component can be configured to adjust the color, lighting level, illumination patterns, effects, and/or other lighting parameters to provide visual signals to the user before, during, and/or after phototherapy.

In various implementations, the SPK 104 can have one or more of: an emergency stop control 118, a seating component 120 (e.g., a bench) within the chamber 110, one or more positioning indicators 122 (e.g., imprinted footprints) for guiding the user to the proper position relative to the UV radiation assembly 106, a mirror 124, and/or other features for operating or enhancing performance of the SPK 104.

In the illustrated embodiment, the first user interface 102a is positioned in the interior of the housing 108 and accessible from within the chamber 110, whereas the second user interface 102b is positioned on and accessible vie the exterior of the housing 108. The third user interface 102c is a mobile application that is accessible via a mobile device 126 (e.g., a smartphone, tablet, personal computer) communicatively coupled to the phototherapy system 100. In other embodiments, the SPK 104 may only have one user interface 102, more than two user interfaces, and/or the user interfaces of the SPK 104 may be omitted in favor of remote user interfaces, such as the third user interface 102c.

As shown in FIG. 1, the first user interface 102a comprises a touchscreen or monitor with menu options having touch-sensitive display fields and/or buttons for entering and displaying run parameters and program information. Pressing a "start" or other type of initialization button on the first user interface 102a, providing verbal command, and/or selecting a menu option on the first user interface 102a causes the first user interface 102a to display one or more additional graphical user interfaces ("GUIs"), thereby allowing the user to enter or select more information. The first user interface 102a interfaces with and is controlled by a user to operate the SPK 104 during a phototherapy session, and provides step-by-step instructions to help guide the user through the entire treatment process. For example, the first page or GUI displayed on the first user interface 102a allows users to select a language that will be used for written and audio content for the remaining screens in the process. In some embodiments, the second user interface 102b on the exterior of the SPK 104 and/or the third user interface 102c (e.g., a smartphone application), which is accessible via the user's personal device and communicatively connected to the SPK 104 via a network connection, can be used to perform the same, similar or additional functions as the first user interface 102a. Information gathered from the user by any of the user interfaces 102 can be stored locally at the SPK 104 and/or in a network database cloud to use at any networked SPK 104. For example, the one or more user interfaces 102 can receive information related to the user's date of birth, gender, body weight, BMI, skin tone, Fitzpatrick skin type answers, hair color, eye color, number of freckles, propensity to sunburn, propensity to suntan, indication for use, and/or other parameters that may affect the treatment protocol. This information can be stored in the cloud and/or another remote database, and used by the dynamic dosing system 105 to determine the user's skin type category, MED estimate, starting or initial dose, treatment frequency, dose increases, dose decreases, long-term treatment pattern, and/or other information relevant to phototherapy treatments. Information received by the one or more user interfaces 102 about phototherapy treatment response (e.g., erythema, skin color change, discomfort, peeling, blisters, rash, disease symptoms, and/or mood change) can be stored in the cloud and used by the dynamic dosing system 105 to determine adjustments to skin type category, MED estimate, dose, treatment frequency, dose increases, dose decreases, and long-term treatment pattern.

Thus, in operation, the phototherapy system 100 can gather information that can be used to determine the correct initial radiation dose for an individual user based on user-specific metrics, formulate a user-specific treatment protocol for a phototherapy session delivered via the SPK 104, and cause the SPK 104 to carry out the treatment protocol. After the user has undergone one or more phototherapy sessions, the phototherapy system 100 can analyze user response to the one or more phototherapy sessions as well as other factors that may affect treatment protocols for subsequent phototherapy sessions to adjust the treatment protocol such that it is suitable for the user at the user's current state (i.e., after one or more phototherapy sessions). In some embodiments, the phototherapy system 100 can also use the initial dose determination and/or adjusted dose determinations to automatically devise different treatment protocols for multiple different SPKs based on the features and detected specifications of each SPK. For example, the phototherapy system 100 can receive information regarding operational characteristics of each SPK via manual inputs, detected identifiers (e.g., barcodes, QR codes, and/or other electronically detectable identifiers that identify SPKs or portions thereof), and/or sensors (e.g., coupled to radiation sources to determine operating parameters). These operational characteristics can include, for example, the size of irradiation zone, proximity between the user's skin and the irradiation panel, intensity or other parameters associated with the radiation assemblies, operating parameters of individual radiation sources (e.g., to account for newly installed radiation sources potentially having higher outputs than ones near the end of their shelf life), and/or other characteristics of the SPK. This information can then be used to automatically customize a treatment protocol based on the user-specific dose and the specific parameters of the SPK to increase efficiency and effectiveness of the overall phototherapy session.

Phototyping

The SPK dosing system 105 of the phototherapy system 100 can receive and analyze numerous parameters when automatically determining a user's initial or base radiation dose. One such factor is the erythema propensity of the users' skin, also referred to as photosensitivity. Photosensitivity of the user is associated with six skin type categories: the first skin type being the most photosensitive and the sixth skin type being most photo-resistant. To determine the user's photosensitivity, one of the user interfaces 102 (e.g., the first user interface 102a on the interior of the SPK 104) can present a series of self-assessment questions to the user that can be scored via the phototherapy system 100 to allow skin type classification and adjustment according to an adjustable algorithm initiated locally at the SPK 104 and/or remotely on a central processor communicatively coupled to the SPK 104. In some embodiments, a single question can be used for simplicity, and in other embodiments multiple questions can be used to enhance accuracy and precision. The questions presented to the user via the user interface 102 may be related to Fitzpatrick skin typing, skin tone, hair color, eye color, number of freckles, propensity to sunburn, propensity to suntan, and/or other characteristics indicative of photosensitivity.

Questions directed to Fitzpatrick skin typing can be designed to capture user response to one hour of noon summer solstice sunlight. For example, the question can be: with no base tan, what is your skin response to 1 hour of noon summer sun? The answers provided on the user interface 102 can include: I will have a painful burn 24 hours later and no tan in 7 days; I will have a tender burn 24 hours later and a light tan in 7 days; I will have a slightly tender burn 24 hours later and a moderate tan in 7 days; and I will have no burn 24 hours later and a good tan in 7 days.

In some embodiments, the Fitzpatrick skin typing question can be broken down into two or more questions in response to a scenario presented to the user. For example, the initial question may be: after several months of not being in the sun, what would happen to your skin if you stayed in direct sun for 1 hour at noon for the first time in the summer without sunscreen, would you have a sunburn one day later, and/or would you have a suntan one week later? The proposed answers provided can include: always sunburn, usually sunburn, probably sunburn, maybe sunburn, rarely sunburn, never sunburn, never-none, rarely-minimal, maybe-moderate, probably-noticeable, usually-slightly noticeable, and already dark-no noticeable change.

Figures 2, 3:
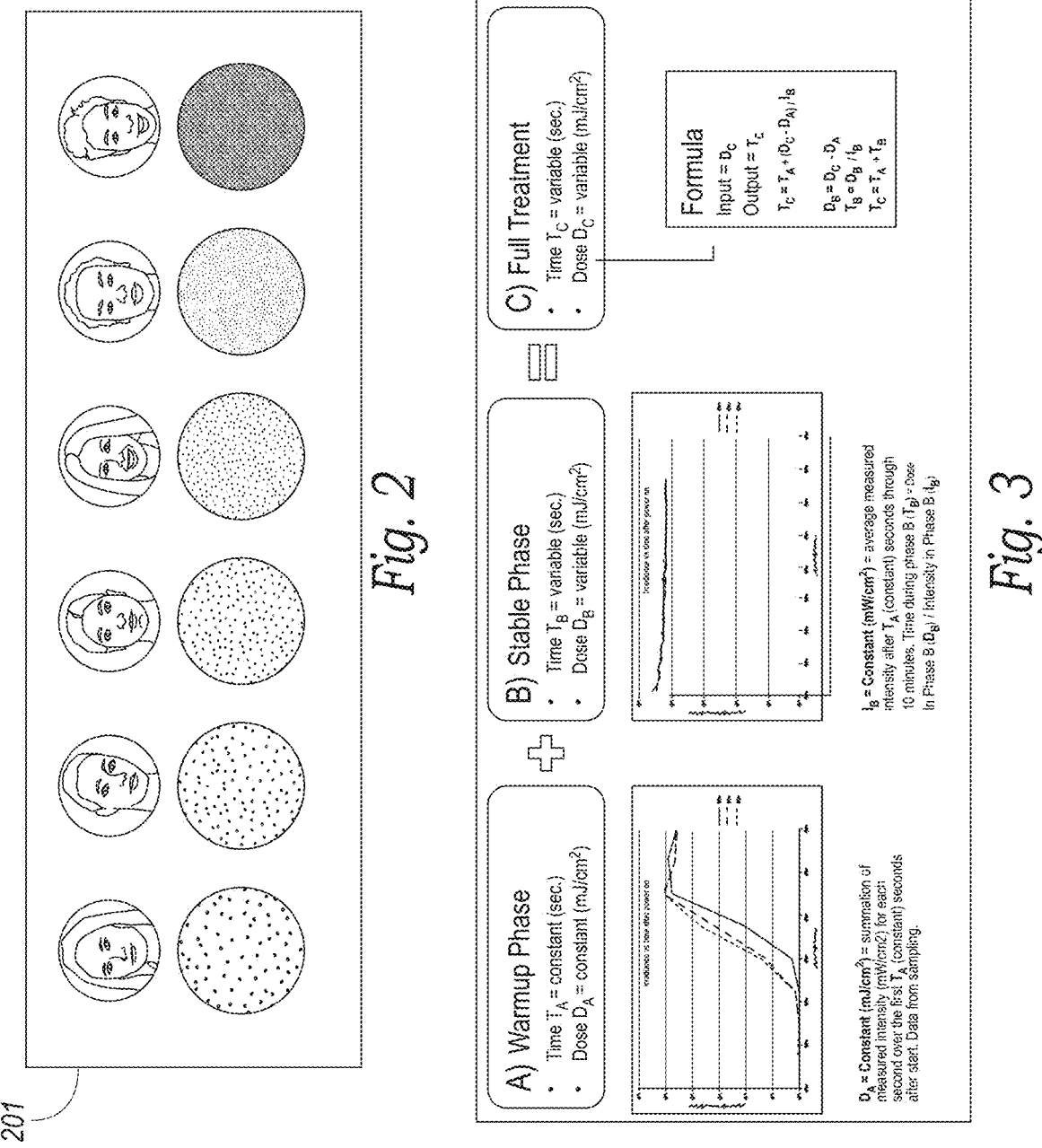
FIG. 2 illustrates a skin tone selection graphical user interface ("GUI") configured in accordance with embodiments of the present technology.
FIG. 3 illustrates a method of determining dose time for phototherapy protocols using phototherapy systems configured in accordance with embodiments of the present technology.

Questions directed to skin tone can be displayed to users visually with color swatches and/or facial photographs of archetypical characteristics that normally are associated with the skin type categories. FIG. 2, for example, illustrates such a skin tone selection GUI 201 configured in accordance with embodiments of the present. As shown in FIG. 2, people with skin type 1 (most sensitive) usually have light eyes (blue or green) and hair (blond or red), frequently have many freckles, and pinkish pale skin. On the other end of the spectrum, people with skin type 6 normally have very dark eyes (black or dark brown) and hair (black or dark brown), no freckles, and dark brown or black skin. Choosing photographs with these characteristics can increase accuracy of a single skin tone question by allowing users to self-categorize other related characteristics. Using photographs can allow this single question to be used to establish skin type category without other questions. In some embodiments, this question can have photographs without skin tone swatches. In other embodiments, skin tone answers can be described verbally through a speaker or with written description, of untanned skin town such as pinkish pale, pale, moderate pale, moderate dark, dark, or very dark.

In some embodiments, the user interface 102 can present questions related to hair color to assess skin type and photosensitivity. Because skin pigmentation is directly correlated hair pigmentation, a question related to hair color is designed to estimate melanin concentration in the skin from darkness of natural hair color. In some embodiments, examples (e.g., photos or graphics) of a spectrum of hair color from light to dark can be presented on the user interface 102 with or without written description. In some embodiments, only written (or auditory) description is used. The hair color question(s) can be asked in different ways and have a range of answers. For example, the question(s) may include one or more of the following: what is your natural hair color, what was the color of your natural scalp hair as a teenager, and/or how dark was your natural scalp hair as a teenager? The answers provided to the user via the user interface 102 may include the following: very light or red-light blond, light or blond-light brown, moderate or dark blond-brown, medium dark or brown-dark brown, dark or dark brown-black, and/or very dark or black.

In some embodiments, the user interface 102 can present questions related to eye color to assess skin type and photosensitivity. Because skin pigmentation is directly correlated eye pigmentation, the eye color question is designed to estimate melanin concentration in the skin from darkness of natural eye color. In some embodiments, examples (e.g., photos or graphics) of a spectrum of eye color from light to dark can be presented on the user interface 102 with or without written description. In some embodiments, only written and/or auditory descriptions are used. The eye color question can be asked to determine eye lightness or color and have a range of answers. For example, the eye color question(s) may include: what is your natural eye color, or how dark is your natural eye color? The answers provided to the user via the user interface 102 may include the following: very light or light blue-light green, light or blue-green-light hazel, moderate or dark blue-dark green-hazel-light brown, medium dark or dark hazel-brown, dark or dark brown-black, and very dark or black.

In some embodiments, the user interface 102 can present questions related to freckles to assess skin type and photosensitivity. Having freckles at a young age or having many freckles is correlated lower MED. Thus, freckle-related questions are designed to distinguish lighter skin types from darker ones by estimating number of freckles. In some embodiments, examples (e.g., photos or graphics) of a patch of skin with a spectrum of different freckle concentrations from many to none can be presented to the user via the user interface 102 with or without written description. In some embodiments, only written or auditory descriptions are used. The freckle-related question(s) can be asked with a yes or no response and/or with a range of answers. For example, the freckle-related question(s) may include: did you have freckles at 10 years old, how many freckles do you have on your body, and/or what percentage of your body skin contains freckles? The answers provided to the user via the user interface 102 may include the following: many or 75-100%, several or 50-75%, some or 25-50%, few or 1-25%, and none or 0%.

In some embodiments, the user interface 102 can present questions related to the user's propensity to sunburn to assess skin type and photosensitivity. Self-reported sunburn propensity is correlated to MED. The sunburn-related question(s) can be asked in different ways and have a range of answers. For example, sunburn-related questions may include: how easily do you sunburn in midday summer sun without sunscreen, and how easily do you sunburn? The answers may include: very easily, easily, moderately, minimally, rarely, and never.

In some embodiments, the user interface 102 can present questions related to the user's propensity to suntan to assess skin type and photosensitivity. Self-reported suntan potential is correlated to MED. The suntan-related question(s) can be asked in different ways and have a range of answers. For example, suitable suntan-related questions include: how easily does your skin suntan, how tan can you get after one week of daily summer sun, or how long does it take for you to build a good suntan in summer sunlight? Suitable answers to address these questions may include: (a) never, none, very long-never; (b) minimally, light, 10+ days; (c) moderately, moderate, or 5-9 days; (d) easily, dark, or 3-4 days; (e) very easily, very dark, or 1-2 days; and (f) difficult to notice.

The phototherapy system 100 can receive answers via the user interface 102 and/or other device to the questions related to the user's Fitzpatrick skin type, skin tone, hair color, eye color, freckle, propensity to sunburn, propensity to suntan, and/or other photosensitive-related inquiries, and the processor can use these answers to questions to automatically prescribe the user's skin type, the starting/baseline dose, and/or MED prior to phototherapy treatment. The received answers can also be used to analyze against treatment response to create algorithms that can better predict MED using machine learning.

Each answer can be weighted in correlation with skin types one through six. In some embodiments, such as many of the examples described above, the answer sets are provided on a six-point scale designed to correspond with the six skin types (e.g., two points would be assigned to the second answer and correspond to skin type two characteristics). However, answer sets include fewer than six answers, and be divided evenly between six skin types (e.g., answers 1-5 are scored as 1, 2.25, 3.5, 4.75, and 6, respectively). Some answers can be weighted differently so that some characteristics provide a stronger or weaker influence on the overall scoring of multiple questions (e.g., answers 1-6 can be scored as 1, 1.5, 2.5, 3.5, 6, and 8, respectively). Some entire questions can be weighted differently so that they provide a stronger or weaker influence on the overall scoring of multiple questions. For example, the answer to a question can be multiplied by 0.5 to provide half the influence on the overall score or multiplied by two to impart twice the influence on the overall score as normal baseline scored questions. Some questions can be combined with a conditional statement that creates a single answer (or point value) that is not a summation of the questions separately. Answers to questions can be scored to provide a range of point totals that are placed into one of six skin type buckets (e.g., the Fitzpatrick system) that can provide six MED estimates and six starting dosages that correspond to the six skin types. In other embodiments, the scoring of answers can provide a higher resolution skin type, such as 1-100 or 1.0-6.0 with an equally high resolution of MED estimates and starting dosages. The following are some examples of scoring formulas that lead to a skin type (ST) value:

1. Two questions (Q1, Q4) with logic to determine ST 1 to 6:
   a. If Q1=A1 then ST=1
   b. Else if Q1=A2 then ST=2
   c. Else if Q1=A3 then ST=3
   d. Else if Q1=A4 then
      i. If Q4<=4 ST=4
      ii. If Q4=5 ST=5
      iii. If Q4=6 ST=6

2. Two questions (Q1, Q4) with logic to determine ST 1 to 6:
   a. If Q1=A1 then ST=1
   b. Else if Q1=A2 or A3 then
      i. If Q4 value <Q1 value then ST=Q4 value
      ii. Else ST=Q1 value
   c. Else if Q1=A4 then ST=Q4 answer (A1-A6)
      i. If Q4=1 then ST=1
      ii. If Q4=2 then ST=2
      iii. If Q4=3 then ST=3
      iv. If Q4=4 then ST=4
      v. If Q4=5 then ST=5
      vi. If Q4=6 then ST=6
3. Single question (Q4) scoring based on skin color pictures and swatches with each answer having the same point value as the answer number (i.e. A4=4 points).
   a. ST=Q4 Answer (1-6)
4. Multiple questions with equal weight scoring rounded to the nearest integer (ST 1-6) or decimal (i.e. 2.5 instead of 2 or 3) with each answer having the same point value as the answer number, except Q7 where A1=1 point and A2=4 points.
   a. ST=(Q1 value+Q4 value)/2
   b. ST=(Q2 value+Q3 value)/2
   c. ST=(Q9 value+Q10 value)/2
   d. ST=(Q2 value+Q3 value+Q4 value)/3
   e. ST=(Q4 value+Q9 value+Q10 value)/3
   f. ST=(Q1 value+Q4 value+Q7 value)/3
   g. ST=(Q1 value+Q4 value+Q8 value)/3
   h. ST=(Q4 value+Q7 value+Q9 value+Q10 value)/4
   i. ST=(Q4 value+Q8 value+Q9 value+Q10 value)/4
   j. ST=(Q4 value+Q5 value+Q6 value+Q7 value+Q9 value+Q10 value)/6
   k. ST=(Q4 value+Q5 value+Q6 value+Q8 value+Q9 value+Q10 value)/6
   l. ST=(Q2 value+Q3 value+Q4 value+Q5 value+Q6 value+Q7 value)/6
   m. ST=(Q2 value+Q3 value+Q4 value+Q5 value+Q6 value+Q8 value)/6
5. Multiple questions with scoring rounded to the nearest integer (ST 1-6) or decimal and at least one question that conditionally adjusts the formula by increasing/reducing the number of questions for scoring.
   a. If Q7=A1 then ST=(Q1 value+Q4 value+1)/3
      i. Else ST=(Q1 value+Q4 value)/2
   b. If Q7=A1 then ST=(Q2 value+Q3 value+Q4 value+1)/4
      i. Else ST=(Q2 value+Q3 value+Q4 value)/3
   c. If Q7=A1 then ST=(Q4 value+Q9 value+Q10 value+1)/4
      i. Else ST=(Q4 value+Q9 value+Q10 value)/3
   d. If Q4=A6 then ST=(Q4 value+Q9 value)/2 or ST=(Q4 value+Q2 value)/2
      i. Else if Q4=A5 then ST=(Q4 value+Q9 value)/2 or ST=(Q4 value+Q2 value)/2
      ii. Else ST=(Q4 value+Q9 value+Q10 value)/3 or ST=(Q4 value+Q2 value+Q3 value)/3
   e. If Q4=A6 and Q7=A1 then ST=(Q4 value+Q9 value+1)/3 or ST=(Q4 value+Q2 value+1)/3
      i. Else if Q4=A6 and Q7=A1 then ST=(Q4 value+Q9 value+1)/3 or ST=(Q4 value+Q2 value+1)/3
      ii. Else ST=(Q4 value+Q9 value+Q10 value)/3 or ST=(Q4 value+Q2 value+Q3 value)/3

Individual MPE, MED, and Starting Dose

The phototherapy system 100 uses skin type (e.g., assessed as discussed above) to estimate a starting dose by using the mean MED for each skin type derived from cross-sectional studies and/or other previous data that determined individual MED related to skin type classification. To normalize different UVR sources having spectral variations, the CIE Erythemal Action Spectrum can be used to calculate biologically effective erythema doses that are relevant for all UVR sources. Studies were initially conducted with 70 subjects to investigate CIE weighting MED categorized by skin type. Using this data, the mean MED per skin type was determined, as well as a high and low range in which the true mean for each group is likely to occur. These mean MED-CIE weighted doses for each skin type are shown in Table 9. In some embodiments of the technology, the SPK 104 can be configured to select and deliver a starting dose based on the range of starting doses shown in Table 9 that corresponds to user's skin type (determined via the question-answer algorithm discussed above). In some embodiments, the SPK can be set to deliver a starting dose that is a percentage less than the low MED, middle MED, or high MED dose per skin type shown in Table 9 (e.g., 0.95MED, 0.90MED, 0.85MED, 0.75MED, 0.70MED, 0.65MED, 0.60MED, 0.55MED, 0.50MED, etc.).

TABLE 9

| Mean MED Range Per Skin Type CIE Weighted Dose (mJ/cm²) | | | |
| --- | --- | --- | --- |
| Skin Type | Low | Middle | High |
| I | 20 | 22 | 24 |
| II | 28 | 33 | 38 |
| III | 30 | 35 | 40 |
| IV | 39 | 45 | 51 |
| V | 60 | 80 | 100 |
| VI | 67 | 87 | 107 |

The inventors' research determined that the MPE/MED ratio for all skin types as 0.70 (standard deviation=0.087). Therefore, 0.7 mean MED is the threshold dose needed to provide barely perceivable erythema in the majority of individuals within each skin type. Table 10 provides a list of dosage points with high, middle, and low doses to prevent MPE according to the mean MED for each skin type (i.e., $MPE_{Middle}=MED_{Middle}*MPE/MED$ ratio, $MPE_{Low}=MED_{Low}*(MPE/MED$ ratio–ratio SD), $MPE_{High}=MED_{High}*(MPE/MED$ ratio+ratio SD)).

In some embodiments of the technology, the SPK 104 can be set to deliver a starting dose corresponding to the ranges shown in Table 10 for the user's skin type. In some embodiments, the SPK 104 can be set to deliver a starting dose that is percentage less than the low MPE, middle MPE, high MPE dose per skin type in Table 10 (e.g., 0.95MPE, 0.90MPE, 0.85MPE, 0.75MPE, 0.70MPE, 0.65MPE, 0.60MPE, 0.55MPE, 0.50MPE, etc.).

TABLE 10

| Mean MPE Range Per Skin Type CIE Weighted Dose (mJ/cm²) | | | |
| --- | --- | --- | --- |
| Skin Type | Low | Middle | High |
| I | 12.3 | 15.4 | 18.9 |
| II | 17.2 | 23.1 | 29.9 |
| III | 18.4 | 24.5 | 31.5 |
| IV | 23.9 | 31.5 | 40.1 |
| V | 36.8 | 56 | 78.7 |
| VI | 41.1 | 60.9 | 84.2 |

In some embodiments, the phototherapy system 100 can have an SPK dosing system designed to deliver a standard starting dose between the low MPE and high MED value for each skin type regardless of other characteristics. For example, when a user's actual individual MPE ($MPE_i$) and individual MED ($MED_i$) is unknown, the system 100 can be configured to automatically apply a starting dose between the low MPE and high MED, and continue to apply doses within this range until the user provides erythema feedback (e.g., after one or more phototherapy sessions).

In some embodiments, the SPK dosing system can factor in the user's age and/or gender to better estimate or adjust individual $MED_i$, $MPE_i$, and the skin type based starting dose. Table 11, for example, illustrates metrics for how age and gender can be incorporated into the dosing algorithm to adjust the starting dose.

TABLE 11

| MED/MPE/Starting Dose Adjustment | | |
| --- | --- | --- |
| Characteristic | Reason | Adjustment |
| Gender | Photosensitivity | Male = −18% (−1% to −25%) |
| Age | Photosensitivity | Age over 18 = −0.4% per year (−0.1% to −0.7%) |
| Gender | Vitamin D | Female = +20% (+1% to +25%) |
| Age | Vitamin D | Age over 18 = +0.8% per year (+0.1% to +1.5%) |
| BMI | Vitamin D | BMI over 18 = +1.0% per point (+0.1% to +2.0%) |

More specifically, the SPK dosing system can estimate individual MED ($MED_i$), individual MPE ($MPE_i$), and/or individual starting dose ($SD_i$) based on the user's skin type, age, and gender in accordance with the formulas below, where FM=1 for male gender and FM=0 for female gender:

$$MED_i=(MED_{Mean}+(MED_{Mean}*Male*-0.18))+\\((MED_{Mean}+(MED_{Mean}*Male*-0.18))*((Age-18)*-0.004))$$

$$MPE_i=(MPE_{Mean}+(MPE_{Mean}*FM*-0.18))+\\((MPE_{Mean}+(MPE_{Mean}*F\qquad M*-0.18))*\\((Age-18)*-0.004))$$

In some embodiments, the SPK dosing system can be configured to estimate $MED_i$, $MPE_i$, and 0.90 $MPE_i$, for $SD_i$, using the middle values illustrated in tables 9 and 10. In this embodiment, for example, an 18-year-old female skin type 3 would have a calculated $MED_i$ of 35 mJ/cm², $MPE_i$ of 24.5 mJ/cm², and $SD_i$, of 22.1 mJ/cm². Using the same configuration, a 45-year-old male user with skin type 3 would have base values multiplied by −18% for male gender adjustment and then −10.8% for age adjustment, resulting in an estimated $MED_i$, of 25.6 mJ/cm², and MPEi of 17.9 mJ/cm², and $SD_i$ of 16.1 mJ/cm².

In some embodiments, the SPK dosing system can determine estimated individual MED ($MED_i$), individual or MPE ($MPE_i$), and individual starting dose ($SD_i$) based on skin type and age only using the following formulas:

$$MED_i=(MED_{Mean}+(MED_{Mean}*(Age-18)*-0.004)$$

$$MPE_i=(MPE_{Mean}+(MPE_{Mean}*(Age-18)*-0.004)$$

For example, the SPK dosing system can be configured to estimate $MED_i$, $MPE_i$, and $0.85MPE_i$ for $SD_i$, using the high values of Tables 9 and 10. In this configuration, for example, a 45-year-old male/female user with skin type 4 would not have gender adjustment, but would have base values multiplied by $-10.8\%$ for age adjustment, resulting in an estimated $MED_i$ of 45.5 mJ/cm$^2$, MPEi of 35.8 mJ/cm$^2$, and $SD_i$ of 30.4 mJ/cm$^2$.

Photosensitivity Screening Dose (PSD)

In various embodiments, the phototherapy system 100 can deliver a photosensitivity screening dose (PSD) for a first treatment that is about 30% to 70% lower than the individual starting dose ($SD_i$) (determined in accordance with the algorithms described above). Thus, if the phototherapy system 100 is configured to deliver a PSD of 60% lower than the starting dose, $PSD=0.60(SD_i)$.

The SPK 104 can be configured to delivery a PSD before a true therapy session and before determining a true SDi to identify users that have an actual MED that is 2 to 3 standard deviations more photosensitive than the mean MED for a skin type. Without such a screening dose, photosensitive individuals that have an actual MED of <30% of the skin type mean MED are likely to have an E2 or E3 erythemal event after receiving a UVR therapy near the mean MED for the assessed skin type. Thus, by applying a screening dose during the first treatment, abnormal erythema response can be detected near the erythemal threshold (MPE, MED) of an E1 event, thereby avoiding E2 or E3 erythemal events in these individuals. After the screening dose session, the user can provide feedback via the user interface to provide an assessment of the user's erythemal response to the screening dose. Taking into account this information, the phototherapy system 100 can adjust the MPEi and MEDi estimates down for that individual (if appropriate), and store this information with the corresponding user account on a remote database so subsequent doses can reflect that photosensitivity to prevent future erythemal events. For most users, the screening dose will be far below the actual MEDi for that individual and the starting dose (SDi) can be delivered during the second treatment. However, in some embodiments of the technology, a second screening dose can be provided that is halfway between the first screening dose and the calculated starting dose SDi for that skin type to further refine the SDi. For example, the calculated SDi for a user may be 40 mJ/cm2 with a PSD of 20 mJ/cm2 (50% of starting dose) delivered by the SPK 104 during the first treatment. If the user reports no erythema response, then the second SPK treatment can be configured to deliver a second PSD of 30 mJ/cm2 (75% of starting dose). If the user reports no erythema response, then the third treatment is given at the initial SDi of 40 mJ/cm2. In further embodiments, more than two screening doses can be delivered via the SPK 104 to further refine the SDi to avoid erythemal responses.

Individual Treatment Dose (TDi)

The phototherapy system 100 can also be configured to assess an individual treatment dose ($TD_i$), which is the dose that an individual user should receive for a treatment with no consideration of modifications for photoadaptation, medication use, or recent UV exposure. During a first phototherapy treatment, the $TD_i$ should be equal to the calculated $SD_i$ or PSD as previously described. After initial treatments, $MPE_i$ and $MED_i$ may change or stay the same depending on erythema response feedback provided by the user. Like $SD_i$ the $TD_i$ is based on a percentage of $MPE_i$ or $MED_i$. Where $SD_i$ is calculated using $MPE_{Mean}$ or $MED_{Mean}$, $TD_i$ is calculated similarly as a reduction factor ($R_f$) percentage of $MPE_i$ (e.g., $0.95MPE_i$, $0.90MPE_i$, $0.85MPE_i$, $0.75MPE_i$, $0.70MPE_i$, $0.65MPE_i$, $0.60MPE_i$, $0.55MPE_i$, $0.50MPE_i$, etc.) or $MED_i$, (e.g., $0.95MED_i$, $0.90MED_i$, $0.85MED_i$, $0.75MED_i$, $0.70MED_i$, $0.65MED_i$, $0.60MED_i$, $0.55MED_i$, $0.50MED_i$, etc.). For example, the SPK 104 can be set up to deliver a dose of UVR to all users that is 90% of individual MPE, and therefore $TD_i$ would be determined as follows: $TD_i=R_f*MPE_i$ or $TD_i=0.90(MPE_i)$. In other embodiments, the phototherapy system 100 can impart different reduction factors based on different indications for use. For example, the phototherapy system 100 can determine individual treatment doses for dermatologic disorders based on the following formula: $TD_i=0.70(MED_i)$. The same phototherapy system 100 can determine individual treatment doses for vitamin D synthesis in accordance with the following formula: $TD_i=0.80(MPE_i)$, and cosmetic tanning can apply the following formula: $TD_i=0.75(MED_i)$.

In some embodiments, the phototherapy system 100 can receive biomarker information (e.g., blood/serum assays, urine, skin color, saliva, genetic markers, etc.) from various sources (e.g., user entry via the user interface 102, assay laboratory, user's doctor) before and/or during the treatment regime, and this information can be used to adjust the reduction factor and resulting $TD_i$. For example, before starting a SPK treatment for vitamin D synthesis, a user provides a blood sample to a lab and authorizes that lab to upload test results (e.g., 25 OHD=18 ng/ml) to the phototherapy system 100. The user then receives twelve treatments (t=12) with a $TD_i=0.65MPE$ before providing another blood sample to the lab, which in turn uploads results to the phototherapy system 102. Adjustments to the reduction factor ($R_f$) can be made based on the relationship between expected results for the twelve phototherapy sessions and the actual results. If expected results after t=12 is a level of 180% over a baseline (32.4 ng/ml) and the actual results for the user are 28 ng/ml (156% over baseline), the phototherapy system 100 can increase the reduction factor ($R_f$) to 0.75 ($TD_i=0.75MPE$) using this following formula (including example values in brackets): New $R_f=$Expected Result [1.8]*(Current $R_f$ [0.65]/Measured Result [1.56]). In some variations of the technology, the user (or user's doctor) can view the test results (e.g., 25 OHD=18 ng/ml and 28 ng/ml) and recommended treatment adjustment (15% dose increase or 0.75MPE absolute dose or dose time increase) so that the user can approve the dose adjustment for future treatments.

In some embodiments, the SPK dosing system 105 can receive user feedback about efficacy to current $TD_i$ that allows adjustment in the reduction factor. For example, after receiving a several treatment sessions (e.g., 3-30 treatment sessions) via the SPK 104, the phototherapy system 100 can request information from the user by asking a series of questions that assess or score efficacy. When measured results need to be improved to match expected results, the SPK dosing system 105 can adjust the reduction factor such that the $TD_i$ is increased for the individual user. The SPK dosing system 105 can make an opposite adjustment if measured results are superior to expected results and a reduction in $TD_i$ is desired to reduce overall UVR exposure to the user. For example, when a patient is using the SPK 104 for treatment of psoriasis, the SPK dosing system 105 can initiate a treatment protocol with a $TD_i=0.70MED$ for 20 treatments (t=20), after which the phototherapy system 100 presents the user (or user's doctor) with an assessment assay (e.g., The Psoriasis Area and Severity Index, The Dermatology Life Quality Index, or Simplified Psoriasis Index), which is scored and compared to the baseline assay that was completed by the user (or the user's doctor) before the treatment regime began (t=0). If the change between the t=0 and t=20 scores is less than expected for t=20, the system increases the $R_f$ to .to a higher value (e.g., 0.85) for the remaining treatments of that user. In some embodiments, the SPK dosing system 105 can incrementally increase or decrease the $R_f$ and $TD_i$ by set amounts (e.g., +/-0.05, 0.10, 0.15, 0.20, 0.25, 0.30) or based on the relationship between expected and actual results as previously described.

For some applications, such as endogenous vitamin D stimulation, adjustments can be made to the individual treatment dose $(TD_i)$ determination based on gender, age and/or BMI. This adjustment to $TD_i$ can be made when the $MED_i$, $MPE_i$ reduction factor is applied. The formula for $TD_i$ with reduction factor and adjustments for endogenous vitamin D based on gender, age, and/or BMI using either $MED_i$ or $MPE_i$ are as follows, where Female=1 for female users and 0 for male users:

$$TD_i=R_f*MED_i+(R_f*MED_i*\text{Female}*0.2)+(R_f*MED_i*\\(\text{Age-18})*0.008)+(R_f*MED_i*(\text{BMI-18})*0.01)$$

$$TD_i=R_f*MPE_i+(R_f*MPE_i*\text{Female}*0.2)+(R_f*MPE_i*\\(\text{Age-18})*0.008)+(R_f*MPE_i*(\text{BMI-18})*0.01)$$

For example, if a 25-year-old female user with a BMI of 24, the SPK dosing system 105 uses a reduction factor of 0.80 on a $MPE_i$ of 20 mJ/cm$^2$, and all the endogenous vitamin D stimulation adjustments are made, the $TD_i$=21.1 mJ/cm$^2$ (base [16]+female [3.2]+age [0.90]+BMI [0.96]).

Age Adjustment

In some embodiments, the SPK dynamic dosing system 105 can annually decrease $MPE_i$ and $MED_i$ with age at a predetermined rate per year (e.g., a rate between 0.2% to 1.4%, such as 8%). For example, if the SPK dynamic dosing system 105 determined a user had an $MED_i$ of 28 mJ/cm$^2$ during a photosensitivity discovery period on a first date, the SPK dynamic dosing system can reduce the user's $MED_i$ at a rate of 0.8% per year on the annual anniversary of the discovery period, the user's birthday, or an arbitrary date. After four years, the user's $MED_i$ would drop to 27.1 mJ/cm$^2$, with annual adjustments made that also impact $MPE_i$ and $TD_i$ settings.

Delivery Dose

The current delivery dose $(DD_c)$ corresponds to the dose to be delivered via the SPK 104 to the user during current treatment session. The current delivery dose is an amount of erythemally effective radiant exposure (mJ/cm$^2$) as measured by the CIE Erythema Action Spectrum. The previous delivery dose $(DD_p)$ is defined as the dose given during the prior treatment session. A dose of CIE weighted UVR is achieved by exposing the user to erythemally effective irradiance (mW/cm$^2$) over a period of time (seconds, minutes, etc.) until the delivery dose (mJ/cm$^2$) is achieved. The phototherapy system 100 can be configured to select the parameters of the SPK 104, such as the irradiance and/or the exposure time, to allow the SPK 104 to deliver the desired dose to the user. Total erythemally weighted spectral irradiance $(E_{er})$ is determined using the CIE erythema reference action spectrum as a weighting factor for each wavelength in the summation of spectral irradiance for all ultraviolet wavelengths (i.e., wavelengths of 250 nm to 400 nm) with a 1 nm interval.

$$E\_er=\Sigma\_(\lambda=250\text{ nm})^400\text{ nm}[E\_\lambda*S\_CIE]$$

The SPK dynamic dosing system 105 determines the exposure time necessary to deliver a dose (i.e., "dose time") when dividing by total erythemally weighted spectral irradiance as defined by the CIE standard. An erythemal weighting factor can be calculated as $E_{er}/E_t$, which can be multiplied by the unweighted irradiance to back calculate erythemally weighted spectral irradiance. When the SPK 104 includes UVR sources that are instant-on (such as LED sources) at stable irradiance, this SPK dynamic dosing system 105 can determine dose time as follows:

$$\text{Dose Time}=(\text{Dose }mJ/[\text{cm}]^2)/(\Sigma\_(\lambda=250\text{ nm})^400\\\text{nm}[E\_\lambda*S\_CIE])$$

In some embodiments, however, the SPK 104 includes UVR sources that require a warmup phase having variable irradiance during the first few seconds until irradiance reaches a stable phase with relatively constant irradiance. The summation of irradiance at each second during a defined warmup phase time $(T_A)$ can be used to determine a constant dose $(D_A)$ during the warmup phase. The warmup phase time can be considered the minimum dose time of the SPK 104, as any time shorter than this is unpredictable and cannot be used for dose calculations. FIG. 3 provides graphical representations for determining dose time for phototherapy protocols when the phototherapy system includes UVR sources with warm up phases. As illustrated in FIG. 3, the total treatment time in seconds $(T_C)$ needed to deliver the desired dose in mJ/cm$^2$ $(D_C)$ can be calculated using the following formula:

$$\text{"}TC\text{"}=\text{"}TA\text{"}+(\text{"}DC\text{"}-\text{"}DA\text{"})/\text{"}IB\text{"}$$

Figure 4:
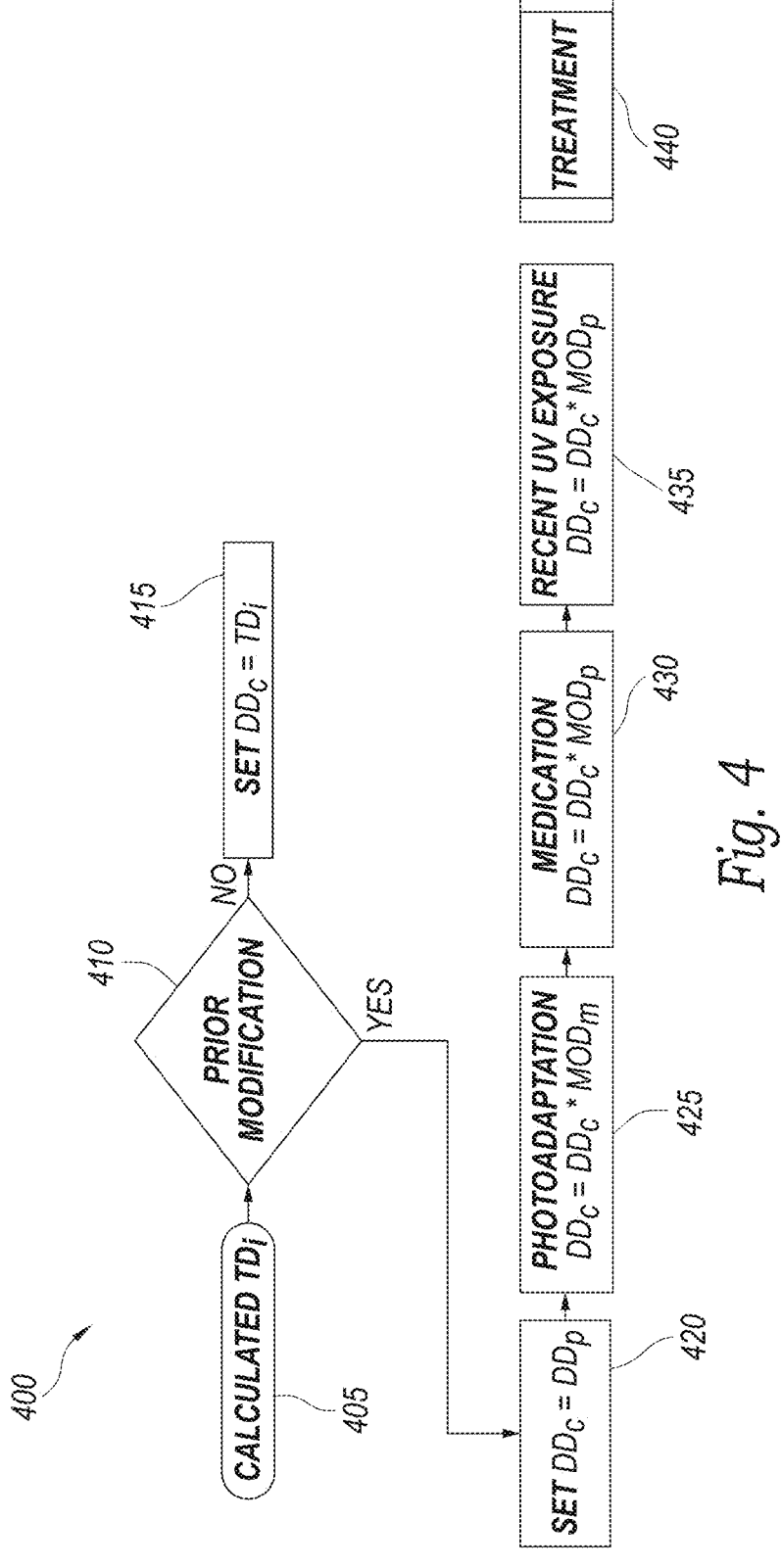
FIG. 4 is a flow diagram illustrating a dose modification routine configured in accordance with embodiments of the present technology.

In some embodiments, the SPK dynamic dosing system 105 can make modifications to the current delivery dose (DDc) before treatment to account for photoadaptation, photosensitizing medication usage, recent UV exposure, and/or other adjustment parameters. FIG. 4, for example, is a flow diagram illustrating a dose modification routine 400 configured in accordance with embodiments of the present technology. The dose modification routine 400 begins by receiving or determining an individual treatment dose (block 405), and then determining if a prior modification to the individual treatment dose has been stored in association with the user (decision block 410). If the prior modification has been stored, the routine 400 moves to block 415 to equate the current delivery dose to the predetermined treatment dose, whereas if there was a previous modification associated with the user, the routine 400 would move to block 420 where the routine 400 equates the current delivery dose to the previous delivery dose. Once the current delivery dose has been set, the routine 400 moves to blocks 425, 430, and 435 where the SPK dosing system 105 (FIG. 1) modifies the current delivery dose based on information provided by the user regarding photoadaptation (block 425), medication (block 430), and/or recent UV exposure (block 435). In some implementations, modifications can be compounded sequentially as shown in FIG. 4. In some embodiments, the SPK dosing system 105 applies one modification (e.g., Modp), but then does not apply subsequent modifications (e.g., Modm and Modu). After the modifications are made to the current delivery dose, the SPK 104 (FIG. 1) can deliver the treatment in accordance with the modified current delivery dose (block 440).

Photoadaptation Modification $(Mod_p)$

In some embodiments, the SPK dosing system 105 can modify delivery doses after receiving information related to previous UVR exposure. For example, if the treatment protocol includes sessions with a frequency greater than once every six to ten days, photoadaptation is expected to increase. When treatment sessions are less frequent, photoadaptation is expected to decrease until a baseline photosensitivity is reached. In some embodiments, the phototherapy system 100 is designed to increase dose to compensate for photoadaptation during periods of frequent treatments and reduce dose during periods of infrequent treatments. The SPK system considers the point where photoadaptation remains the same as the Adaptation Threshold ($AT_i$), where dose is not increased or decreased. Photoadaptation is expected to increase or decrease on either side of an adaptation threshold ($AT_i$) in a linear response to time, where maximum increase in photoadaptation occurs when treatments are 48 hours apart. An incremental increase to the previous delivery dose ($DD_p$) can be made for each treatment up to an individual maximum dose ($MD_i$), which can be 300-600% more than the treatment dose ($TD_i$). The MD, can be based on UVR spectrum and/or indication for use. For example, devices that contain greater than 75% UVA can have an MD, of 300-400% more than the $TD_i$, and devices that contain less than 75% UVA can have an $MD_i$ 500-600% more than the $TD_i$. In this example, the SPK 104 can also have a MD, for dermatologic treatment higher (600%) than vitamin D synthesis (500%) for a device that contains less than 75% UVA.

Thus, the SPK dosing system 105 can increase the dose configured to be delivered by the SPK 104 to account for increasing photoadaptation during frequent treatments, and the SPK dosing system 105 can also decrease dose to account for decreasing photoadaptation during infrequent treatments. FIGS. 5A-5B, for example, illustrate a photoadaptation modification matrix 503 for use with phototherapy systems configured in accordance with embodiments of the present technology. As shown in FIGS. 5A-5B, the photoadaptation modification adaptation factor ($AF_i$) can be 115-130% when treatments are once every 2 days, and the adaptation threshold ($AT_i$) can be between 6-10 days. In some embodiments, the $AF_i$ and $AT_i$ can depend on the UVR spectrum and/or indication for use. SPK devices that contain greater than 75% UVA can have a lower adaptation factor (115-120%) and longer adaptation threshold (8-10 days), while SPK devices that contain less than 75% UVA can have a higher adaptation factor (120-130%) and shorter adaptation threshold (6-8 days). In other embodiments, the user's doctor can prescribe (set) the photoadaptation modification $AF_i$, and $AT_i$, based on the indication for use, severity of condition, acute need and/or other factors. FIGS. 5A-5B show the photoadaptation modification (% of previous treatment dose) increase and decrease based on treatment frequency. When a dose increase would lead to a dose greater than $MD_i$, then the $MD_i$ should be used. When a dose decrease would lead to a dose less than $TD_i$, then the $TD_i$ should be used. The SPK dosing system 105 can also reset to the $TD_i$ when too many days have passed between treatments.

As an example, the SPK dosing system 105 can include instructions for a photoadaptation modification using an adaptation factor ($AF_i$) of 125%, adaptation threshold ($AT_i$) of 7 days, and maximum dose ($MD_i$) setting of 600%. For a user with a $TD_i$ of 20 mJ/cm² that had a previous treatment dose ($DD_p$) of 60 mJ/cm² four days ago, the current treatment dose ($DD_c$) should be 115% (69 mJ/cm²) of the previous delivery dose, but if the user had the same dose 23 days ago, the current treatment dose should be reset to the $TD_i$ (20 mJ/cm²). If the same user had a previous treatment dose of 118 mJ/cm² three days ago, the next treatment modification is 120% (141.1 mJ/cm²), which is a higher dose than the $MD_i$ limit. Accordingly, the current delivery dose is set to the $MD_i$ (120 mJ/cm²). If the same user came back 19 days after receiving a previous delivery dose of 120 mJ/cm², the next treatment modification should be 40%, and the current delivery dose would correspond to 48 mJ/cm².

Medication Modification (Modm)

The SPK dosing system 105 can also modify the delivery dose based on information received from the user regarding medications. FIG. 6, for example, is a medication identification GUI 605 configured to be displayed on a user interface 102 (FIG. 1) in accordance with embodiments of the present technology. The medication identification GUI 605 asks the user whether he or she is using any medication that makes his or her skin photosensitive (i.e., more likely to sunburn) and provides a list of medicines that may have this effect. Users can press the "∧" and "∨" arrow buttons on the medication identification GUI 605 or use "up" and "down" verbal commands to scroll up and down a list of photosensitizing medications. The "Y" or "N" buttons on the medication identification GUI 605 (or "yes" and "no" commands) are used to answer the photosensitizing medication question. If a user selects the "Y" button (or use the "yes" command), her or she can receive a caution message or a software lockout preventing SPK treatment for a specified period of time (e.g., a number of days, weeks, or months), until unlocked by an administrator (doctor, clinician, health care professional, SPK customer service, etc.), or lock out the user indefinitely. In some embodiments, the SPK dosing system 105 can modify (e.g., reduce) the current delivery dose ($DD_c$) by a predetermined amount (i.e. 10%, 20%, 30%, 40%, 50%, 60%, 70%, 80%, 90%) to prevent erythema when the user identifies that he or she is using a photosensitizing medication. Because some medications are more photosensitizing others, the amount of the medication modification ($Mod_m$) dose reduction can also be based the medication identified by the user. Each medication can have an individual $Mod_m$ value.

Recent UV Modification ($Mod_u$)

The SPK dosing system 105 can also modify the delivery dose based on information received from the user regarding recent UV exposure. FIG. 7, for example, is a UV exposure GUI 707 for display on one of the user interfaces 102 (FIG. 1) configured in accordance with embodiments of the present technology. The UV exposure GUI can pose questions to the user to determine if the user has sunbathed, received an indoor tanning treatment, or received phototherapy treatment in the last 24 hours and/or another predetermined time frame which increases risk of sunburn. Selecting the "Y" or "yes" button or command on the UV exposure GUI 707 can cause the user interface 102 to display or otherwise communicate a caution message or initiate a software lockout preventing SPK treatment for a predetermined period (number of days, weeks, or months) of time. In other embodiments, the SPK dosing system 105 can modify (reduce) the delivery dose ($DD_c$) by a set amount (e.g., 10%, 20%, 30%, 40%, 50%, 60%, 70%, 80%, 90%) to avoid erythema when the user identifies that he or she has received significant UV exposure within the last 24 hours (or other time period).

Erythema Response

The phototherapy system 100 can be responsive to user's skin reactions to previous phototherapy sessions and/or other UV exposure to adjust dosage as user skin characteristics are further defined. For example, the SPK dosing system 105 can be configured to determine or estimate erythema response of the user. Absolute determinations of individual photosensitivity are made by measuring or grading erythema response to a known dose of the UVR. This measuring or grading is performed by experienced clinicians that are trained to visually score skin response 24-hours after UVR exposure to determine MED, and can identify the subtle differentiations of erythemal response that can categorize MPE, MED, $E_2$, $E_3$ or $E_4$ events. In addition, MED determination requires skin masking to make to make clinical assessments 24-hours post-exposure. The phototherapy system 100 can capture relevant information about skin response to a known dose, while still being used in a non-clinical setting without access to clinicians and clinical erythema response testing. For example, the SPK dosing system 105 can interpret and adjust subsequent a dose based on self-reported responses to questions designed for an untrained user. These erythema response-based questions, which are provided to users via one of the user interfaces 102, can relate to erythema, sunburn, skin color change, length of skin color change, tanning, discomfort, pain, itching, peeling, blisters, and/or areas of skin impacted. The responses to the questions can be presented to users as written descriptions, pictures, graphic images, and/or number scales for the user to select.

When assessing erythema response, the SPK dosing system 105 can take into account the amount of time between the last UVR exposure (either via the phototherapy system 100 and/or other natural or synthetic UVR exposure) and when the pre-treatment information is requested and received from the user. This time interval can affect both type of question asked of the user and the assessment of the user's response. For example, a question regarding erythemal response to a previous phototherapy treatment session or blisters should be asked of the user between 18 and 48 hours after the phototherapy treatment session because this is when peak capillary dilation occurs. In some embodiments, the SPK dosing system 105 can use skin color change that lasts more than three days is the grading criteria. When this criterion is used, inquires related to the duration of skin color change should be asked between four to seven days after treatment. Similarly, skin color changes that last more than seven days should be asked no less than seven days after treatment. The SPK dosing system 105 can also be configured to present questions regarding pain or discomfort post-UVR exposure. To enhance accuracy, these can be posed 24-48 hours after a phototherapy treatment session when hyperalgesia is peaking or between two and seven days when recall may be less biased toward overreporting degree of pain or discomfort. Similarly, because itching and/or peeling normally occurs with $E_2$-$E_4$ events more than 1 week after UVR exposure, questions regarding itching and/or pealing can be posed to the user less than seven days post-treatment.

Figure 8:
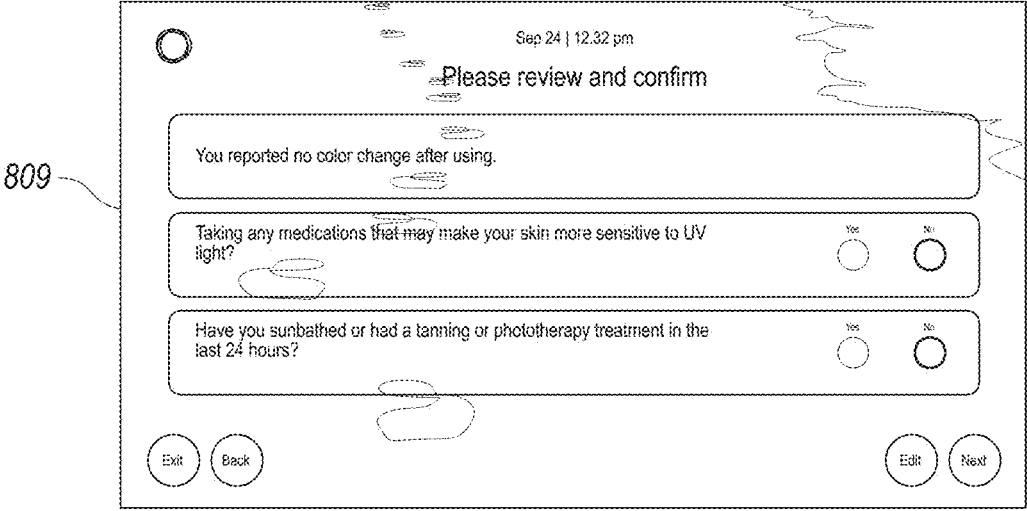
FIG. 8 illustrates a GUI for confirming or editing previously-provided information for determining phototherapy parameters in accordance with embodiments of the present technology

The phototherapy system 100 is designed to present these and other erythema response-related questions to the user via text message, a smartphone application, a smartphone application push notification, email, and/or the user interfaces 102 of the SPK 104, and these questions can be provided at specific time points after a phototherapy treatment session when response is most relevant and accurate to the specific question. Answers to the questions can be provided by the user within the same medium used for question delivery or a link that can connect the user to a web services application. The date, time, and answers of all questions can be stored in a cloud database to insure traceability and allow machine learning of the relationship between dose and treatment response. In some embodiments, responses can be given on the smartphone application and presented to user on one of the user interfaces 102 of the SPK 104 prior to the next phototherapy treatment session to allow the user to edit responses and/or provide confirmation. FIG. 8, for example, illustrates a GUI 809 for confirming or editing previously-provided information related to erythema response and other factors that may impact phototherapy parameters in accordance with embodiments of the present technology.

In some embodiments, the phototherapy system 100 can be configured to present additional erythema response-related questions only when a specific response is given to a previous question. For example, if the user responds that he or she had an erythemal response 24 hours after a phototherapy treatment session, then another question can be presented to the user four to seven days later (e.g., via smartphone application, email, or other device) to determine if the erythema has subsided, and/or another question can be presented seven to fourteen days post-phototherapy treatment to determine whether there is lasting skin color change (i.e., tanning). If the user had no erythemal event, then the phototherapy system 100 can be configured to abstain from subsequent questions or only request information related to skin color changes—seven to fourteen days after the phototherapy treatment session. The type of questions, length of time after exposure, and/or the manner in which the information is presented to the user can change depending on the spectral composition (i.e., UVA/UVB percentage) of UVR delivered and/or the indication of use (e.g., endogenous vitamin D, psoriasis, tanning) In some embodiments for endogenous vitamin D, the phototherapy system 100 can present a binary question regarding skin color change less than three days post-treatment, and any skin color change will prompt subsequent questions (solicited at the same or a later time) regarding skin color change lasting more than three days as well as discomfort/pain within the same questionnaire presented at that time. In other embodiments for psoriasis treatment, the phototherapy system 100 can present a single question about erythema response 24-48 hours post-exposure and provide answers using pictures and/or words showing or describing grades of erythema (e.g., no erythema, very faint, faint, moderate $E_2$, major $E_3$, extreme $E_4$) with user-friendly characteristics, such as discomfort, color change, or edema.

Figure 9:
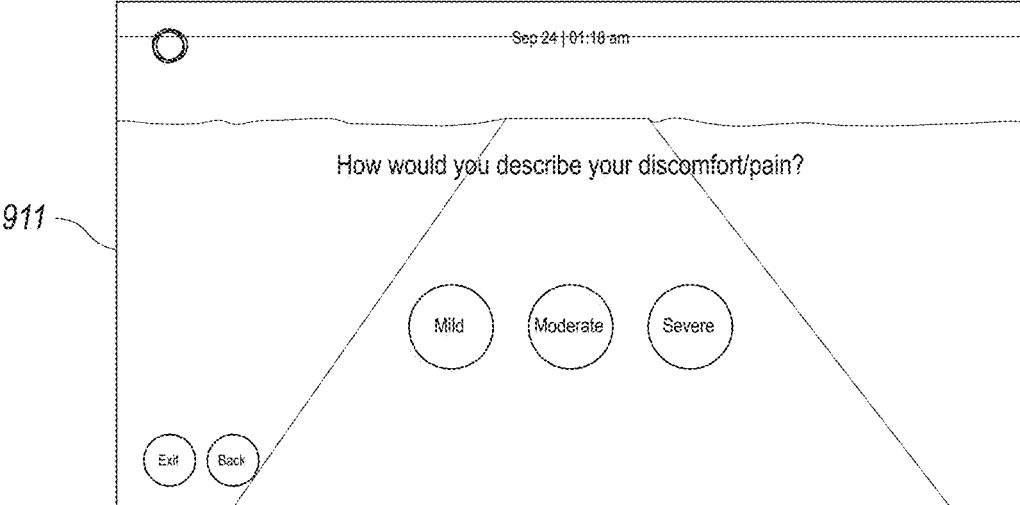
FIG. 9 illustrates a discomfort level GUI configured in accordance with embodiments of the present technology.
Figure 10:
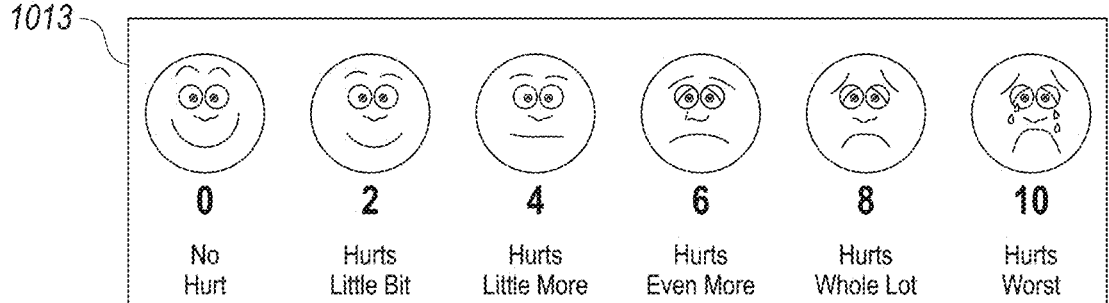
FIG. 10 illustrates a discomfort level GUI configured in accordance with other embodiments of the present technology.

FIGS. 9 and 10 illustrate discomfort level GUIs 911 and 1013, respectively, configured in accordance with embodiments of the present technology. As shown in FIG. 9, for example, if the user reported any discomfort or pain, he or she can be presented the discomfort level GUI 911 that requests the user rate the level of discomfort. Selections of "mild", "moderate" or "severe" can be offered for users to self-assess. In other embodiments, such as the discomfort level GUI 1013 shown in FIG. 10, a numeric pain rating scale can be used (1-10, 1-5, 1-3, etc.) with different pain descriptors and/or illustrations (e.g., faces) to rate the user's discomfort level.

The SPK dosing system 105 can include logic that allows various different information requests (e.g., questions presented to the user via the user interfaces 102) to be transmitted and received in various combinations to determine photosensitivity to estimate MPE, MED, and potential dose adjustments for the current phototherapy treatment session. FIG. 11, for example, is an erythema response matrix 115 for use with the phototherapy system 100. The erythema response matrix 115 provides an example list of questions, answers, and the best timeframe (e.g., period after previous UVR exposure) to receive response feedback from the user. In some embodiments, number scales (e.g., 1-3, 0-5, 1-10) can be used as a substitute for descriptive answers, such as none, very slight, slight, moderate, severe.

The phototherapy system 100 can use combinations of questions and user responses to the posed questions to estimate MPE, MED, and E2-E4 erythemal events that occurred after a known UVR dose was delivered to the user. Differentiation between the different erythemal degrees can be estimated with a single question response, but accuracy may be increased by combining multiple questions/answers. Sub-dividing first degree erythemal events into MPE or MED can be especially difficult, although the phototherapy system 100 can do so with some accuracy with a question algorithm that identifies these nuances. Tanning response can also be captured along with erythema response to determine if dosage needs to be increased to stimulate melanogenesis, while still avoiding sunburn. FIGS. 12 and 13are question matrices 1217, 1319 for assessing minimal perceived erythema and minimal erythemal dose, respectively, in accordance with embodiments of the present technology. FIGS. 14-16 are matrices 1421, 1523, 1625 for assessing second-through fourth-degree erythema, respectively, used to better define phototherapy treatment protocols in accordance with embodiments of the present technology. The matrices shown in FIGS. 12-16 illustrate which answers can be interpreted to distinguish the escalating erythemal events. Based on the received responses, the SPK dosing system 105 can automatically adjust individual MPE, MED, and treatment dose (MPEi, MEDi, TDi) to reflect the user's specific erythema response. In some embodiments, the phototherapy system 100 can be configured to receive clinically determined photosensitivity results (e.g., transmitted by a clinician to the system 100), and the SPK dosing system 105 can automatically adjust individual MPE, MED, and treatment dose (MPEi, MEDi, TDi) to reflect the clinically-provided data.

Treatment Frequency Recommendation ($TF_R$) and Limit ($TF_L$)

The phototherapy system 100 can also be configured to automatically provide treatment frequency recommendations ($TF_R$) and treatment frequency limits ($TF_L$) based on the information received from users. The indication for use is a primary driver in determining the treatment frequency recommendation ($TF_R$) and treatment frequency limit ($TF_L$). For example, the number of treatments needed to provide an efficacious therapy regime can change depending indication for use (e.g., dermatologic disorder, vitamin D synthesis, cosmetic suntan, etc.). Treatment limits ($TF_L$) can be enforced by software lockouts incorporate in the SPK 104 and/or SPK dosing system 105 to prevent scheduling treatment via a smartphone application, the user interface 102 of the SPK 104, and/or other device. To improve compliance and efficacy, treatment reminders can be sent by the phototherapy system 100 (e.g., via email, text message, and/or smartphone application push notification) when the user is due for a treatment based on treatment frequency recommendation ($TF_R$). The reminder can allow the user to schedule a treatment through the delivery medium (e.g., via email, text message and/or smartphone application) or a link to a webservices application that is selected within the reminder message. Reminders can be triggered (i.e., sent) to users at selected time and/or days (e.g., one to seven days) after the user has not received a phototherapy treatment during the recommended period. The speed of reminder delivery ("trigger speed") can be the same for all users or change based on indication for use and/or other factors, such as user-selected reminders or previous adherence to treatment protocol recommendations. For example, the trigger speed can be one to two days for dermatologic disorders, three to four days for vitamin D synthesis, and five to seven days for cosmetic tanning For dermatologic disorders, the treatment frequency recommendations ($TF_R$) may be two to four treatments per month, and the treatment frequency limits ($TF_L$) may be one treatment every two days. For vitamin D synthesis, the treatment frequency recommendations ($TF_R$) may be one to four treatments per month, and the treatment frequency limits ($TF_L$) may be one treatment every three days. For tanning, the treatment frequency recommendations ($TF_R$) may be four to eight treatments per month, and the treatment frequency limits ($TF_L$) may be one treatment every two days. In other embodiments, the treatment frequency recommendations ($TF_R$) and treatment frequency limits ($TF_L$) may differ based on the indication, user-specific characteristics, and/or other parameters.

Some conditions require more frequent treatments during an "active phase" and as conditions change, so too can $TF_R$ and/or $TF_L$. For example, a user can have a more urgent need (i.e., active psoriasis flare, vitamin D deficiency, or no base tan) when beginning treatment for an indication (dermatologic disorder, vitamin D synthesis, cosmetic suntan) that requires multiple treatments per week for a given number of weeks (active phase) before the frequency is reduced to a lower frequency, such as no more than once per week for maintenance phase. For example, dermatologic disorder treatment can have $TF_R$ of two to three exposures per week with the $TF_L$=1 treatment every two days for an active phase of three to five months, and then a $TF_R$ of once every one to two weeks with the $TF_L$=1 treatment/week for maintenance. For endogenous vitamin D, $TF_R$ can be two exposures per week with the $TF_L$=1 treatment every three days for an active phase of three to four months, and then a $TF_R$ of once every one to four weeks with a $TF_L$=1 treatment/week for maintenance. For cosmetic tanning, $TF_R$ can be four treatments per week with the $TF_L$=1 treatment every two days for an active phase of one to two months, and then a $TF_R$ of one to two times per week with the $TF_L$=1 treatment every two days for maintenance. In other embodiments, the user's doctor can prescribe (set) the $TF_R$ and $TF_L$ based on indication for use, severity of condition, acute need and/or other factors, and this information can be directly communicated by the physician to the phototherapy system 100 via a network connection.

The treatment reminder trigger speed can be increased or decreased depending on the phase (active or maintenance) of the treatment regimen the user is in. For example, trigger speed can be faster (e.g., one to three days) during the active treatment phase and slower (e.g., four to seven days) during the maintenance phase. In other embodiments, the trigger speed can be slower during the active phase and faster during the maintenance phase. The $TF_R$ and/or reminder trigger speed can be increased for users that have certain physical characteristics such as gender, age and BMI. For example, when the indication for use is vitamin D synthesis, recommended the $TF_R$ and/or reminder trigger speed can increase by up to 20% (1-25%) for male gender, 0.8% (0.2-1.4%) for each year of age over 18, and 1.0% (0.4-1.6%) for each BMI point over 18.

Photosensitivity Discovery Dose (PDD)

In some embodiments, the SPK dosing system 100 can adjust $TD_i$ and/or $DD_c$, but not $MPE_i$ or $MED_i$ estimates based on erythema response. Adjustments to individual MPE and MED estimates can be applied only to naïve skin (e.g., new users or users that have not used the SPK 104 in more than three months) when transient circumstances would not impact photosensitivity. For example, if a dose was reduced for medication usage or recent UV exposure, and the user reports an erythemal event, future dose reductions can be made if the same conditions are present (e.g., when the user is using the same medication), but no reductions are made to $MPE_i$ or $MED_i$ estimates that impact dose with no photosensitizing condition. The phototherapy system 100 can also maintain individual $MPE_i$ or $MED_i$ estimates (i.e., without adjustment up or down) in situations where photoadaptation may be reducing photosensitivity by an unpredictable amount. The SPK dosing system 105 can also be configured to include a specific discovery period designed to provide $MPE_i$ or $MED_i$ estimates using a photosensitivity discovery dose (PDD) that is designed to purposefully deliver an erythema threshold dose of UVR during a period when photosensitivity is not impacted by photoadaptation, medication use, recent UV exposure and seasonal sunlight exposure. During the discovery period, the PDD may be incrementally increased (e.g., 10%, 15%, 20%, 25%, 30%, 35%, 40%, 45%, 50%, 55%, or 60%) from one treatment to the next until an erythemal event occurs and is reported by the user during post-treatment response questions.

Figure 17:
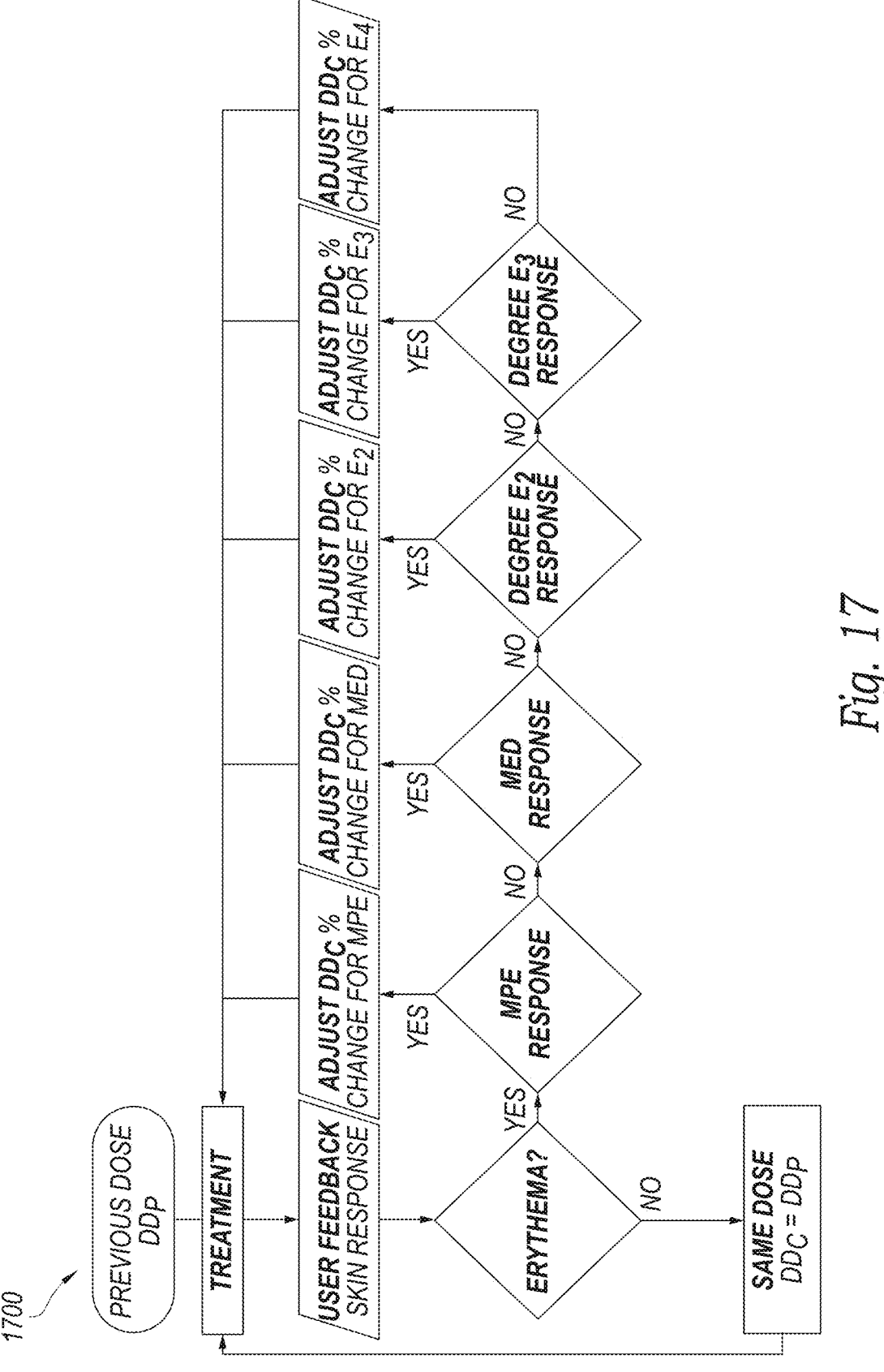
FIG. 17 is a flow diagram illustrating a dynamic dosing routine configured in accordance with embodiments of the present technology.

In some embodiments, the treatment frequency can be limited with software lockouts at the beginning of therapy, during the screening or discovery period when photoadaptation can interfere with erythemal response needed to predict and adjust $MPE_i$ or $MED_i$. The phototherapy system 100 can prevent new users from receiving treatment sooner than the adaption threshold (six to ten days) for the first two to three treatments. In some embodiments, the phototherapy system 100 can enforce a software lockout that prevents any user from receiving treatment sooner than a photoadaptation washout period (e.g., two to four weeks) and/or the adaption threshold whenever the system is attempting to discover individual photosensitivity to predict and/or adjust $MPE_i$ or $MED_i$. This discovery period that enforces a frequency restriction can occur periodically, seasonally, and/or opportunistically. For example, the phototherapy system 100 can periodically (e.g., once every year, once every two years, once every three to ten years) prevent a user from receiving treatment for a predetermined period weeks (e.g., three weeks, photoadaptation washout), and then deliver a PDD designed to discover/confirm $MPE_i$ or $MED_i$ through erythema feedback. A further PDD increase may be needed for $MPE_i$ or $MED_i$ discovery so a software lockout prevents treatment prior to the adaption threshold. phototherapy system 100 can also be configured such that the photoadaptation washout lockout only occurs during/near the winter season when environmental sun exposure that contributes to photoadaptation confounds erythemal response. The phototherapy system 100 can also or alternatively opportunistically start a discovery period and set $DD_c$=PDD to discover/confirm $MPE_i$ or $MED_i$ after normal user usage pattern provides a photoadaptation washout (e.g., two to four weeks between treatments). In this situation, a further PDD increase may be needed for $MPE_i$ or $MED_i$ discovery so a software lockout prevents treatment prior to the adaption threshold until discovery period is ended. In other embodiments, the phototherapy system 100 can determine $MPE_i$ or $MED_i$ during a discovery period, which can be saved to the user account and no other discovery periods are performed.
Feedback Adjustment The SPK dynamic dosing system 105 can adjust $MPE_i$, $MED_i$, $TD_i$ and/or $DD_c$ based on erythema response feedback received by the user. FIG. 17, for example, is a flow diagram illustrating a dynamic dosing routine 1700 configured in accordance with embodiments of the present technology. As shown in FIG. 17, the fundamental structure of the SPK dynamic dosing system 105 uses a known previous delivery dose ($DD_p$) from the last phototherapy treatment in combination with subsequent erythemal response feedback from the user to determine the current delivery dose ($DD_c$).

In some embodiments, the SPK dynamic dosing system 105 makes adjustments to $MPE_i$, $MED_i$, $TD_i$, and/or $DD_c$ based on a known relative dose needed to produce different degrees of erythema and an interpretation of the user-reported erythemal response to systematically predict future response. The SPK dynamic dosing system 105 can refer to a lookup table, such as Table 12, which provides the SPK dynamic dosing system 105 with a range (low, mid, and high) of response for each degree of erythema based on 1 MED. For example, if user input regarding skin response to $DD_p$ indicates that the user received an $E_2$ event to 40 $mJ/cm^2$, then future exposure at 16-20 $mJ/cm^2$ will likely result in an MED event (1MED range=($E_2$ Dose)/(2.5 to $E_2$ Dose)/2.0). In this example, a single $MED_i$ prediction can be 16 $mJ/cm^2$, 18 $mJ/cm^2$ or 20 $mJ/cm^2$ depending on the low, mid, or high $E_2$ selection respectively. In another example, the user input regarding skin response to 40 $mJ/cm^2$ indicates that the user received an MED event predicting that actual MED may be 110% (36.4 $mJ/cm^2$) to 90% (44.4 $mJ/cm^2$) of the $DD_p$ provided. In this example, $MED_i$ for the user can be set in phototherapy system 100 to 36.4 $mJ/cm^2$ (low) for safety reasons (e.g., to prevent burning or tanning), set to 44.4 $mJ/cm^2$ (high) for efficacy reasons, or set to 40 $mJ/cm^2$ (mid) for a balance of both efficacy and safety. $MPE_i$ can be calculated as 60-80% of the $MED_i$ value. Therefore, if $MED_i$ is set to 40 $mJ/cm^2$ for a user based on erythema response, then $MPE_i$ can be set for that user between 24 $mJ/cm^2$ and 32 $mJ/cm^2$ with a middle value of 28 $mJ/cm^2$.

TABLE 12

| Dosage for Production of Degrees of Erythema (Percentage of 1 MED for Erythema Response) | | | |
|---|---|---|---|
| | Low | Mid | High |
| MPE | 60% | 70% | 80% |
| MED | 90% | 100% | 110% |
| E2 | 200% | 225% | 250% |
| E3 | 400% | 450% | 500% |
| E4 | 800% | 900% | 1000% |

Figure 18:
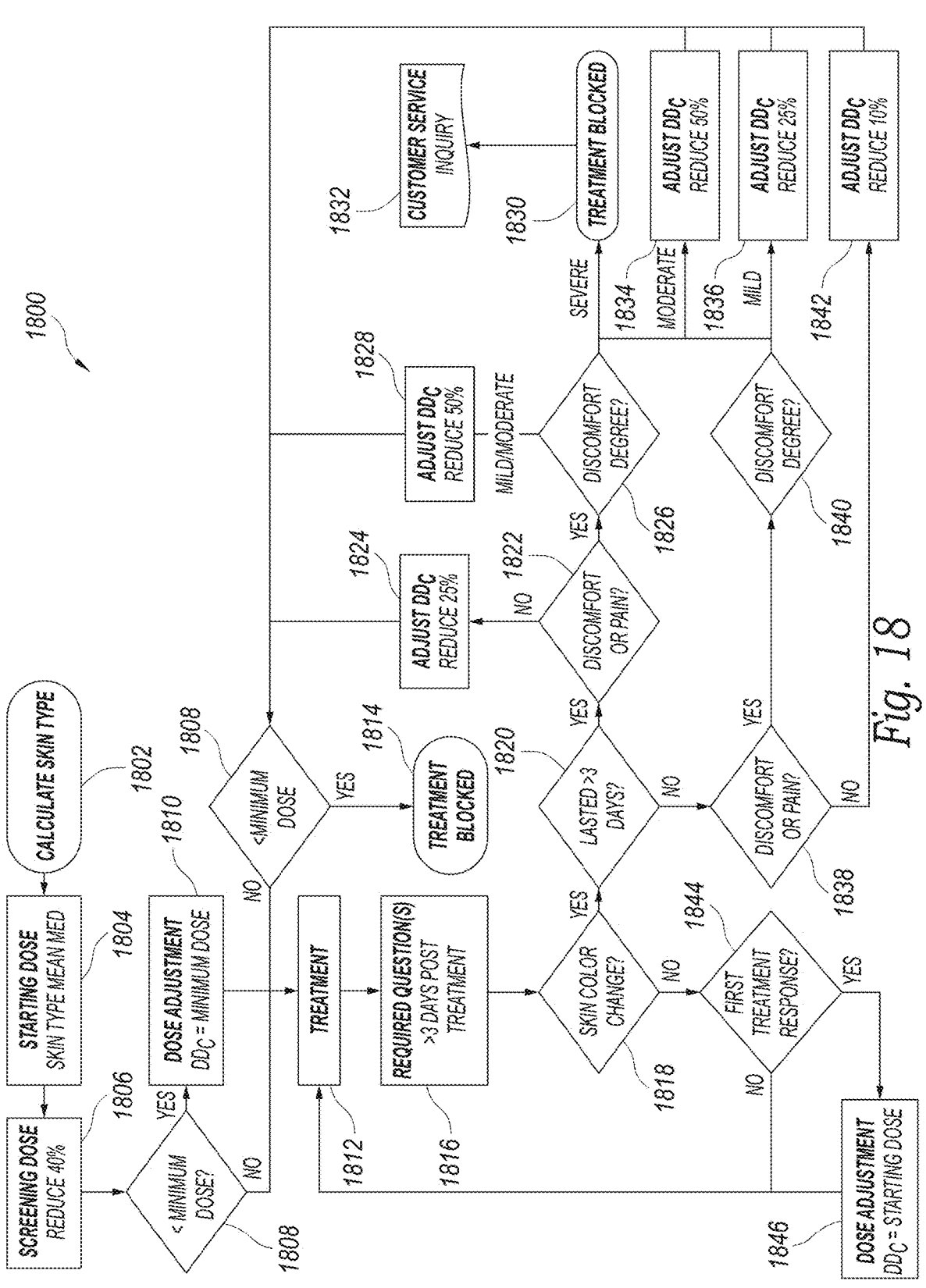
FIG. 18 is a flow diagram illustrating a skin response dynamic dosing routine configured in accordance with embodiments of the present technology.

Changes to $TD_i$ and/or $DD_c$ can be made with changes to $MPE_i$ or $MED_i$ as individual photosensitivity is related to dose. In some embodiments, the SPK dynamic dosing system 105 can create treatment protocols with varying degrees of reduction to $DD_c$ based on user-reported skin response without predicting degree of erythema response or changing $MPE_i$ or $MED_i$. FIG. 18, for example, is a flow diagram illustrating a skin response dynamic dosing routine 1800 that can be implemented by the SPK dynamic dosing system 100. The dynamic dosing routing 1800 uses skin type to determine a starting dose (blocks 1802 and 1804), causes the SPK 104 to deliver a single screening dose (block 1806), compares the screening dose to the device minimum dose (block 1808), and adjusts current delivery dose ($DD_c$) based on skin response to the previous delivery dose ($DD_p$) to prevent future erythemal events (block 1810). In this method 1800, treatment can be blocked (block 1814) if the current delivery dose ($DD_c$) needed to prevent erythema is below the minimum dose of the device (determined via block 1808) or the user's skin response to the previous treatment resulted in severe pain (block 1830). In this embodiment, a severe skin response to treatment triggers a customer service inquiry (block 1832) by automatically generating an email to the user and/or customer service department about the event. In some embodiments, the method 1800 can include additional steps, such as repeated screening doses at increasing dosage levels, and/or some of the steps can be omitted.

In some embodiments of the technology, photoadaptation modifications to $DD_c$ can be made based on erythemal response to $DD_p$ as well as the treatment frequency calculations using $AF_i$ and $AT_i$ described in FIGS. 5A-5B. Photoadaptation modifications are designed to deliver a biologically equivalent dose with changing skin photosensitivity. Therefore, a user-reported erythemal response that is greater than expected for the $TD_i$ setting can initiate a modification to $DD_c$ as well as an adjustment to the individual adaptation factor ($AF_i$) and/or adaptation threshold ($AT_i$) settings that are stored in correlation with the user profile. For example, if a user with a $TD_i$=0.75MED$_i$ reports a MED+ (MED, $E_2$, $E_3$, $E_4$) erythemal response after receiving a photoadaptation adjusted $DD_p$ treatment, the SPK dynamic dosing system 100 can initiate an adjustment to the photoadaptation modification of $DD_c$ and/or $AF_i$, $AT_i$ settings for the user. In some embodiments, the SPK dynamic dosing system 105 can prevent the user from receiving any photoadaptation adjusted increase in $DD_c$ or force an additional reduction ($DD_p$/Adaptation Factor) in $DD_c$ for the very next treatment after reported erythemal response >$TD_i$. In this and other embodiments, an erythemal response >$TD_i$ to a photoadaptation modified $DD_p$ treatment will initiate the SPK dynamic dosing system 105 to reduce the $AF_i$ by a given increment (1-5%) for all future treatments of that user. In this and other embodiments, SPK dynamic dosing system 105 can be configured to only make a reduction to the $AF_i$ by a predetermined increment (1-5%) when an erythemal response >$TD_i$ is reported after a Mod$_p$ increased $DD_p$ treatment (previous treatment frequency >adaptation threshold). In another embodiment, the $AT_i$ can be reduced for all future treatments of that user when erythemal response >$TD_i$ is reported after any photoadaptation modified_$DD_p$ treatment. In this and other embodiments, the SPK dynamic dosing system 105 may only make a reduction to the $AT_i$ when an erythemal response >$TD_i$ is reported after a Mod$_p$ decreased $DD_p$ treatment (previous treatment frequency <Adaptation Threshold).

Figure 19:
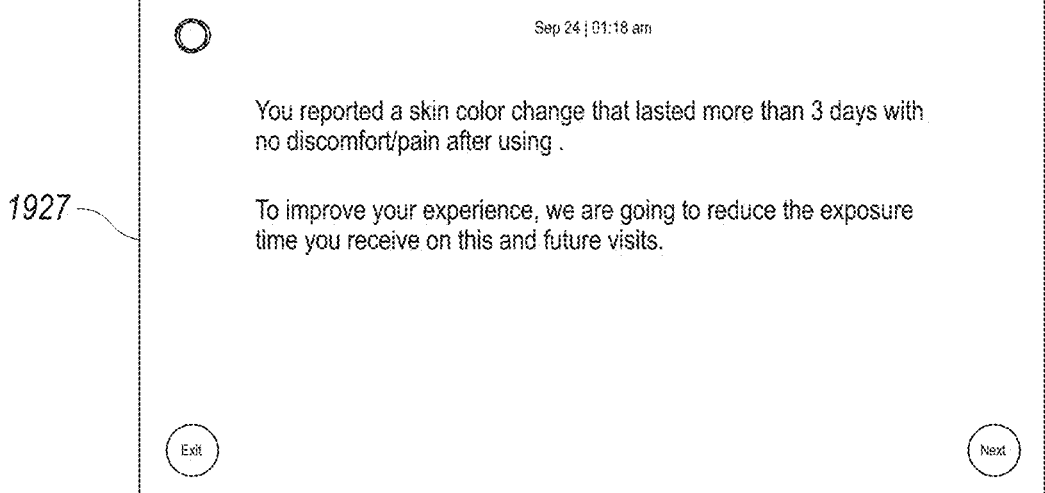
FIG. 19 illustrates a dose adjustment GUI configured in accordance with embodiments of the present technology.

FIG. 19 is a dose adjustment GUI 1927 configured in accordance with embodiments of the present technology. The dose adjustment GUI 1927 can display the user's reported erythema, skin color change, and/or discomfort response to previous SPK treatment. Information about future treatment adjustments can be displayed on this GUI 1927 as well. Answers to questions regarding previous treatment response will allow the SPK dynamic dosing system 105 to adjust dosage for future treatments if necessary to prevent or avoid erythema or discomfort. In some embodiments, certain previous treatment responses can result in a software lockout that prevents using the SPK 104. In those situations, the phototherapy system 100 can block treatment for that day, a select number of days, or all future use. The phototherapy system 100 can also initiate a customer service follow up with the user that had a >=$E_2$ event by sending an automated email to the user that requests they contact customer support or reply with answers to further questions about the event. The system 100 can also generate a notification to customer service that a >=$E_2$ event occurred and generate summary information about the user such as: skin type, MPE$_i$, MED$_i$, TD$_i$, DD$_p$, DD$_c$, AF$_i$, AT$_i$, indication for use, usage history (including erythema response), email, phone number, age, gender, recent UV exposure answer, and/or medication usage.

Figure 20:
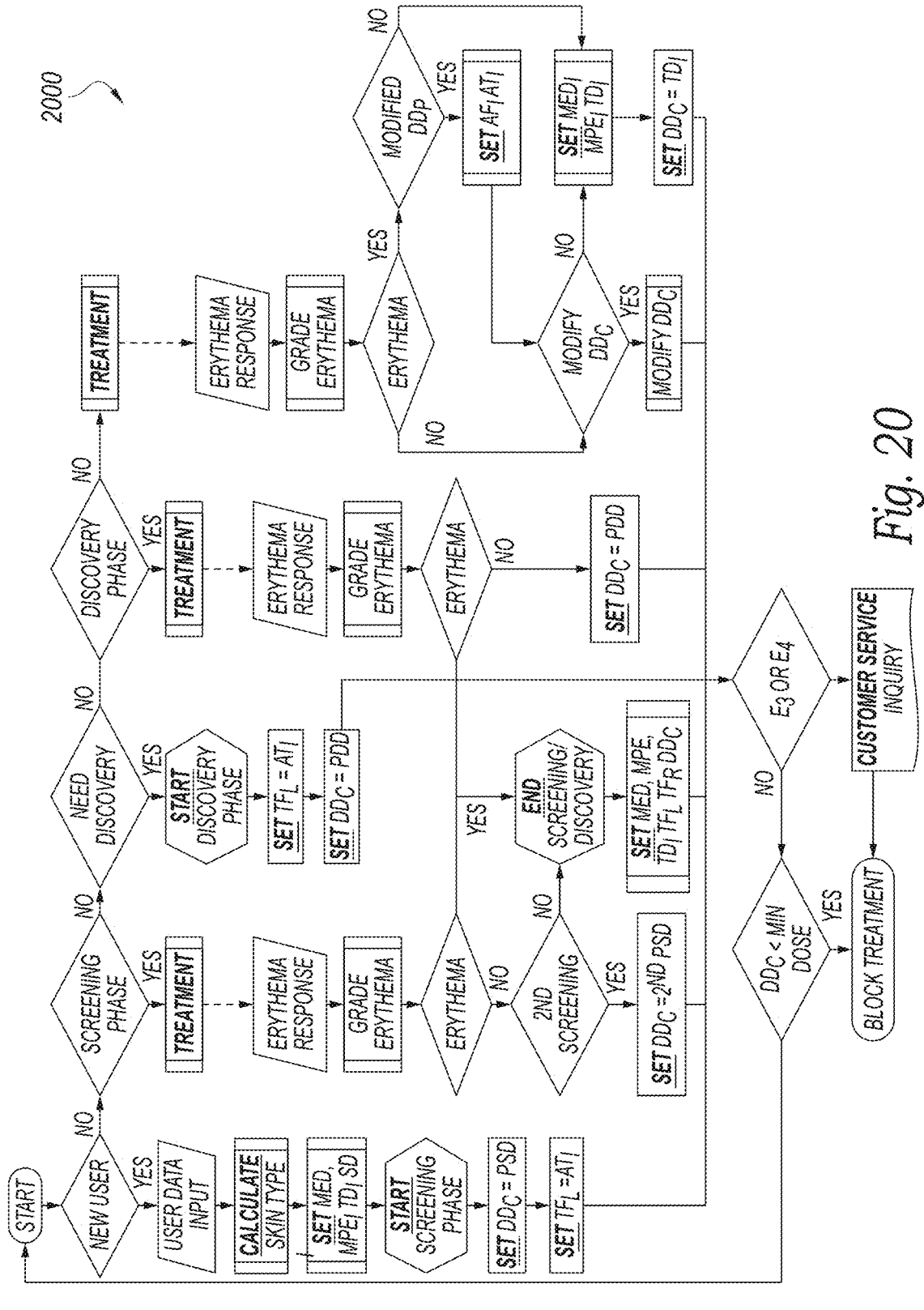
FIG. 20 is a flow diagram illustrating a self-care phototherapy kiosk dynamic dosing routine configured in accordance with embodiments of the present technology.

FIG. 20 is a flow diagram illustrating a self-care phototherapy kiosk dynamic dosing routine 2000 configured in accordance with embodiments of the present technology. The routine 2000 provides the overall workflow for a self-service phototherapy kiosk with a dynamic dosing system (e.g., the phototherapy system 100 and the dynamic dosing system 105 described above).

Figure 22:
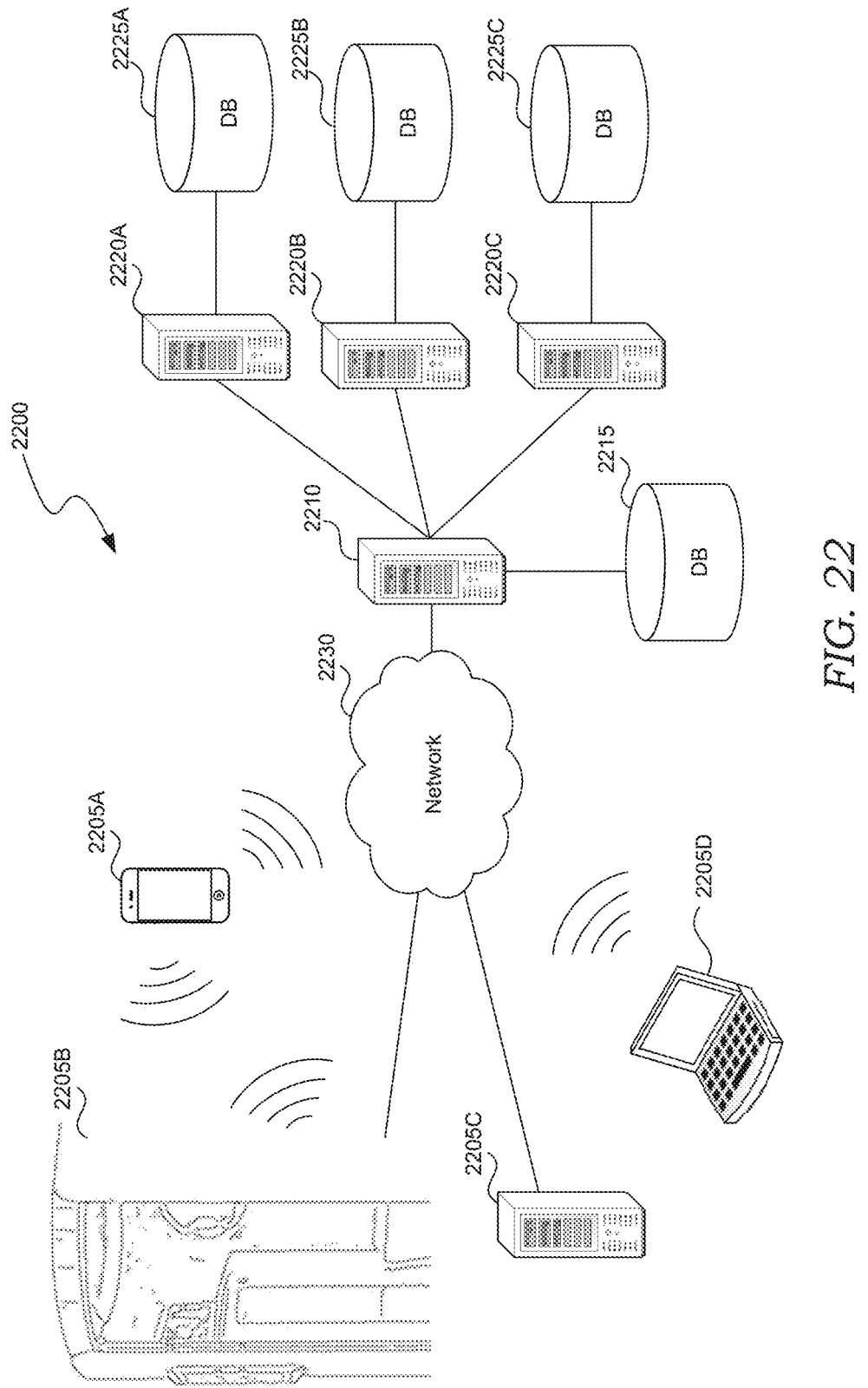
FIG. 22 is a block diagram illustrating an overview of an environment in which some implementations can operate.

In various embodiments, the dynamic dosing system 105 can include a database (e.g., as illustrated in FIG. 22) that includes the data received from users, including age, gender, BMI, skin type, photosensitivity, erythema response, medications, and/or other parameters that may affect skin type classifications and dosage recommendations and adjustments. The dynamic dosing system 105 can use machine learning and artificial intelligence to analyze this data to further subdivide skin types and skin type characteristics to create more refined and accurate assessments of user's skin. For example, the dynamic dosing system 105 can use machine learning to analyze previous user data to refine how a user's age and/or age increases will affect the user's MED and MPE, whether specific ages (e.g., 21, 40-50, >75) or changes in age (e.g., 6 months, 1 year, 2 years, 5 years, 10 years) cause greater or lesser impacts on these characteristics, and/or how age impacts users differently depending on the user's other characteristics (e.g., BMI, skin pigmentation, hair color, gender). The dynamic dosing system 105 can then use artificial intelligence to refine the determination of MPE, MED, dosage, and/or other parameters associated with providing phototherapy via the SPKs disclosed herein. Furthermore, as the phototherapy system 100 receives more data from users, the dynamic dosing system 105 will continuously grow more intelligent and predictive of how a user's skin will respond to phototherapy sessions. Accordingly, the dynamic dosing system 105, via machine learning and/or artificial intelligence, will be able to more accurately make initial and future assessments of user's skin characteristics and effective dosage.

Selected Devices, Systems and Environments for Phototherapy Systems

FIG. 21 is a block diagram illustrating an overview of devices on which some implementations of the disclosed technology can operate. The devices can comprise hardware components of a device 2100 that can control an SPK (e.g., the SPK 104 described with respect to FIG. 1). In some implementations, device 2100 can be integrated into the SPK, can be a server system in communication with the SPK, or can be a personal computing device either directly in communication with the SPK or in communication with the server system. The device 2100 can include one or more input devices 2120 that provide input to the CPU(s) (processor(s)) 2110, notifying it of actions. The actions can be mediated by a hardware controller that interprets the signals received from the input device and communicates the information to the CPU 2110 using a communication protocol. Input devices 2120 include, for example, a touchscreen (e.g., the user interfaces 102 on the SPK 104 of FIG. 1), a touchpad, a microphone, a wearable input device, a camera or image-based input device, a mouse, a keyboard, a temperature sensor, a motion sensor, a pressure pad, ultrasound sensor, a contact switch, a current sensor, an iridescence sensor, or other user input devices.

CPU 2110 can be a single processing unit or multiple processing units in a device or distributed across multiple devices. CPU 2110 can be coupled to other hardware devices, for example, with the use of a bus, such as a PCI bus or SCSI bus. The CPU 2110 can communicate with a hardware controller for devices, such as for a display 2130. The display 2130 can be used to display text and graphics. In some implementations, the display 2130 provides graphical and textual visual feedback to a user. In some implementations, the display 2130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 2140 can also be coupled to the processor, such as a network card, video card, audio card, USB, firewire or other external device, camera, printer, speakers, storage drive, etc. In some implementations, the device 2100 also includes a communication device capable of communicating wirelessly or wire-based with a network node. The communication device can communicate with another device or a server through a network using, for example, TCP/IP protocols. The device 2100 can utilize the communication device to distribute operations across multiple network devices.

The CPU 2110 can have access to a memory 2150 that is in the device 2100 or distributed across multiple devices. A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. The memory 2150 can include program memory 2160 that stores programs and software, such as an operating system 2162, phototherapy kiosk controller 2164, and other application programs 2166. The memory 2150 can also include data memory 2170 that can include user profile information, treatment parameters, kiosk usage history, user question responses, medical data, configuration data, settings, user options or preferences, etc., which can be provided to the program memory 2160 or any element of the device 2100.

Some implementations can be operational with numerous other computing system environments or configurations. Examples of computing systems, environments, and/or configurations that may be suitable for use with the technology include, but are not limited to, SPKs, other phototherapy kiosks, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

FIG. 22 is a block diagram illustrating an overview of an environment 2200 in which some implementations of the disclosed technology can operate. Environment 2200 can include one or more client computing devices 2205A-D, examples of which can include the device 2100 of FIG. 21. For example, device 2205A is a mobile computing device, device 2205B is a phototherapy kiosk or SPK, device 2205C is a server system, and device 2205D is a personal computer. Client computing devices 2205 can operate in a networked environment using logical connections 2210 through network 2230 to one or more remote computers, such as a server computing device.

In some implementations, a server 2210 can be an edge server which receives client requests and coordinates fulfillment of those requests through other servers, such as servers 2220A-C. Server computing devices 2210 and 2220 can comprise computing systems, such as the device 2100. Though each server computing device 2210 and 2220 is displayed logically as a single server, server computing devices can each be a distributed computing environment encompassing multiple computing devices located at the same or at geographically disparate physical locations. In some implementations, each server 2220 corresponds to a group of servers.

Client computing devices 2205 and server computing devices 2210 and 2220 can each act as a server or client to other server/client devices. The server 2210 can connect to a database 2215. Servers 2220A-C can each connect to a corresponding database 2225A-C. As discussed above, each server 2220 can correspond to a group of servers, and each of these servers can share a database or can have their own database. Databases 2215 and 2225 can warehouse (e.g. store) information such as user account data, session history, treatment parameter selection criteria, medical records, etc. Though databases 2215 and 2225 are displayed logically as single units, databases 2215 and 2225 can each be a distributed computing environment encompassing multiple computing devices, can be located within their corresponding server, or can be located at the same or at geographically disparate physical locations.

The network 2230 can be a local area network (LAN) or a wide area network (WAN), but can also be other wired or wireless networks. The network 2230 may be the Internet or some other public or private network. Client computing devices 2205 can be connected to the network 2230 through a network interface, such as by wired or wireless communication. While the connections between the server 2210 and the servers 2220 are shown as separate connections, these connections can be any kind of local, wide area, wired, or wireless network, including the network 2230 or a separate public or private network.

Figure 23:
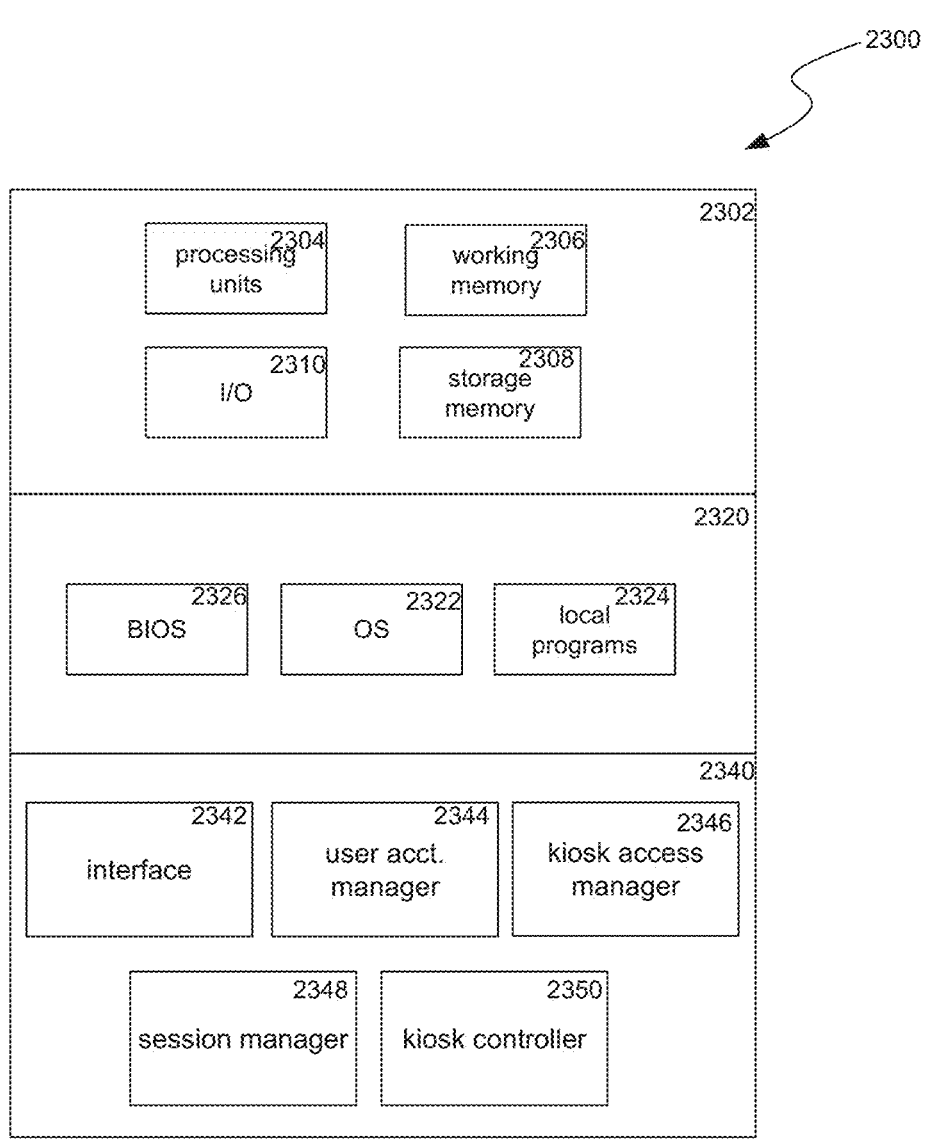
FIG. 23 is a block diagram illustrating components which, in some implementations, can be used in a system employing the disclosed technology.

FIG. 23 is a block diagram illustrating components 2300 which, in some implementations, can be used in a system employing the disclosed technology. The components 2300 include hardware 2302, general software 2320, and specialized components 2340. As discussed above, a system implementing the disclosed technology can use various hardware including processing units 2304 (e.g. CPUs, GPUs, APUs, etc.), working memory 2306, storage memory 2308 (local storage or as an interface to remote storage, such as storage 2215 or 2225), and input and output devices 2310. In various implementations, storage memory 2308 can be one or more of: local devices, interfaces to remote storage devices, or combinations thereof. For example, the storage memory 2308 can be a set of one or more hard drives (e.g. a redundant array of independent disks (RAID)) accessible through a system bus or can be a cloud storage provider or other network storage accessible via one or more communications networks (e.g. a network accessible storage (NAS) device, such as the storage 2215 or storage provided through another server 220). Components 2300 can be implemented in a client computing device such as client computing devices 2205 or on a server computing device, such as the server computing device 2210 or 2220.

The general software 2320 can include various applications including an operating system 2322, local programs 2324, and a basic input output system (BIOS) 2326. Specialized components 2340 can be subcomponents of a general software application 2320, such as local programs 2324. Specialized components 2340 can include a user account manager 2344, a kiosk access manager 2346, a session manager 2348, a kiosk controller 2350, and components which can be used for providing user interfaces, transferring data, and controlling the specialized components, such as interface 2342. In some implementations, the components 2300 can be in a computing system that is distributed across multiple computing devices or can be an interface to a server-based application executing one or more of specialized components 2340.

User account manager 2344 can create, update, and delete user accounts. The user account manager 2344 can be implemented or accessed through a user's personal computing device, a user interface at a phototherapy kiosk, or through a web interface to a server system. The user account manager 2344 can provide forms and questions to a user to identify user information such as skin type, gender, age, etc. The user account manager 2344 can also store user session logs, such as the treatment parameters used and treatment results.

Kiosk access manager 2346 can provide user services to locate and access a phototherapy kiosk. Kiosk access manager 2346 can provide a user interface at a user's personal computing device, at a phototherapy kiosk, or through a web interface to a server system. The user interface provided by the kiosk access manager 2346 can provide a map or listing of phototherapy kiosks, which can be filtered or sorted and can provide corresponding details such as facility or phototherapy kiosk availability times. The user interface provided by kiosk access manager 2346 can also provide functions for a user to schedule a session on a particular phototherapy kiosk or to be added to the phototherapy kiosks waitlist.

Session manager 2348 can obtain data sources comprising one or more of: user account information, a remote payload, user input, phototherapy kiosk measurements, or any combination thereof; determine treatment parameters based on the data sources; transform the treatment parameters into kiosk controls; and use kiosk controller 2350 to operate the phototherapy kiosk using the kiosk controls. Additional details regarding the functions of session manager 2348 are described above and shown in FIGS. 4-20.

Kiosk controller 2350 can include a mapping of treatment parameters to device actuations of the phototherapy kiosk. Treatment parameters specify treatment specifics such as radiation duration, intensity, wavelength filters, and skin areas to treat. Kiosk controls are the instructions to the specific devices embodied in the phototherapy kiosk that implement these parameters. For example, a treatment parameter specifying treatment duration can be converted into a timer setting on one or more radiation lamps. The kiosk controls generated for a set of treatment parameters (and for other session parameters such as environment settings) can then be used to effect actions of the phototherapy kiosk.

EXAMPLES

The following Examples are illustrative of several embodiments of the present technology.

1. A dynamic dosing phototherapy system, comprising:
a self-service phototherapy kiosk ("SPK") comprising a housing defining an at least partially enclosed chamber and a UV radiation assembly configured to emit phototherapeutic UV radiation toward a phototherapy zone within the chamber, the chamber being sized to receive a human body;
a user interface communicatively coupled to the SPK and configured to display a plurality of graphical user interfaces (GUIs) for receiving user inputs from a user related to characteristics affecting photosensitivity and erythema response to a previous phototherapy treatment session;
a dynamic dosing system communicatively coupled to the user interface and the SPK, the dynamic dosing system comprising a computer-readable storage medium storing instructions that, when executed by a computing system, cause the computing system to perform operations comprising—
determining, based at least in part on the user inputs received from the user via the user interface, initial parameters specific to the user, wherein the initial parameters include at least one of a user skin type category, a first individual minimal erythemal dose (MED), a first individual treatment dose, and a first individual treatment frequency, and wherein the initial parameters are used to define a first individual phototherapy protocol;
communicating the first individual phototherapy protocol to the SPK such that the SPK delivers UV radiation in accordance with the first individual phototherapy protocol;
determining, based on the user inputs related to erythema response to the previous phototherapy treatment session, adjustments to the user skin type category, the first individual MED, the first individual treatment dose, and the first individual treatment frequency to define a second individual phototherapy protocol; and
communicating the second individual phototherapy protocol to the SPK such that the SPK delivers UV radiation in accordance with the second individual phototherapy protocol.

2. The dynamic dosing phototherapy system of example 1 wherein the UV radiation assembly is configured to deliver radiation within a predetermined wavelength spectrum between 292 nm and 307 nm to initiate vitamin D production.

3. The dynamic dosing phototherapy system of example 1 or 2 wherein the user interface comprises a plurality of user interfaces including a first user interface and a second user interface, wherein the first user interface is a touchscreen integrated into the SPK and the second user interface is a mobile application configured to be displayed via a personal device of the user.

4. The dynamic dosing phototherapy system of any one of examples 1-3 wherein the user interface comprises a plurality of user interfaces including a first user interface and a second user interface, wherein the first user interface is a first touchscreen carried by the housing of the SPK and accessible via an exterior portion of the SPK, wherein the second user interface is a second touchscreen carried by the housing and accessible from within the chamber of the SPK.

5. The dynamic dosing phototherapy system of any one of examples 1-4 wherein:
the user interface is configured to receive user-specific information related to date of birth, gender, body weight, body mass index, skin tone, hair color, eye color, number of freckles, propensity to sunburn, and propensity to suntan; and
the dynamic dosing system is configured to use the user-specific information to determine the first individual phototherapy protocol.

6. The dynamic dosing phototherapy system of any one of examples 1-5 wherein:
the user interface is configured to receive erythema response information related to at least one of skin color change, discomfort, peeling, blisters, rash, disease symptoms, and mood change; and the dynamic dosing system is configured to apply the erythema response information to determine adjustments to the first individual phototherapy protocol and define the second individual phototherapy protocol.

7. The dynamic dosing phototherapy system of any one of examples 1-6 wherein the instructions of the computer-readable storage medium cause the computing system to perform operations further comprising phototyping the user within at least six predefined skin type categories.

8. The dynamic dosing phototherapy system of any one of examples 1-7 wherein:

the user interface is configured to receive skin typing information that addresses inquiries associated with Fitzpatrick skin typing; and the dynamic dosing system is configured to base the first individual phototherapy protocol at least in part on the skin typing information.

9. The dynamic dosing phototherapy system of any one of examples 1-8 wherein:

the user interface is configured to display images associated with different skin tones and receive user selections associated with the images; and the dynamic dosing system is configured to base the first individual phototherapy protocol at least in part on the user selections associated with the images.

10. The dynamic dosing phototherapy system of any one of examples 1-9 wherein:

the user interface is configured to receive hair color information; and the dynamic dosing system is configured to base the first individual phototherapy protocol at least in part on the hair color information.

11. The dynamic dosing phototherapy system of any one of examples 1-10 wherein:

the user interface is configured to receive freckle information associated with a user's quantity of freckles; and the dynamic dosing system is configured to base the first individual phototherapy protocol at least in part on the freckle information.

12. The dynamic dosing phototherapy system of any one of examples 1-11 wherein:

the user interface is configured to receive sunburn information associated with a user's propensity to sunburn; and the dynamic dosing system is configured to base the first individual phototherapy protocol at least in part on the sunburn information.

13. The dynamic dosing phototherapy system of any one of examples 1-12 wherein:

the user interface is configured to receive suntan information associated with a user's propensity to suntan; and the dynamic dosing system is configured to base the first individual phototherapy protocol at least in part on the suntan information.

14. The dynamic dosing phototherapy system of any one of examples 1-13 wherein the instructions of the computer-readable storage medium cause the computing system to perform operations comprising determining the first treatment dose based on a mean MED range per skin type of the user.

15. The dynamic dosing phototherapy system of any one of examples 1-14 wherein the instructions of the computer-readable storage medium cause the computing system to perform operations comprising determining the first treatment dose based on a mean minimal perceived erythema (MPE) range per skin type of the user.

16. The dynamic dosing phototherapy system of any one of examples 1-15 wherein the instructions of the computer-readable storage medium cause the computing system to perform operations comprising determining the first treatment dose based within a range spanning between a low MPE and high MED for the skin type category of the user when the first individual MED of the user is undefined.

17. The dynamic dosing phototherapy system of any one of examples 1-16 wherein determining the initial parameters specific to the user comprises:

determining the first individual MED, the first individual MPE, and the first individualized treatment dose based on a mean MPE associated with the skin type category of the user, the mean MED associated with the skin type category of the user; and adjusting the first individual treatment dose based on gender and/or age of the user.

18. The dynamic dosing phototherapy system of any one of examples 1-17 wherein:

the SPK is configured to apply a screening dose equivalent to 70% or less than the first individual treatment dose as determined by the dynamic dosing system;

the user interface is configured to receive erythemal response information associated with a skin response to the screening dose; and when an erythemal response occurred in response to the screening dose, the dynamic dosing system is configured to reduce the first individual treatment dose to reflect the erythemal response.

19. The dynamic dosing phototherapy system of any one of examples 1-18 wherein the instructions of the computer-readable storage medium cause the computing system to perform operations comprising determining the first treatment dose based on a reduction factor of 90% or less than an MPE dose associated with the user.

20. The dynamic dosing phototherapy system of example 19 wherein:

the user interface is configured to receive biomarker data associated with a skin response after at least one phototherapy treatment session via the SPK; and the dynamic dosing system is configured to adjust the reduction factor associated with the first individual treatment dose to reflect deviations from an expected biomarker.

21. The dynamic dosing phototherapy system of example 19 wherein:

the user interface is configured to receive efficacy of treatment data associated with a skin response after at least one phototherapy treatment session via the SPK; and the dynamic dosing system is configured to adjust the reduction factor associated with the first individual treatment dose to reflect deviations from an expected efficacy value.

22. The dynamic dosing phototherapy system of any one of examples 1-21 wherein the instructions of the computer-readable storage medium cause the computing system to perform operations further comprising decreasing individual MPE and individual MED for the user annually by a predefined rate.

23. The dynamic dosing phototherapy system of any one of examples 1-22 wherein the instructions of the computer-readable storage medium cause the computing system to perform operations further comprising:

determining whether the second individual treatment dose was subject to a modification from the first individual treatment dose;

when there was a modification, correlating an individual delivery dose to the second individual treatment dose; when there was not a modification— correlating an initial individual delivery dose to the first individual treatment dose, and adjusting the initial individual delivery dose based on at least one of photoadaptation, medication, and recent UV exposure to define the individual delivery dose; and communicating the individual delivery dose to the SPK such that the SPK delivers UV radiation to the user in accordance with the individual delivery dose.

24. The dynamic dosing phototherapy system of any one of examples 1-23 wherein the instructions of the computer-readable storage medium cause the computing system to perform operations further comprising:

increasing an individual delivery dose to compensate for photoadaptation during periods of frequent photo-therapy sessions, wherein the individual delivery dose corresponds to the first individual treatment dose, the second individual treatment dose, or an adjusted individual treatment dose configured to be emitted by the SPK; and decreasing the individual delivery dose to compensate for photoadaptation during periods of infrequent photo-therapy sessions.

25. The dynamic dosing phototherapy system of any one of examples 1-24 wherein the instructions of the computer-readable storage medium cause the computing system to perform operations further comprising resetting the individual delivery dose after predefined period without any phototherapy sessions.

26. The dynamic dosing phototherapy system of any one of examples 1-25 wherein the instructions of the computer-readable storage medium cause the computing system to perform operations further comprising:

selecting erythema response questions to be answered by the user based the time interval between last UVR exposure; and sending the selected questions to the user via at least one of email, text message, and push notification via a mobile application.

27. The dynamic dosing phototherapy system of any one of examples 1-26 wherein the instructions of the computer-readable storage medium cause the computing system to perform operations further comprising:

determining escalating erythemal events based on user-specific erythema response information received via the user interface, wherein the escalating erythemal events comprise MPE, MED, second degree erythema, third degree erythema, and fourth degree erythema; and adjusting a second individual MPE, the second individual MED, and the individual treatment dose based on the determined erythemal events.

28. The dynamic dosing phototherapy system of any one of examples 1-27 wherein the instructions of the computer-readable storage medium cause the computing system to perform operations further comprising:

defining a treatment frequency recommendation and a treatment frequency limit; and adjusting the treatment frequency recommendation and the treatment frequency limit based on whether an individual phototherapy regime is in an active period or maintenance period, wherein the active period is for initial activation of phototherapy treatment and the maintenance period follows the active period.

29. The dynamic dosing phototherapy system of any one of examples 1-28 wherein:

the SPK is configured to deliver a plurality of photosensitivity discovery doses to the user, the photosensitivity discovery doses are configured to increase by predetermined degrees to ascertain an erythemal event for the user;

the user interface is configured to receive erythema response information from the user based on the photosensitivity discovery doses; and the dynamic dosing system is configured to determine individual MPE and/or individual MED based on the erythema response information.

30. The dynamic dosing phototherapy system of any one of examples 1-29 wherein the SPK is one of a plurality of SPKs communicatively coupled to the dynamic dosing system via a communications link.

31. The dynamic dosing phototherapy system of any one of examples 1-30 wherein the dynamic dosing system is configured to determine the user skin type category, the first individual MED, the first individual treatment dose, and the first individual phototherapy protocol based on analysis performed by the dynamic dosing phototherapy system on data from previous users of the dynamic dosing phototherapy system.

32. The dynamic dosing phototherapy system of any one of examples 1-31 wherein the dynamic dosing system is configured to determine adjustments to the user skin type category, the first individual MED, and the first individual treatment dose, and the second individual phototherapy protocol based on analysis performed by the dynamic dosing phototherapy system on erythema response data from previous users of the dynamic dosing phototherapy system.

33. A computer-readable storage medium storing instructions that, when executed by a computing system, cause the computing system to perform operations comprising:

determining, based at least in part on user inputs received from a user via a user interface, initial parameters specific to the user, wherein the initial parameters include at least one of a user skin type category, a first individual MED, a first individual treatment dose, and a first individual treatment frequency, and wherein the initial parameters are used to define a first individual phototherapy protocol including a delivery dose of UV radiation;

communicating the first individual phototherapy protocol to a self-service phototherapy kiosk (SPK) such that the SPK delivers UV radiation to the user in accordance with the first individual phototherapy protocol;

determining, based on the user inputs related to erythema response to a previous phototherapy treatment session, adjustments to the user skin type category, the first individual minimal erythemal dose (MED), the first individual treatment dose, and the first individual treatment frequency to define a second individual phototherapy protocol; and communicating the second individual phototherapy protocol to the SPK such that the SPK delivers UV radiation to the user in accordance with the second individual phototherapy protocol.

34. A method for operating a dynamic dosing phototherapy system, the method comprising:

receiving, via a user interface, user inputs related to user-specific characteristics affecting photosensitivity and associated with erythema response to a previous phototherapy treatment session;

determining, based at least in part on user inputs received from a user via a user interface, an initial individual treatment dose and an initial individual phototherapy protocol;

communicating the initial individual phototherapy protocol to a self-service phototherapy kiosk (SPK);

causing the SPK to deliver UV radiation during an initial phototherapy session to the user in accordance with the initial individual phototherapy protocol;

determining, based on the user inputs related to erythema response to the initial phototherapy session, adjustments to the initial individual phototherapy protocol to define an adjusted individual phototherapy protocol; and communicating the adjusted individual phototherapy protocol to the SPK.

35. The method of example 34, further comprising causing the SPK to deliver UV radiation during a second phototherapy session to the user in accordance with the adjusted individual phototherapy protocol.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A method for operating a dynamic dosing phototherapy system, the method comprising:

receiving, via a user interface, first user inputs related to user-specific characteristics affecting photosensitivity and associated with erythema response to a previous phototherapy treatment session;

determining, based at least in part on user inputs received from a user via a user interface, (1) an individual screening phototherapy protocol and (2) an initial individual treatment dose and an initial individual phototherapy protocol;

communicating the individual screening phototherapy protocol and the initial individual phototherapy protocol to an ultraviolet (UV) radiation assembly;

causing the UV radiation assembly to deliver UV radiation during a screening phototherapy session to the user in accordance with the individual screening phototherapy protocol, wherein the individual screening phototherapy protocol comprises causing the UV radiation assembly to deliver a screening dose to the user of 70% or less than an estimated mean minimal erythemal dose (MED) for the user;

receiving, via the user interface, second user inputs associated with an erythema response to the screening phototherapy session; and determining, based on the second user inputs, a suitability of the initial individual phototherapy protocol for the user, wherein:

responsive to a determination that the initial individual phototherapy protocol is not suitable for the user, the method further comprises:

determining adjustments to the initial individual phototherapy protocol to define an adjusted individual phototherapy protocol; and communicating the adjusted individual phototherapy protocol to the UV radiation assembly; or responsive to a determination that the initial individual phototherapy protocol is suitable for the user, the method further comprises communicating the suitability to the UV radiation assembly such that the UV radiation assembly delivers the estimated MED in a next phototherapy session.

2. The method of claim 1 wherein responsive to a determination that the initial individual phototherapy protocol is not suitable for the user, the method further comprises causing the UV radiation assembly to deliver UV radiation during a second phototherapy session to the user in accordance with the adjusted individual phototherapy protocol.

3. The method of claim 1 wherein determining the initial individual phototherapy protocol includes determining a Fitzpatrick skin typing based at least partially on the user inputs.

4. The method of claim 3 wherein determining the initial individual phototherapy protocol is at least partially based on a MED for the Fitzpatrick skin typing determined for the user.

5. The method of claim 1 wherein:

causing the UV radiation assembly to deliver UV radiation during the screening phototherapy session in accordance with the individual screening phototherapy protocol comprises delivering a plurality of photosensitivity discovery doses to the user, wherein the plurality of photosensitivity discovery doses increase by predetermined degrees to ascertain an erythemal event for the user; and receiving the second user inputs comprises receiving the erythema response from the user based on the plurality of photosensitivity discovery doses.

6. The method of claim 5, further comprising determining an individual mean minimal perceived erythema (MPE) and/or individual MED based on the second user inputs, wherein the adjustments to the initial individual phototherapy protocol are based at least partially on the individual MPE and/or individual MED.

7. A method for operating a dynamic dosing phototherapy system, the method comprising:

receiving, from a user via a user interface, first user inputs related to user-specific characteristics affecting photosensitivity;

determining, based at least in part on the first user inputs, an individual screening phototherapy protocol and an individual phototherapy protocol associated with an estimated minimal erythema dose (MED) for the user;

causing, via a controller in communication with an ultraviolet (UV) radiation assembly, the UV radiation assembly to deliver UV radiation to the user during a screening phototherapy session in accordance with the individual screening phototherapy protocol, wherein the individual screening phototherapy protocol comprises causing the UV radiation assembly to deliver a screening dose to the user, wherein the screening dose delivers 70% or less of the estimated MED; and determining, based on second user inputs related to an erythema response to the screening phototherapy session, a suitability of the first individual phototherapy protocol for the user, wherein:

responsive to a determination that the individual phototherapy protocol is suitable for the user, the method further comprises communicating the suitability to the controller such that the controller operates the UV radiation assembly in accordance with the individual phototherapy protocol to deliver the estimated MED in a second phototherapy session.

8. The method of claim 7 wherein, responsive to a determination that the individual phototherapy protocol is not suitable for the user, the method further comprises:

determining adjustments to the individual phototherapy protocol to define an adjusted individual phototherapy protocol; and causing the UV radiation assembly to deliver UV radiation during a second phototherapy session to the user in accordance with the adjusted individual phototherapy protocol.

9. The method of claim 7 wherein the user interface is a mobile application configured to be displayed via a personal device of the user.

10. The method of claim 7 wherein determining the individual phototherapy protocol includes determining a Fitzpatrick skin typing based at least partially on the first user inputs.

11. The method of claim 10 wherein the individual phototherapy protocol is based at least partially based on a mean MED associated with the Fitzpatrick skin typing determined for the user.

12. The method of claim 10 wherein the individual phototherapy protocol is based at least partially based on a mean minimal perceived erythema (MPE) range associated with the Fitzpatrick skin typing determined for the user.

13. The method of claim 7, further comprising displaying one or more images associated with different skin tones, wherein receiving the first user inputs comprises receiving user selections associated with the one or more images.

14. The method of claim 7, further comprising:

increasing an individual delivery dose in subsequent individual phototherapy protocols to compensate for photoadaptation during periods of frequent phototherapy sessions; and decreasing the individual delivery dose in the subsequent individual phototherapy protocols to compensate for photoadaptation during periods of infrequent phototherapy sessions.

15. The method of claim 7, further comprising displaying one or more erythema response questions to be answered by the user, wherein the second user inputs comprise responses to the one or more erythema response questions.

16. A computer-readable storage medium storing instructions that, when executed by a computing system, cause the computing system to perform operations comprising:

determining, based on first user inputs received from a user via a user interface, parameters specific to the user, wherein the parameters specific to the user include an individual minimal erythemal dose (MED);

determining an individual screening protocol and a first individual phototherapy protocol, wherein the an individual screening protocol is configured to deliver a screening dose of ultraviolet (UV) radiation equal to a fraction of the individual MED from the parameters specific to the user, and wherein the first individual phototherapy protocol is configured to deliver a first dose of UV radiation based at least partially on the parameters specific to the user to deliver the individual MED;

causing a UV radiation assembly to deliver the screening dose of UV radiation to the user during a screening session in accordance with the individual screening protocol;

determining the first individual phototherapy protocol is acceptable based on second user inputs related to an erythema response to the screening dose;

causing the UV radiation assembly to deliver the first dose of UV radiation to the user during a first phototherapy session in accordance with the first individual phototherapy protocol; and determining escalating erythemal events based on third user inputs related to an erythema response to the first dose of UV radiation and adjustments to the parameters specific to the user based on the determined escalating erythemal events to define a second individual phototherapy protocol, wherein the determined escalating erythemal events comprise minimal perceived erythema (MPE), MED, second degree erythema, third degree erythema, and fourth degree erythema.

17. The computer-readable storage medium of claim 16 wherein the operations further comprise causing the UV radiation assembly to deliver a second dose of UV radiation to the user during a second phototherapy session in accordance with the second individual phototherapy protocol.

18. The computer-readable storage medium of claim 16 wherein the operations further comprise displaying one or more questions to the user, via the user interface, related to the erythema response to the first dose of UV radiation, and wherein the second user inputs comprise responses to the one or more questions.

19. The computer-readable storage medium of claim 18, wherein the operations further comprise:

increasing an amount of UV radiation delivered in subsequent individual phototherapy protocols to compensate for photoadaptation during periods of frequent phototherapy sessions; and decreasing the amount of UV radiation delivered in the subsequent individual phototherapy protocols to compensate for photoadaptation during periods of infrequent phototherapy sessions.

* * * * *